US008124837B2

United States Patent
Kirkpatrick et al.

(10) Patent No.: US 8,124,837 B2
(45) Date of Patent: Feb. 28, 2012

(54) **ENGINEERING RESISTANCE TO PIERCE'S DISEASE BY EXPRESSION OF A *XYELLA FASTIDIOSA* HECA-LIKE HEMAGGLUTININ PROTEIN**

(75) Inventors: Bruce C. Kirkpatrick, Davis, CA (US); Magalie R. R. Guilhabert, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 845 days.

(21) Appl. No.: 11/793,916

(22) PCT Filed: Dec. 20, 2005

(86) PCT No.: PCT/US2005/046395
§ 371 (c)(1),
(2), (4) Date: Sep. 5, 2008

(87) PCT Pub. No.: WO2006/069160
PCT Pub. Date: Jun. 29, 2006

(65) Prior Publication Data
US 2009/0217421 A1    Aug. 27, 2009

Related U.S. Application Data

(60) Provisional application No. 60/638,988, filed on Dec. 22, 2004.

(51) Int. Cl.
*A01H 5/00* (2006.01)
*C12N 15/09* (2006.01)
*C12N 15/82* (2006.01)
*C12N 1/21* (2006.01)

(52) U.S. Cl. ............... 800/279; 435/320.1; 435/468; 435/252.3; 435/252.34; 800/278; 800/298; 800/295; 800/301

(58) Field of Classification Search ............... None
See application file for complete search history.

(56) References Cited

OTHER PUBLICATIONS

Fourgoux-Nicol et al (1999), Plant Molecular Biology 40: 857-872.*
Kaye et al. Plant Physiology (1998) 116:1367-1377.*
Guilhabert, M. R. et al. (2005). "Identification of *Xylella fastidiosa* Antivirulence Genes: Hemagglutinin Adhesins Contribute to *X. fastidiosa* Biofilm Maturation and Colonization and Attenuate Virulence," *Molecular Plant-Microbe Interactions* 18(8):856-568.
International Search Report mailed Sep. 25, 2007, for PCT Application No. PCT/US05/46395 filed Dec. 20, 2005, 10 pages.
Rojas, C. M. et al. (Oct. 1, 2002). "HecA, a Member of a Class of Adhesins Produced by Diverse Pathogenic Bacteria, Contributes to the Attachment, Aggregation, Epidermal Cell Killing, and Virulence Phenotypes of *Erwinia chrysanthemi* EC16 on *Nicotiana clevelandii* Seedlings," *Proceedings of the National Academy of Sciences of the United States of America* 9(20):13142-13147.

* cited by examiner

*Primary Examiner* — Medina A Ibrahim
(74) *Attorney, Agent, or Firm* — Morrison & Foerster LLP

(57) ABSTRACT

*Xylella fastidiosa* (Xj), a Gram-negative, xylem-limited bacterium, is the causal agent of several economically important plant diseases, including Pierce's disease (PD) and Citrus Variegated Chlorosis (CVC). Identified is a HccA-like hemagglutinin gene in *Xylella fastidiosa* involved in the virulence of the pathogen. In essence this protein is a "molecular glue" that specifically attaches to the surface of *Xylella fastidiosa* causing *Xylella fastidiosa* cells to form aggregates. If this protein is expressed in trans-genic plants, this protein could cause greater aggregation of *Xylella fastidiosa* cells in planta, thus slowing down the movement of *Xylella fastidiosa* and decreasing disease symptoms. The protein can also be introduced into the plant by inoculation with a plant endophyte which expresses and secretes a HecA-like hemagglutinin. Thus plants containing increased levels of a *Xylella fastidiosa* HecA-like hemagglutinin protein could have an increased level of field resistance to disease caused by *Xylella fastidiosa*.

18 Claims, 7 Drawing Sheets

Figure 2

A - Disease progression of Chardonnay grapevines inoculated with wild type or Tn5 mutants of *Xf*

B - Disease progression of Chenin Blanc grapevines inoculated with wild type or Tn5 mutants of *Xf*

C - Disease progression of Thompson seedless grapevines inoculated with wild type or Tn5 mutants of *Xf*

Figure 3

```
       PD2116  REAKRNLITSIVTGIASTTHTDAATATHAAIAAVDNNWLAAKQYVQMVSEELEAATEKDK  120
       PD2110  REAKRNLITSIVTGIASTTHTDAATATHAAIAAVDNNWLAAKQYVQMVSEELEAATEKDK  120
*HxfB (PD1792) LTLGWVTITGIATAQVVADPHAPGQQRPTVLAAPNG-------TPLINIQTPSPAGVSR  105
      *PD1246  LSLGMVSITGMATAQVVADPHAPGQQRPTILTAPNG-------APLINIQTPSPAGVSR  105
*HxfA (PD2118) LTLGWVTITGIATAQVVADPHAPGQQRPTVLAAPNG-------TPLINIQTPSPAGVSR   87
       *HecA   ALVWLTGLQPVLPAMAAGVTVASGN--TALEAAGNG-------VPVVNIATPDASGLSH   80
       PD0988  ALDHYRVQGGAIQIDGLGLDSHSTDYTALIARTVQLN-------AGLMAHTLQTTTGPAT   97
       PD0986  ITKIASPASRLKAAAAKELMYNTEQGNYSNLVYLEGHSRGTMTLSNALRVLAGENVGDTK  116

PD2116  GRLEEEKVRAKWREISAR-QDKLTADGLLKGLKESGISNINGLEHLILHPVDVFHELEKI  179
       PD2110  GRLEEEKVRAKWREISAR-QDKLTADGLLKGLKESGISNINGLEHLILHPVDVFHELEKI  179
*HxfB (PD1792) NTYQQFDITPQGAILNN--ARTPTQT--HLAGTVQGNPWLAAGTAKIILNEVNS------  155
      *PD1246  NTYQQFDITPQGAILNN--ARTPTQT--HLAGTVQGNPWLAAGTAKIILNEVNS------  155
*HxfA (PD2118) NTYQQFDITPQGAILNN--ARTPTQT--HLAGTVQGNPWLAAGTAKIILNEVNS------  137
       *HecA   NRYHDFNVDNRGLILNNG-TARLTPS-QLGGLIQNNPNLNGRAAAAILNEVVS-------  131
       PD0988  VALDGHPTASLPAPPGDR-PTVALDVSALGGMYAGKITLIGTEHGLGVRNAGQLSATS--  154
       PD0986  LEVLAYNPAAEGNRLNTTYQAYTKPTHQLGELVTAGIEKLLEITKIASPASRLKAAAAKE  176

NPNL                NPYGI  CXXC
       PD2116  LTHPKLLVQLGERAVQDLLNKVSRMAEALYVGG--DQHAKQFGEDLGSVIADVGFALAAA  237  (SEQ ID NO: 1)
       PD2110  LTHPKLLVQLGERAFQELLNKVSRMSEALIVGG--DQHAKQFGEDLGSVIADVGFALAAA  237  (SEQ ID NO: 2)
*HxfB (PD1792) ------------------PTSTQLHGTMEVAG---ARAQLIIANPSGITCNGCGVINAHQ  194  (SEQ ID NO: 3)
      *PD1246  ------------------PTSTQLHGTMEVAG---ARAQLIIANPSGITCNGCGVINAHQ  194  (SEQ ID NO: 4)
*HxfA (PD2118) ------------------STPSQLHGSMEVAG---ARAQLIIANPSGITCNGCGVINAHQ  176  (SEQ ID NO: 5)
       *HecA   ------------------PNRSRLAGYLEVAG---QAANVVANPYGITCSGCGFLNTPR   170  (SEQ ID NO: 6)
       PD0988  ------------------APITVTVDGLLENTGRLQSATDTQLNATAEVNNSGLISAAQT  196  (SEQ ID NO: 7)
       PD0986  LMYN--------------TEQGNYSNLVYLEG--HSRGTMTLSNALRVLAADHVLSDTLE  220  (SEQ ID NO: 8)
```

1 2

ENGINEERING RESISTANCE TO PIERCE'S DISEASE BY EXPRESSION OF A *XYELLA FASTIDIOSA* HECA-LIKE HEMAGGLUTININ PROTEIN

CROSS REFERENCE TO RELATED APPLICATIONS

This application is a U.S. national phase application of International Application No. PCT/US2005/046395, filed Dec. 20, 2005, which claims priority to U.S. Provisional Patent Application No. 60/638,988, filed Dec. 22, 2004, the contents of which are hereby incorporated by reference into the present disclosure in their entirety.

GOVERNMENT RIGHTS

This invention was made with Government support from the California Department of Food and Agriculture (03-0287), USDA CSREES 2002-34442-12461 and UC Division of Agriculture and Natural Resources Pierce's Disease Research Grant (SA6627). The Government may have certain rights in this invention.

FIELD OF THE INVENTION

This invention is in the field of pest resistance. Specifically the invention relates to the resistance of plants against the bacterium *Xylella fastidiosa*, achieved by expression in plants of a gene encoding a bacterial HecA-like hemagglutinin.

BACKGROUND OF THE INVENTION

*Xylella fastidiosa* (Xf) is a Gram-negative, xylem-limited bacterium that is transmitted from plant to plant by several xylem-feeding insect vectors. (Hopkins, 1989) Strains of *Xylella fastidiosa* cause diseases in many economically important plants including grapevines (Pierce's Disease), citrus (Citrus Variegated Chlorosis), peach, plum, oleander, elm, sycamore, oak, maple, and coffee (De Lima et al., 1998; Purcell, 1997). The major symptoms of most *Xylella fastidiosa* diseases are associated with water-stress, due to reduced xylem flow, which is thought to result from occlusion of the xylem vessels by bacterial aggregates that likely contain EPS (da Silva et al., 2001), gums and tyloses (Hopkins 1989). The onset of disease is as follows: leaf margins progressively dry inward, scorched leaf blades abscise and fall, leaving the petiole attached to the cane (match stick symptom). The canes then lignify irregularly, which produces patches of green tissues surrounded by mature, brown tissue (green island symptom). Finally the whole plant dies. Thus there is a tremendous need to develop plants that are resistant to *Xylella fastidiosa* infection.

SUMMARY OF THE INVENTION

In one embodiment, the present invention meets these needs by providing transgenic plants or genetically engineered plant endophytes that express a HecA-like hemagglutinin, or a fragment thereof, which inhibits the growth and spread of *Xylella fastidiosa*, thereby providing resistance to Pierce's Disease and other diseases caused by *Xylella fastidiosa*. The HecA-like hemagglutinin proteins include the amino acid sequences NPNL (amino acids 114 through 117 of SEQ ID NO: 6) and NPYGI (amino acids 154 through 158 of SEQ ID NO: 6) and may be from *Xylella fastidiosa*. The HecA-like hemagglutinin may be expressed in various plants such as grapevines, citrus, peach, plum, oleander, elm, sycamore, oak, maple and coffee or in plant endophytes growing in such plants. In another embodiment, the present invention is further directed to seeds produced by the transgenic plants of the invention, or seeds produced by plants infected with a transgenic endophyte. In another embodiment the invention also provides for methods of generating such transgenic plants and plant endophytes.

In yet another embodiment, the invention is further directed to recombinant HecA-like hemagglutinins or fragments thereof which confer resistance to *Xylella fastidiosa* when expressed in plants or plant microbial endophytes which are present in plants. Two examples of these proteins are HxfA and HxfB.

In yet another embodiment, the invention is further directed to isolated nucleic acid sequences which encode recombinant *Xylella fastidiosa* HecA-like hemagglutinins or fragments thereof which confer resistance to *Xylella fastidiosa* when expressed in plants or plant endophytes present in plants.

In yet another embodiment, the invention is further directed to recombinant constructs containing such isolated nucleic acids. The recombinant constructs may further include a promoter. The promoter may be a constitutive promoter, inducible promoter, tissue- or cell-specific promoter, or a developmentally-regulated promoter. The promoters may be expressible in a plant, a bacteria and/or a plant endophyte. The recombinant constructs may further be in a vector. By way of example but not limitation, the vector may be a cloning, expression, transformation, or transfection vector.

In another embodiment, the invention is further directed to isolated nucleic acids encoding HecA-like hemagglutinins and paralogs, homologs and orthologs of the protein. The HecA-like hemagglutinin protein encoding nucleic acid sequence as defined herein refers to any sequence that hybridizes to the nucleic acid molecule encoding the HecA-like hemagglutinin, or the complement thereof under at least low stringency, preferably moderate, high or very high stringency conditions, or is about 85%, 90%, 95% or 97% identical in the nucleic acid sequence, or encodes a polypeptide with HecA-like hemagglutinin activity having at least about 85%, 90%, 95% or 97% sequence identity to the HecA-like hemagglutinin protein, and confer resistance to disease caused by *Xylella fastidiosa*.

Yet another aspect of the present invention is a host cell containing any of the above nucleic acids, vectors, or constructs. Such nucleic acids, vectors and construct may be introduced into a prokaryotic or eukaryotic host cell. Preferred host cells include bacterial cells such as *E. coli* and plant endophytes from such genera as *Pseudomonas, Agrobacterium, Bacillus*, and others, yeast cells, and plant cells. The nucleic acids, vectors and constructs may be introduced into the host cells so that the expression of the nucleic acid may be controlled or regulated. The introduction of the construct into the host cell may be transient or stable. The control or regulation may include tissue-specific promoters designed to express the isolated nucleic acids in given tissues. Such regulation may be directed to constitutive expression. The regulation may be responsive to various biotic, abiotic and artificial stimuli, relative to the native promoter. In yet another embodiment, the invention is further directed to plants which contain the host cells.

BRIEF DESCRIPTION OF THE DRAWINGS

FIG. 2 shows disease progression of various grapevine varieties inoculated with wild type or Tn5 mutants of *Xylella fastidiosa*. Disease severity was based on a visual disease scale, from 0 to 5 and was assessed 10, 14, 16, 18, 20 and 32 weeks after inoculations. The data is an average of two independent replications (6 plants total) for the inoculations in Chardonnay grapevines and one replication (3 plants total) for the inoculations in Chenin Blanc and Thompson seedless grapevines. PspB *Xylella fastidiosa* mutant was lost in storage and was not inoculated in Chenin Blanc and Thompson seedless. HxfB was only inoculated in Chardonnay grapevines. (a)=disease severity was rated as 0 (healthy) 10 weeks after inoculation. (b)=water control was not showing symptom during the course of disease progression (disease severity was 0). *=mutant values were not significantly different from wild type values at the 95% confidence level (p<0.05).

FIG. 3 shows an alignment of the N-terminal region of the hemagglutinin-like proteins from *X. fastidiosa* and the hemagglutinin protein, HecA from *E. chrysanthemi*. Letters and numbers on the left indicate the name of the *Xylella fastidiosa* genes as described in the *Xylella fastidiosa* PD genome web site (University of Campinas, Brazil, Institute of Computing, Library for Bioinformatics). HxfA and HxfB indicate the *Xylella fastidiosa* hemagglutinin proteins, PD2118 (SEQ ID NO: 5, GenBank accession number NP 780288) and PD1792 (SEQ ID NO: 3, GenBank accession number NP 779977), respectively. HecA indicates the name of the hemagglutinin protein from *E. chrysanthemi* (GenBank accession number AF501263). Numbers on the right indicate amino acid residues. The two conserved secretion domains NPNL (amino acids 114 through 117 of SEQ ID NO: 6) and NPYGI (amino acids 154 through 158 of SEQ ID NO: 6), of proteins secreted through the two-partner secretion (TPS) pathway are underlined (Schonherr et al., 1993). N, P, L, G and I indicate asparagine, proline, leucine, glycine and isoleucine, respectively. Several Tps proteins, including HecA, harbor a CXXC motif (SEQ ID NO: 33), which is absent in others. These cysteines (C) are not essential for secretion (Schonherr et al., 1993). An asterisk (*) indicates that Tps secretion domains were conserved in those amino acid sequences.

BRIEF DESCRIPTION OF THE SEQUENCE LISTING

Figure 1:
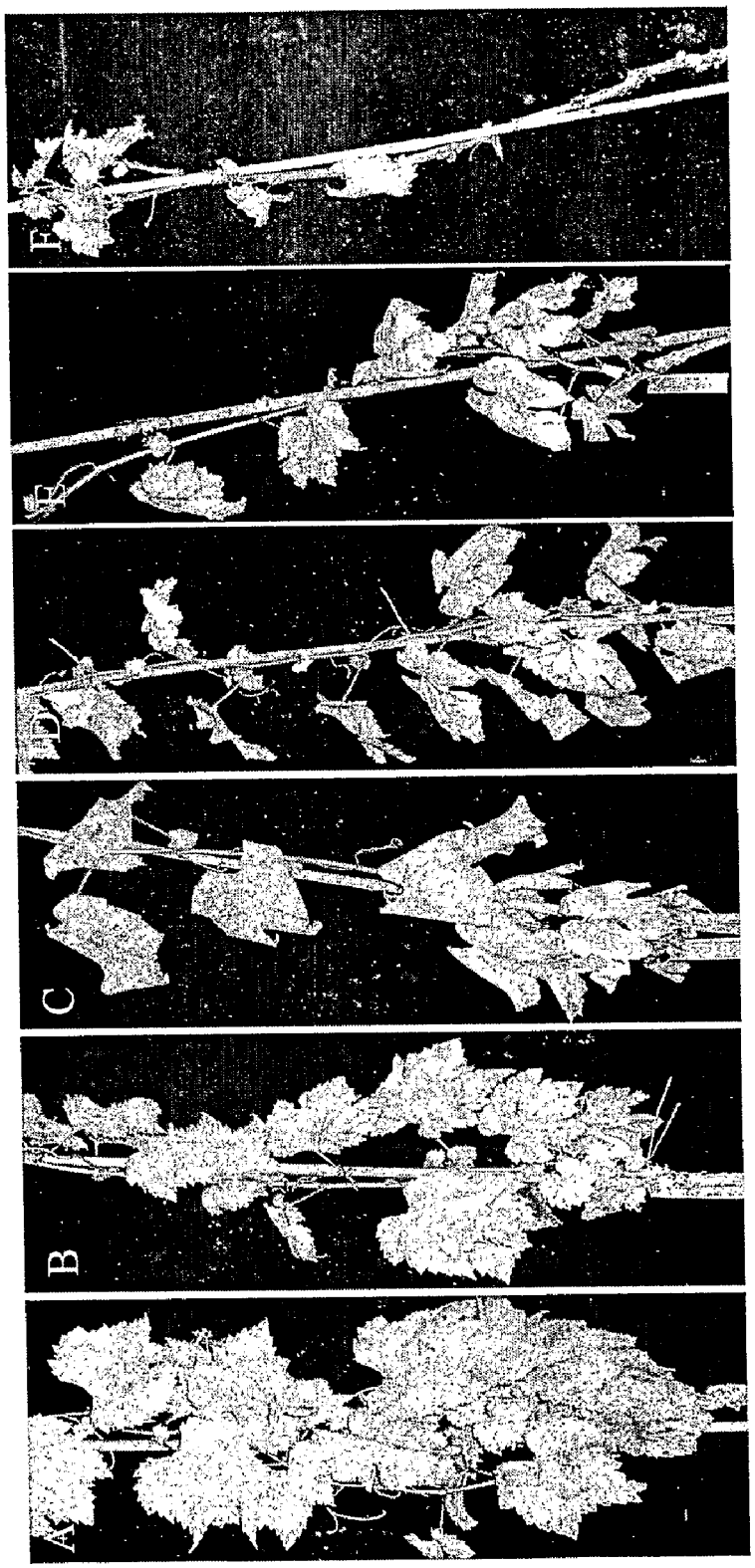
FIG. 1 shows Pierce's disease symptoms in grapevines. A shows mock inoculation of Chardonnay grapevines and B shows Chardonnay grapevines infected with the wild type strain Temecula showing a disease rating of 1, C shows a disease rating of 2, D shows a disease rating of 3, E shows a disease rating of 4, and F shows a disease rating of 5. Note the general health of the plants and the number of scorched leaves.
Figure 4:
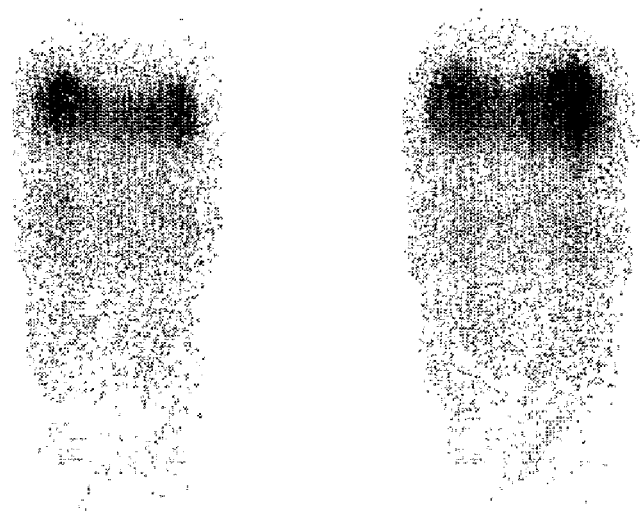
FIG. 4 shows Lipopolysaccharide (LPS) profiles of strains of *Xylella fastidiosa* as revealed by SDS-PAGE and silver staining. In lane 1 is wild type strain and lane 2 is XF1542 mutant strain.

SEQ ID NO: 1 is the amino acid sequence of PD2116, a *Xylella fastidiosa* hemagglutinin-like protein.

SEQ ID NO: 2 is the amino acid sequence of PD2110, a *Xylella fastidiosa* hemagglutinin-like protein.

SEQ ID NO: 3 is the amino acid sequence of PD1792, a *Xylella fastidiosa* hemagglutinin-like protein, also referred to as HxfB.

SEQ ID NO: 4 is the amino acid sequence of PD1246, a *Xylella fastidiosa* hemagglutinin-like protein.

SEQ ID NO: 5 is the amino acid sequence of PD2118, a *Xylella fastidiosa* hemagglutinin-like protein, also referred to as HxfA.

SEQ ID NO: 6 is the amino acid sequence of HecA, a hemagglutinin protein from *E. chrysanthemi*.

SEQ ID NO: 7 is the amino acid sequence of PD0988, a *Xylella fastidiosa* hemagglutinin-like protein.

SEQ ID NO: 8 is the amino acid sequence of PD0986, annotated as a *Xylella fastidiosa* hemagglutinin-like protein (Van Sluys et al. 2003).

SEQ ID NO: 9-32 are sequences of primers used herein.

DETAILED DESCRIPTION OF THE INVENTION

In one embodiment, the present invention provides transgenic plants or genetically engineered plant endophytes that are present in plants that express a HecA-like hemagglutinin, or a fragment thereof, which inhibits the growth and spread of *Xylella fastidiosa*, thereby providing resistance to Pierce's Disease and other diseases caused by *Xylella fastidiosa*. The HecA-like hemagglutinin may be isolated from *Xylella fastidiosa*

Before explaining at least one embodiment of the invention in detail, it is to be understood that the invention is not limited in its application to the details of construction and the arrangement of the components set forth in the following description. The invention is capable of other embodiments or of being practiced or carried out in various ways. Also, it is to be understood that the phraseology and terminology employed herein is for the purpose of description and should not be regarded as limiting.

Throughout this disclosure, various publications, patents and published patent specifications are referenced. The disclosures of these publications, patents and published patent specifications are hereby incorporated by reference into the present disclosure to more fully describe the state of the art to which this invention pertains. The practice of the present invention will employ, unless otherwise indicated, conventional techniques of plant breeding, immunology, molecular biology, microbiology, cell biology and recombinant DNA, which are within the skill of the art. See, e.g., Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel, et al. eds., (1987); Plant Breeding: Principles and Prospects (Plant Breeding, Vol 1) M. D. Hayward, N. O. Bosemark, I. Romagosa; Chapman & Hall, (1993); Coligan, Dunn, Ploegh, Speicher and Wingfeld, eds. (1995) CURRENT PROTOCOLS IN PROTEIN SCIENCE (John Wiley & Sons, Inc.); the series METHODS IN ENZYMOLOGY (Academic Press, Inc.): PCR 2: A PRACTICAL APPROACH (M. J. MacPherson, B. D. Hames and G. R. Taylor eds. (1995), Harlow and Lane, eds. (1988) ANTIBODIES, A LABORATORY MANUAL, and ANIMAL CELL CULTURE R. I. Freshney, ed. (1987).

Unless otherwise noted, technical terms are used according to conventional usage. Definitions of common terms in molecular biology may be found in Lewin, Genes V, published by Oxford University Press, 1994 (SBN 0-19-854287-9); Kendrew et al. (eds.), The Encyclopedia of Molecular Biology, published by Blackwell Science Ltd., 1994 (SBN 0-632-02182-9); and Robert A. Meyers (ed.), Molecular Biology and Biotechnology, a Comprehensive Desk Reference, published by VCH Publishers, Inc., 1995 (ISBN 1-56081-569-8); Ausubel et al. (1987) Current Protocols in Molecular Biology, Green Publishing; Sambrook et al. (1989) Molecular Cloning: A Laboratory Manual, Cold Spring Harbor, N.Y. Definitions of common terms in plant biology may be found in Esau, Plant Anatomy, published by John Wiley & Sons (1977) (ISBN 0-471-24520-8); and Solomon et al., Biology, published by Saunders College Publishing (1993).

DEFINITIONS

In order to facilitate review of the various embodiments of the invention, the following definitions are provided:

Promoter: A regulatory nucleic acid sequence, typically located upstream (5') of a gene or protein-coding sequence that, in conjunction with various cellular proteins, is responsible for regulating the expression of the gene or protein-coding sequence. The promoters suitable for use in the heterologous nucleic acids of this invention are functional in plants and in other host organisms used for expressing the inventive polynucleotides. Many plant promoters are publicly known. These include constitutive promoters, regulated promoters, inducible promoters, root-, tissue- and cell-specific promoters, and developmentally-regulated promoters. Exemplary promoters and fusion promoters are described, e.g., in WO 02/00894, which is herein incorporated by reference.

The promoters may be those normally associated with a transgene of interest, or heterologous promoters which are derived from genes of other plants, viruses, and plant pathogenic bacteria and fungi. Those skilled in the art will be able without undue experimentation to select promoters that are suitable for use in practicing the subject invention.

Regulated promoter: As used herein, this term refers to any promoter functional in a plant that provides differential expression levels in response to stimuli internal to the plant such as developmental signals. This includes both promoters that increase expression and promoters that decrease expression in response to stimuli or changed external conditions. Many promoters that are regulated promoters are also inducible promoters. For example, promoters that are responsive to auxin are both because they will change levels of expression in response to developmental changes in auxin levels and in response to externally supplied auxin.

Examples of regulated promoters under developmental control include promoters that initiate transcription only, or preferentially, in certain tissues, such as leaves, roots, fruit, seeds, or flowers. Exemplary promoters include the anther specific promoter 5126 (U.S. Pat. Nos. 5,689,049 and 5,689,051, both herein incorporated by reference), glob-1 promoter, and gamma-zein promoter. An exemplary promoter for leaf- and stalk-preferred expression is MS8-15 (see U.S. Pat. No. 5,986,174, herein incorporated by reference). Examples of seed-preferred promoters included, but are not limited to, 27 kDa gamma zein promoter and waxy promoter (Boronat et al. (1986); Reina et al. (1990); and Kloesgen et al. (1986)). Promoters that express in the embryo, pericarp, and endosperm are disclosed in U.S. application Ser. No. 60/097,233 filed Aug. 20, 1998 and U.S. application Ser. No. 60/098,230 filed Aug. 28, 1998 both of which are hereby incorporated by reference. The operation of a promoter may also vary depending on its location in the genome. Thus, a developmentally regulated promoter may become fully or partially constitutive in certain locations. A developmentally regulated promoter can also be modified, if necessary, for weak expression.

Tissue specific promoter: As used herein, this term refers to any promoter functional in a plant that provides differential expression levels in different tissues within the plant. Such promoters may provide tissue specific expression in one or several tissues. Many promoters that are tissue specific are also regulated promoters. For example, some promoters specifically express in plant seeds only during certain stages of the seeds growth cycle.

Examples of tissue specific promoters include those listed above that initiate transcription only, or preferentially, in certain tissues, such as leaves, roots, fruit, seeds, or flowers. Examples from above include anther specific promoters, leaf- and stalk-specific promoters, seed-specific promoters, embryo-specific promoters, pericarp-specific promoters, and endosperm-specific promoters. Additionally, as discussed above under localization, tissue specific expression occurs when there is on average a skewed expression in one or more tissues of a plant when compared to the average expression in the other tissues in such plant.

Sequence Identity: Sequences that show similarity to those described in this application can be identified by computer-based methods, using public domain sequence alignment algorithms and sequence similarity search tools to search sequence databases (public domain databases include Genbank, EMBL, Swiss-Prot, PIR and others).

Similarity searches retrieve and align sequences for comparison with a target sequence to be analyzed (i.e., a query sequence). The optimal alignment between local regions of the compared sequences is known as a local alignment. Sequence comparison algorithms use scoring matrices to assign an overall score to each of the alignments.

Polynucleotide and polypeptide sequences may be aligned, and percentage of identical residues in a specified region may be determined against other polynucleotide and polypeptide sequences, using computer algorithms that are publicly available. The percentage identity score is dependent on the length of the overlap region of the sequences being compared.

The similarity between two nucleic acid sequences, or two amino acid sequences may be expressed in terms of sequence identity (or, for proteins, also in terms of sequence similarity). Sequence identity is frequently measured in terms of percentage identity; the higher the percentage, the more similar the two sequences are. As described herein, homologs and variants of the HecA-like hemagglutinin-encoding nucleic acid molecules may be used in the present invention. Homologs and variants of these nucleic acid molecules will possess a relatively high degree of sequence identity when aligned using standard methods. Such homologs and variants will hybridize under high stringency conditions to one another.

Methods of alignment of sequences for comparison are well known in the art. Various programs and alignment algorithms are described in: Smith and Waterman (1981); Needleman and Wunsch (1970); Pearson and Lipman (1988); Higgins and Sharp (1988); Higgins and Sharp (1989); Corpet et al. (1988); Huang et al. (1992); and Pearson et al. (1994). Altschul et al. (1994) presents a detailed consideration of sequence alignment methods and homology calculations.

The NCBI Basic Local Alignment Search Tool (BLAST) (Altschul et al., 1990) is available from several sources, including the National Center for Biotechnology Information (NCBI, Bethesda, Md.) and on the Internet, for use in connection with the sequence analysis programs blastp, blastn, blastx, tblastn and tblastx. It can be accessed at the NCBI Website. A description of how to determine sequence identity using this program is available at the NCBI website.

Homologs of the disclosed protein sequences are typically characterized by possession of at least 40% sequence identity counted over the full length alignment with the amino acid sequence of the disclosed sequence using the NCBI Blast 2.0, gapped blastp set to default parameters. The adjustable parameters are preferably set with the following values: overlap span 1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity. Proteins with even greater similarity to the reference sequences will show increasing percentage identities when assessed by this method, such as at least about 50%, at least about 60%, at least about 70%, at least about 75%, at least about 80%, at least about 85%, at least about 90% or at least about 95% sequence identity.

Homologs of the disclosed nucleic acid sequences are typically characterized by possession of at least 40% sequence identity counted over the full length alignment with the amino acid sequence of the disclosed sequence using the NCBI Blast 2.0, gapped blastn set to default parameters. In addition, such sequences hybridize to homologous sequences under high stringency conditions. A preferred method utilizes the BLASTN module of WU-BLAST-2 (Altschul et al., 1996); set to the default parameters, with overlap span and overlap fraction set to 1 and 0.125, respectively. Nucleic acid sequences with even greater similarity to the reference sequences will show increasing percentage identities when assessed by this method, such as at least about 50%, at least about 60%, at least about 70%, at least about 75%, at least about 80%, at least about 85%, at least about 90% or at least about 95% sequence identity.

The alignment may include the introduction of gaps in the sequences to be aligned. In addition, for sequences which contain either more or fewer amino acids than a HecA-like hemagglutinin from *Xylella fastidiosa*, it is understood that in one embodiment, the percentage of sequence identity will be determined based on the number of identical amino acids in relation to the total number of amino acids. Thus, for example, sequence identity of sequences shorter than that shown in the figures as discussed below, will be determined using the number of amino acids in the longer sequence, in one embodiment. In percent identity calculations relative weight is not assigned to various manifestations of sequence variation, such as, insertions, deletions, substitutions, etc.

In one embodiment, only identities are scored positively (+1) and all forms of sequence variation including gaps are assigned a value of "0", which obviates the need for a weighted scale or parameters as described herein for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

Proteins can be classified according to their sequence relatedness to other proteins in the same genome (paralogs) or a different genome (orthologs). Ortholog genes are genes that evolved by speciation from a common ancestral gene. These genes normally retain the same function as they evolve. Paralog genes are genes that are duplicated within a genome. These genes may acquire new specificities or modified functions which may be related to the original one. Phylogenetic analysis methods are well-known to those with ordinary skill in bioinformatics.

As will be appreciated by those skilled in the art, the sequences of the present invention may contain sequencing errors. That is, there may be incorrect amino acid sequences, nucleotides, frameshifts, unknown nucleotides, or other types of sequencing errors in any of the sequences; however, the correct sequences will fall within the homology and stringency definitions herein for nucleic acids, and the protein homology described for proteins or polypeptides.

Stringency: Stringency refers to hybridization conditions chosen to optimize binding of polynucleotide sequences with different degrees of complementarity. Stringency is affected by factors such as temperature, salt conditions, the presence of organic solvents in the hybridization mixtures, and the lengths and base compositions of the sequences to be hybridized and the extent of base mismatching, and the combination of parameters is more important than the absolute measure of any one factor.

Very High Stringency: Very high stringency conditions refers to hybridization to filter-bound DNA in 5×SSC, 2% sodium dodecyl sulfate (SDS), 100 µg/ml single stranded DNA at 55-65° C. for 8 hours, and washing in 0.1×SSC and 0.1% SDS at 60-65° C. for thirty minutes.

High Stringency: High stringency conditions refers to hybridization to filter-bound DNA in 5×SSC, 2% sodium dodecyl sulfate (SDS), 100 µg/ml single stranded DNA at 55-65° C. for 8 hours, and washing in 0.2×SSC and 0.2% SDS at 60-65° C. for thirty minutes.

Moderate Stringency: Moderate stringency conditions refers to hybridization to filter-bound DNA in 5×SSC, 2% sodium dodecyl sulfate (SDS), 100 µg/ml single stranded DNA at 55-65° C. for 8 hours, and washing in 0.2×SSC and 0.2% SDS at 50-55° C. for thirty minutes.

Low Stringency: Low stringency conditions refers to hybridization to filter-bound DNA in 5×SSC, 2% sodium dodecyl sulfate (SDS), 100 µg/ml single stranded DNA at 55-65° C. for 8 hours, and washing in 2.0×SSC and 0.2% SDS at 50-55° C. for thirty minutes.

Construct: Unless otherwise stated, the term "construct" refers to a recombinant genetic molecule comprising one or more isolated polynucleotide sequences of the invention.

Genetic constructs used for transgene expression in a host organism comprise a gene promoter sequence operably linked to an open reading frame coding for at least a functional portion of a polypeptide of the present invention and optionally a gene termination sequence 3' downstream of the open reading frame. The open reading frame may be orientated in either a sense or anti-sense direction, depending upon the intended use of the gene sequence. The construct may also comprise selectable marker gene(s) and other regulatory elements for gene expression.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter controls the transcription or expression of the coding sequence. Generally, operably linked DNA sequences are contiguous and, where necessary, join two protein-coding regions in the same reading frame. With respect to polypeptides, two polypeptide sequences may be operably linked by covalent linkage, such as through peptide bonds or disulfide bonds.

Vector: The term "vector" refers to a nucleic acid molecule which is used to introduce a polynucleotide sequence into a host cell, thereby producing a transformed host cell. A "vector" may comprise genetic material in addition to the above-described genetic construct, e.g., one or more nucleic acid sequences that permit it to replicate in one or more host cells, such as origin(s) of replication, selectable marker genes and other genetic elements known in the art (e.g., sequences for integrating the genetic material into the genome of the host cell, and so on).

Transformed: A transformed cell is a cell into which has been introduced a nucleic acid molecule by molecular biology techniques. As used herein, the term transformation encompasses all techniques by which a nucleic acid molecule might be introduced into such a cell, plant or animal cell, including transfection with viral vectors, transformation by *Agrobacterium*, with plasmid vectors, and introduction of naked DNA by electroporation, lipofection, and particle gun acceleration and includes transient as well as stable transformants.

Isolated: An "isolated" biological component (such as a nucleic acid or protein or organelle) has been substantially separated or purified away from other biological components in the cell or the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term embraces nucleic acids including chemically synthesized nucleic acids and also embraces proteins prepared by recombinant expression in vitro or in a host cell and recombinant nucleic acids as defined below. As an example, a gene in a large genomic DNA fragment such as a contig is not sufficiently purified away from other biological components to be considered isolated due to the relatively large amount of extra DNA found in the average contig. As outlined below "recombinant nucleic acids" and "recombinant proteins" also are "isolated" as described above Recombinant: By "recombinant nucleic acid" herein is meant a nucleic acid that has a sequence that is not naturally occurring or has a sequence that is made by an artificial combination of two otherwise separated segments of sequence. This artificial combination is often accomplished by chemical synthesis or, more commonly, by the artificial manipulation of nucleic acids, e.g., by genetic engineering techniques, such as by the manipulation of at least one nucleic acid by a restriction enzyme, ligase, recombinase, and/or a polymerase. Once introduced into a host cell, a recombinant nucleic acid is replicated by the host cell; however, the recombinant nucleic acid once replicated in the cell remains a recombinant nucleic acid for purposes of this invention. By "recombinant protein" herein is meant a protein produced by a method employing a recombinant nucleic acid. As outlined above "recombinant nucleic acids" and "recombinant proteins" also are "isolated" as described above. A gene in a large fragment such as a contig would not be a "recombinant nucleic acid" given that such artificial combination does not relate to the gene. However, if sequences around or within a gene in a contig have been manipulated for purposes relating to that gene (i.e., not merely because the gene is near the end of the contig), then such a gene in a contig would constitute a "recombinant nucleic acid" due to the relative proximity of the recombinant portion of the nucleic acid to the gene in question.

Complementary DNA (cDNA): A piece of DNA that is synthesized in the laboratory by reverse transcription of an RNA, preferably an RNA extracted from cells. cDNA produced from mRNA may include 5' and/or 3' noncoding sequences (i.e., 5' UTR, 3' UTR) but typically lacks internal, non-coding segments (introns) and regulatory sequences, such as promoters, that determine transcription.

Open reading frame (ORF): A continuous coding sequence of a gene flanked by a start and stop codon. An ORF lacks internal termination codons and can usually be translated into an amino acid sequence.

Transgenic plant: As used herein, this term refers to a plant that contains recombinant genetic material not normally found in plants of this type, as well as recombinant genetic material normally found in such plants but in an abnormal position in the genome, and which has been introduced into the plant in question (or into progenitors of the plant) by human manipulation. Thus, a plant into which recombinant DNA is introduced by transformation is a transgenic plant, as are all offspring of that plant that contain the introduced transgene (whether produced sexually or asexually). It is understood that the term transgenic plant encompasses the entire plant and parts of the plant, for instance grains, seeds, flowers, leaves, roots, fruit, pollen, stems etc.

Standard molecular biology methods and plant transformation techniques can be used to produce transgenic plants that produce plants having a recombinant gene or genes providing HecA-like hemagglutinin activity.

Ortholog: Two nucleotide or amino acid sequences are orthologs of each other if they share a common ancestral sequence and diverged when a species carrying that ancestral sequence split into two species, sub-species, or cultivars. Orthologous sequences are also homologous sequences. Orthologous sequences hybridize to one another under high-stringency conditions. The term "polynucleotide", "oligonucleotide", or "nucleic acid" refers to a polymeric form of nucleotides of any length, either deoxyribonucleotides or ribonucleotides, or analogs thereof. The terms "polynucleotide" and "nucleotide" as used herein are used interchangeably. Polynucleotides may have any three-dimensional structure, and may perform any function, known or unknown. The following are non-limiting examples of polynucleotides: a gene or gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. A "fragment" or "segment" of a nucleic acid is a small piece of that nucleic acid.

Gene: A "gene" refers to a polynucleotide containing at least one open reading frame that is capable of encoding a particular protein after being transcribed and translated.

Primer: The terms "primer" and "nucleic acid primer" are used interchangeably herein. A "primer" refers to a short polynucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a polymerase and at a suitable temperature and pH. The primer may be either single-stranded or double-stranded and must be sufficiently long to prime the synthesis of the desired extension product. The exact length of the primer will depend upon many factors, including temperature, source of primer and use of the method.

Polymerase chain reaction: A "polymerase chain reaction" ("PCR") is a reaction in which replicate copies are made of a target polynucleotide using a "primer pair" or a "set of primers" consisting of an "forward" and a "reverse" primer, and a catalyst of polymerization, such as a DNA polymerase, and particularly a thermally stable polymerase enzyme. Methods for PCR are taught in U.S. Pat. No. 4,683,195 (Mullis) and U.S. Pat. No. 4,683,202 (Mullis et al.). All processes of producing replicate copies of the same polynucleotide, such as PCR or gene cloning, are collectively referred to herein as "amplification" or "replication".

Characterization of HecA-Like Hemagglutinins

A hemagglutinin-like gene has been identified in *Xylella fastidiosa* that has 80% amino acid homology with a hemagglutinin gene called HecA from *Erwinia chrysanthemi* (Rojas et al, 2002). HecA mediates surface attachment, cell aggregation and contributes to the virulence of *E. chrysanthemi*. Multiple pathogenicity testing of one *Xylella fastidiosa* HecA homolog, designated as HxfA, clearly shows the HxfA has an important role in *Xylella fastidiosa* virulence. As explained in detail below, the HxfA mutants no longer clump together in liquid culture, as do wild type *Xylella fastidiosa* cells. Scanning electron microscopic examination of cell masses that attach to the inside of a glass flask show the HxfA cells are largely disordered and not attached together by the length of their cell surface like wild type cells (Guilhabert and Kirkpatrick, 2005). This data indicates that HxfA is essentially a molecular "glue" that plays a very important role in cell-cell aggregation. Also identified is another HecA-like hemagglutinin in *Xylella fastidiosa*, designated HxfB, in which mutation also causes the phenotype above.

It is known that one of the virulence determinants of *Xylella fastidiosa* is its ability to systemically colonize susceptible Vitis genotypes and more resistant genotypes have the ability to slow the movement of *Xylella fastidiosa* by producing gums and tyloses (Fry and Mollenhauer, 1990). Following the teachings of one embodiment of this invention, a HecA-like hemagglutinin is introduced and expressed to reasonable levels in the xylem fluid of plants such as grapevines. The HecA-like hemagglutinin may be expressed by introducing the HecA-like hemagglutinin gene into the plant genome directly or by expressing the gene in a plant endophyte that has been introduced into the plant. This protein should act as an adhesive to cause *Xylella fastidiosa* cells to aggregate and reduce the number of planktonic cells that could circulate freely in xylem vessels and initiate new xylem vessel infections by degrading pit membranes that separate xylem elements. If the HecA-like hemagglutinin also associated with the charged cellulose/pectin surfaces of the xylem secondary walls, it could further act as a cellular glue to immobilize and slow the systemic movement of *Xylella fastidiosa*. If this movement was slowed, *Xylella fastidiosa* may not have sufficient time to move back into permanent cordons and establish an overwintering systemic infection before a plant infected with a wild type *Xylella fastidiosa* cells was pruned off during the winter. The end result could be a plant that was far less likely to support overwintering, systemic infections of *Xylella fastidiosa* than a non-engineered plant.

In one embodiment, the present invention is directed to the observation, as more fully described in the examples below, that *Xylella fastidiosa* strains which lack expression of HxfA or HxfB are more virulent that wild type strains, due to increased motility (Guilhabert and Kirkpatrick, 2005). This suggests that expression of a HecA-like hemagglutinin (the product of the HxfA and HxfB genes) in plants would hinder *Xylella fastidiosa* movement and therefore inhibit infection. As such, in one embodiment, the present invention is directed to transgenic plants which express a HecA-like hemagglutinin, and are therefore more resistant to disease caused by *Xylella fastidiosa*. In another embodiment, the present invention is directed to plant endophytes which express a HecA-like hemagglutinin, and which can be introduced into plants to provide resistance to disease caused by *Xylella fastidiosa*.

Constructs

HecA like hemagglutinin The present invention includes various aspects of nucleic acid sequences encoding one or more proteins that provide HecA-like hemagglutinin activity. One structural feature of HecA-like hemagglutinin proteins is the presence of conserved TPS (two partner secretion) domains, illustrated in FIG. 3. There are two conserved sequence domains, NPNL (amino acids 114 through 117 of SEQ ID NO: 6) and NPYGI (amino acids 154 through 158 of SEQ ID NO: 6), which are found in HecA-like hemagglutinins.

A preferred embodiment of the nucleic acid of the present invention is an isolated nucleic acid encoding a HecA-like hemagglutinin protein or fragment thereof having cell clumping activity. Such HecA-like hemagglutinin proteins include HxfA and HxfB. Examples of such nucleic acids include nucleic acids that hybridize to the HecA-like hemagglutinin encoding nucleic acid disclosed herein under low, moderate, high or very high stringency, nucleic acids with 40%, 50%, 60%, 70%, 75%, 80%, 85%, 90%, 95%, or 97% identity to the HecA-like hemagglutinin encoding nucleic acids disclosed herein, and nucleic acids encoding a protein with 40%, 50%, 60%, 70%, 75%, 80%, 85%, 90%, 95%, or 97% identity to the HecA-like hemagglutinin proteins disclosed herein. In addition, the nucleic acids may include nucleic acids that encode proteins that share conserved regions with other HecA-like hemagglutinin proteins when aligned with HecA-like hemagglutinin protein families. Such conserved regions may share 70%, 75%, 80%, 85%, 90%, 95%, or 97% identity.

In addition, the present invention includes the above nucleic acid sequences operably linked to a promoter. The preferred promoter is a heterologous promoter. The choice of promoter will be dictated by the target cell, tissue, and/or development expression pattern in which the HecA-like hemagglutinin protein is to be expressed. Selection of an appropriate promoter functional in a desired target cell is routine in the art. One of skill in the art can use, for example, a constitutive promoter, an inducible promoter or a regulated promoter depending upon the desired pattern of expression.

In addition to natural promoters, mutant promoters and artificial promoters created by splicing distinct regulatory elements may be used.

Another aspect of the present invention is vectors including the nucleic acids and promoter linked constructs described above. There are a wide range of vectors available to one of skill in the art. Such vectors can include, without limitation, expression vectors, cloning vectors, shuttle vectors, etc. which can include, but are not limited to, the following vectors or their derivatives: human, animal, or plant viruses such as vaccinia virus, adenovirus, cauliflower mosaic virus (CaMV), geminivirus, brome mosaic virus, and tobacco mosaic virus; insect viruses such as baculovirus; yeast vectors; bacteriophage vectors (e.g., lambda), and plasmid (e.g. the Ti plasmid of *Agrobacterium tumefaciens*) and cosmid DNA vectors, to name but a few. Selection of the appropriate vector will be dictated by the target cells, desired expression mode (e.g., transient expression versus permanent integration into the genome versus independently replicating vectors will cause one of skill in the art to select different vectors), and ease of recombinant manipulation. In some circumstances, one of skill in the art would use a shuttle vector that is functional in at least two organisms so that the nucleic acid may be manipulated in one organism and then transferred into the other.

For example, vectors can be engineered which allow for the production of transgenic plants which express a HecA-like hemagglutinin. Vectors can also be created which allow for the expression of a HecA-like hemagglutinin in a plant endophyte.

Transgenic Plants

One approach described herein involves production of a transgenic plant that expresses anti-microbial peptides in hopes of eliminating or killing *Xylella fastidiosa* cells en planta. The hemagglutinin-mediated resistance described herein more specifically targets *Xylella fastidiosa* and offers a transgenic resistance approach that may be more acceptable to regulatory agencies and the public. For some plants, if the hemagglutinin gene is expressed at sufficient levels in rootstocks, such rootstocks may provide systemic protection to existing cultivars grafted on engineered rootstocks. One example of a plant which can be modified to express a HecA-like hemagglutinin is grapevines. Other examples of plants include but are not limited to: citrus, peach, plum, oleander, elm, sycamore, oak, maple, alfalfa, almond, pear, coffee, mulberry, sedges, periwinkle, and hemlock Introduction of the selected construct into plants is typically achieved using standard transformation techniques. The basic approach is to: (a) clone the construct into a transformation vector, which (b) is then introduced into plant cells by one of a number of techniques (e.g., electroporation, microparticle bombardment, *Agrobacterium* infection); (c) identify the transformed plant cells and regenerate whole plants from the identified plant cells, and (d) select progeny plants containing the introduced construct.

Preferably all or part of the transformation vector will stably integrate into the genome of the plant cell. That part of the transformation vector which integrates into the plant cell and which contains the introduced recombinant sequence may be referred to as the recombinant expression cassette.

Selection of progeny plants containing the introduced transgene may be made based upon the detection of the recombinant HecA-like hemagglutinin encoding gene in transgenic plants, upon the detection of the recombinant HecA-like hemagglutinin protein-coding sequence or upon enhanced resistance to a chemical agent (such as an antibiotic) as a result of the inclusion of a selectable marker gene incorporated into the transformation vector.

Successful examples of the modification of plant characteristics by transformation with cloned nucleic acid sequences are replete in the technical and scientific literature. Selected examples, which serve to illustrate the knowledge in this field of technology include: U.S. Pat. No. 5,571,706 ("Plant Virus Resistance Gene and Methods"); U.S. Pat. No. 5,677,175 ("Plant Pathogen Induced Proteins"); U.S. Pat. No. 5,510,471 ("Chimeric Gene for the Transformation of Plants"); U.S. Pat. No. 5,750,386 ("Pathogen-Resistant Transgenic Plants"); U.S. Pat. No. 5,597,945 ("Plants Genetically Enhanced for Disease Resistance"); U.S. Pat. No. 5,589,615 ("Process for the Production of Transgenic Plants with Increased Nutritional Value Via the Expression of Modified 2S Storage Albumins"); U.S. Pat. No. 5,750,871 ("Transformation and Foreign Gene Expression in *Brassica* Species"); U.S. Pat. No. 5,268,526 ("Overexpression of Phytochrome in Transgenic Plants"); U.S. Pat. No. 5,780,708 ("Fertile Transgenic Corn Plants"); U.S. Pat. No. 5,538,880 ("Method for Preparing Fertile Transgenic Corn Plants"); U.S. Pat. No. 5,773,269 ("Fertile Transgenic Oat Plants"); U.S. Pat. No. 5,736,369 ("Method for Producing Transgenic Cereal Plants"); U.S. Pat. No. 5,610,049 ("Methods for Stable Transformation of Wheat"); U.S. Pat. No. 6,235,529 ("Compositions and Methods for Plant Transformation and Regeneration"); Iocco et al. (2001); and Mezzetti et al. (2002) all of which are hereby incorporated by reference in their entirety. These examples include descriptions of transformation vector selection, transformation techniques and the construction of constructs designed to express an introduced transgene.

The transgene-expressing constructs of the present invention may be usefully expressed in a wide range of plants which are susceptible to diseases caused by *Xylella fastidiosa*.

Methods for the transformation and regeneration of monocotyledonous and dicotyledonous plant cells are known, and the appropriate transformation technique will be determined by the practitioner. The choice of method will vary with the type of plant to be transformed; those skilled in the art will recognize the suitability of particular methods for given plant types. Suitable methods may include, but are not limited to: electroporation of plant protoplasts; liposome-mediated transformation; polyethylene glycol (PEG-mediated transformation); transformation using viruses; micro-injection of plant cells; micro-projectile bombardment of plant cells; vacuum infiltration; and *Agrobacterium*-mediated transformation. Typical procedures for transforming and regenerating plants are described in the patent documents listed above.

Following transformation, transformants are preferably selected using a dominant selectable marker. Typically, such a marker will confer antibiotic or herbicide resistance on the seedlings of transformed plants, and selection of transformants can be accomplished by exposing the seedlings to appropriate concentrations of the antibiotic or herbicide. Suitable markers include, without limitation, those genes coding for resistance to the antibiotic spectinomycin or streptomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance. After transformed plants are selected and grown the plant can be assayed for expression of recombinant HecA-like hemagglutinin. Examples of plants which can be transformed to express a HecA-like hemagglutinin gene include but are not limited to grapevine, citrus, peach, plum, oleander, elm, sycamore, oak, maple, alfalfa, almond, pear, coffee, mulberry, sedges, periwinkle, and hemlock.

Transgenic Plant Endophytes

In another embodiment, levels of *Xylella fastidiosa* (Xf) hemagglutinin (HA) protein may be increased in xylem fluids of plants by introducing and expressing a cloned *Xylella fastidiosa* HecA-like hemagglutinin gene in a bacterial/fungal endophyte that colonizes plant tissues such as xylem tissues.

Endophytes There are a number of bacterial endophytes that can colonize and multiply to reasonably high populations in the xylem of plants. Some of these endophytes such as *Pseudomonas* and *Agrobacterium* species are well studied and transformation systems for introducing any gene into these species are numerous and well documented. Genetically engineered bacterial endophytes could introduce significant levels of HecA-like hemagglutinin directly into the xylem fluids where *Xylella fastidiosa* resides and causes disease and possibly slow their colonization as described for transgenic grapevines expressing a HecA-like hemagglutinin.

Another strategy for elevating levels of *Xylella fastidiosa* HecA-like hemagglutinin in xylem fluids would be to introduce and express a cloned *Xylella fastidiosa* HecA-like hemagglutinin gene in an avirulent strain of *Xylella fastidiosa*. Such engineered avirulent strains of *Xylella fastidiosa* could be introduced into plants such as grapevines. This strategy could slow or inhibit the initiation or progression of Pierce's disease by virulent stains of *Xylella fastidiosa*.

Also identified are other endophytes, such a *Bacillus* and a *Cellulomonas* spp. that may be more difficult to genetically manipulate. However, these two endophytes are naturally antagonistic to *Xylella fastidiosa* and they have provided some level of protection against the development of Pierce's disease when they are inoculated into grapevines that are later exposed to *Xylella fastidiosa*-infectious insect vectors. (D. Darjean, Chemical and Biological strategies for the management of *Xylella fastidiosa*, the causal agent of Pierce's disease of grapes, Ph.D. dissertation, University of California, Davis.) If HecA-like hemagglutinin could be expressed by a xylem-colonizing, *Xylella fastidiosa*-antagonistic bacterial endophyte, the HecA-like hemagglutinin may aggregate and immobilize the *Xylella fastidiosa* cells and make them more susceptible to inhibitory substance(s) produced by these endophytic antagonists. It is also possible that endophyte expressed HecA-like hemagglutinin could act as an adhesion molecule that would associate *Xylella fastidiosa* cells and the antagonistic endophyte, thus potentially providing better suppression of *Xylella fastidiosa* populations in grapevines and possibly provide a control for diseases caused by *Xylella fastidiosa* such as Pierce's disease.

Any bacterial or fungal endophyte which can colonize plant tissues can be used. Examples of such fungal endophytes include *Eutypella aequlinearis* and *Diatrypella* spp.

Introduction of a HecA-like hemagglutinin into a plant endophyte Transformation of endophytes is well known in the art. Any endophyte which can be used to express a HecA-like hemagglutinin in a plant may be used. The following reference describes one method of genetic engineering of bacterial endophytes: Simon R, Priefer U, Pühler A. A broad host range mobilization system for in vivo genetic engineering: transposon mutagenesis in Gram negative bacteria. *Bio/Technology.* 1983; 1:784-791, which is hereby incorporated by reference in its entirety.

One example of an endophyte which can be engineered to express a HecA-like hemagglutinin is *Agrobacterium*. Transformation of *Agrobacterium* is well known in the art. One transformation method which can be used is the freeze thaw method, in which a suspension containing a DNA construct and *Agrobacterium* cells grown in culture is frozen. After thawing, the transformed cells can be selected with the antibiotic whose resistance is carried in the DNA construct used. These transgenic endophytes can then be introduced into plants where they will express the HecA-like hemagglutinin, thereby conferring resistance to disease caused by *Xylella fastidiosa*.

Another endophyte which can be transformed with a HecA-like hemagglutinin is *Pseudomonas*. Methods of transformation of *Pseudomonas* are well known in the art. One example of a method of transforming *Pseudomonas* is by electroporation.

Another endophyte which can be transformed with a HecA-like hemagglutinin is avirulent *Xylella fastidiosa*. Methods of transformation of *Xylella* are well known in the art. One example of a method of transforming *Xylella* is by electroporation.

Fungal endophytes can be transformed using a calcium chloride/polyethylene glycol (PEG) protocol as described in the following reference: Malardier L, Daboussi M J, Julien J, Roussel F, Scazzocchio C, Brygoo Y., Cloning of the nitrate reductase gene (niaD) of *Aspergillus nidulans* and its use for transformation of *Fusarium oxysporum*. *Gene.* 1989 May 15; 78(1):147-56, which is hereby incorporated by reference in its entirety.

The following reference provides a review of genetic engineering of fungal endophytes: B. Chai and M. B. Sticklen, 1998. Applications of biotechnology in turfgrass genetic improvement. Crop Science 38: 1320-1338, which is hereby incorporated by reference in its entirety.

Introduction of endophyte expressing a HecA-like hemagglutinin into plants Any method which is capable of introducing endophytes expressing a HecA-like hemagglutinin into a plant may be used.

The transgenic endophyte-infected plants may be established initially by methods which involve directly incorporating transgenic endophytes into seedlings or other appropriate plant tissues of naturally occurring plants. Once the plant tissues are infected, they can be used for the development of plants having endophyte-enhanced performance characteristics, namely, the resistance to disease caused by *Xylella fastidiosa*. These plants can then be used in more traditional plant-breeding procedures for producing further improved varieties.

Selected plants can be infected with transgenic endophytes as seedlings, as callus tissue, as plantlets derived from single meristems or as somatic embryos, using methods known to those of skill in the art of plant tissue culture. Methods of culturing plant tissues are well known to modern plant biologists.

Plant tissues may be inoculated with transgenic endophytes by placing the endophyte into a direct wound or cut made in the plant tissue. Where the plant tissues to be inoculated are plantlets from germinated seedlings or developed from plant meristems, the cut may be made directly into the stem of the plant. The inoculation can be carried out by placing a small amount of an endophyte directly on or into the cut. Likewise callus tissue may be cut and the endophyte applied directly to the wound.

Inoculated plant tissues are allowed to heal, and the tissues are allowed to develop into plants which can be further cultivated by methods appropriate for the tissue type initially inoculated. If plantlets have been inoculated, they can be grown in sterile culture for six to eight weeks before they are transferred to greenhouse and transplanted into soil.

If callus tissue has been inoculated with a transgenic endophyte, the tissue can be transferred into medium to allow the development of somatic embryos and plantlets.

Inoculated plants may be removed from the sterile growth medium using forceps and transferred into (non-sterile) greenhouse potting mixture. The plantlets may be grown in potting mix for 4 to 6 weeks until they are of sufficient size that a piece of the stem material can be excised and checked under the microscope for the presence of the endophyte.

Plants

In another embodiment, the present invention is directed to transgenic plants expressing a HecA-like hemagglutinin from Xylella fastidiosa, and plants containing transgenic endophytes which express a HecA-like hemagglutinin.

Plants which find use in the invention are those which are susceptible to infection by Xylella fastidiosa, for example grapevines, citrus, peach, plum, oleander, elm, sycamore, oak, maple, alfalfa, almond, pear and coffee. Also contemplated are other plants such as mulberry, sedges, periwinkle, and hemlock. Any plant which is discovered to be subject to disease caused by Xylella fastidiosa may be used in the invention. Both monocotyledonous and dicotyledonous plants may be used.

Uses

The transgenic plants expressing a HecA-like hemagglutinin and the plants harboring a plant endophyte expressing a HecA-like hemagglutinin will be more resistant to diseases caused by Xylella fastidiosa infection compared to wild type plants and plants not harboring an endophyte expressing a HecA-like hemagglutinin. Recombinant HecA-like hemagglutinin is therefore useful for expression in plants that are susceptible to Xylella fastidiosa infection. Such plants will innately inhibit Xylella fastidiosa infection without addition of antibiotics or exogenously added chemicals.

In addition, nucleic acids of the invention will be useful in generating the transgenic plants of the present invention. The HecA-like hemagglutinin encoding genes (such as HxfA and HxfB) may be used to identify such genes in other species. In addition, the HecA-like hemagglutinin encoding nucleic acid will be useful in designing probes that may be used to detect HecA-like hemagglutinin encoding nucleic acid expression levels and specific variants of HecA-like hemagglutinin genes. Such probes may be useful in breeding plants with particular HecA-like hemagglutinin genes or expression patterns.

Transformation or transfection of prokaryotic or eukaryotic host cells with the nucleic acid of the HecA-like hemagglutinin gene will be useful in expressing, amplifying, modifying, and transforming the HecA-like hemagglutinin gene into plants. The primers and vectors of the invention will be useful for the same purposes. Modification of the HecA-like hemagglutinin encoding nucleic acid and the HecA-like hemagglutinin amino acid sequence may entail truncation, mutagenesis, deletions, additions, fusions, or other alterations of various parts of the gene or protein in order to change its activity, thereby altering or retaining the activity of the HecA-like hemagglutinin protein. Such mutations, deletions, substitutions, additions, and fusions of the HecA-like hemagglutinin encoding nucleic acid and protein are within the scope of the invention. HecA-like hemagglutinin encoding nucleic acid fusions may include the use of heterologous promoters to alter the regulation of the HecA-like hemagglutinin gene.

In addition, the nucleic acids of the invention will be useful in generating plant endophytes which express a HecA-like hemagglutinin.

The following examples are provided to illustrate further embodiments of the invention.

Example 1

Pathogenicity Assays and Identification of Xylella fastidiosa Hypervirulent Mutants Materials and Methods Bacterial strains, growth conditions and primers. The PD Xylella fastidiosa strain Temecula was isolated and stored as previously described (Guilhabert et al., 2001). For all experiments, the wild type and Tn5 Temecula Xylella fastidiosa mutants were grown at 28° C. in PD3 medium (Davis et al., 1981) with or without 5 □g/ml of kanamycin. For the growth, aggregation, adhesion and colony morphology assays, Xylella fastidiosa cells, previously seeded on PD3 plates, were harvested, transferred into two ml of PD3 liquid medium and adjusted to $OD_{600}$=0.25 ($10^8$ cells $ml^{-1}$). The adjusted Xylella fastidiosa suspension was diluted 1:100 with fresh PD3 medium, and used for all growth kinetics, adhesion and colony morphology assays. Culture volumes did not exceed 20% of the capacity of the flasks or tubes to ensure adequate aeration of the culture. The cultures were established in duplicate. All the primers used in this study are presented in Table 1.

Random Transposon Mutagenesis

Electrocompetent Xylella fastidiosa Temecula cells were prepared as previously described (Guilhabert and Kirkpatrick, 2003). The Xylella fastidiosa Temecula strain was mutagenized using the transposome protocol described (Guilhabert et al., 2001). A random insertion library of 1,000 Tn5 Xylella fastidiosa mutants was generated.

Pathogenicity assays. Each Tn5 Xylella fastidiosa mutant was individually innoculated into Chardonnay, Chenin Blanc and Thompson seedless grapevines to assess pathogenicity. All 1,000 Tn5 Xylella fastidiosa mutants in Chardonnay were screened for altered symptom development. This screen identified 7 Xylella fastidiosa Tn5 mutants that showed a pronounced hypervirulence phenotype 21 weeks after inoculation (i.e. grapevines inoculated with these Tn5 mutants developed more severe disease symptoms than did vines inoculated with the wild type Temecula strain). In order to confirm their hypervirulence phenotype, the 7 mutants and wild type controls were retested in a similar matter for i) earlier symptom development ii) more severe symptom development during a period of 32 weeks and iii) earlier death of the inoculated grapevines. The disease progression of the 7 mutants and wild type controls was performed in three plants each of Chardonnay, Chenin Blanc and Thompson seedless grapevines (9 plants total for each mutant). The Xylella fastidiosa 1792 mutant strain was tested twice in a similar manner in three Chardonnay grapevines (6 plants total).

Results

In order to understand the mechanisms by which Xylella fastidiosa causes plant disease, a random transposition approach was taken to disrupt genes potentially involved in Xylella fastidiosa virulence and/or movement in grapevine plants. Seven putative hypervirulent Xylella fastidiosa mutants (i.e. grapevines inoculated with these Tn5 mutants developed more severe disease symptoms than did the wild type Temecula strain 21 weeks after inoculation), out of 1,000 that were screened, were selected and retested by inoculating three additional Chardonnay as well as three Chenin Blanc and Thompson seedless grapevines. All of the 7 Tn5 *Xylella fastidiosa* hypervirulent mutants tested showed i) earlier symptom development, ii) higher disease score over a period of 32 weeks and iii) earlier death of the inoculated grapevines than the wild type cells when inoculated into all grapevines (FIG. 2); thus demonstrating that the hypervirulence phenotype is correlated with earlier symptom development and earlier vine death in multiple *Vitis vinifera* cultivars.

Example 2

Identification of Genes Associated with the Hypervirulent Phenotype and Sequence Analyses Materials and Methods Identification of mutated genes and sequence analysis. All the *Xylella fastidiosa* mutants are described in Table 1.

After assessing pathogenicity in greenhouse-grown grapevines (see below), the site of Tn5 insertion of the mutants with enhanced virulence (hypervirulent *Xylella fastidiosa* mutants) was identified by a two-step procedure. The chromosomal region flanking the Tn5 element was first amplified using an oligonucleotide, Poforw that binds specifically to the transposon sequence in combination with a degenerate primer, Arb1 that anneals to sequences flanking the Tn5 insertion. Then, following PCR amplification, direct sequencing was accomplished using a second oligonucleotide, kan-2 fp-1 that primes the PCR fragment downstream of Poforw near the right border of the transposon (Chun et al., 1997; Hermann et al., 2000). One colony of each Tn5 *Xylella fastidiosa* mutant was transferred into 10 µl of de-ionized water and 3 µl of the suspension was used as template in the PCR reaction. All PCR reactions were conducted with conditions described by Hermann et al., 2000, using a Taq DNA polymerase (Promega, Madison, Wis.) diluted in a TaqStar™ antibody (BD Biosciences Clontech, Palo Alto, Calif.). Only the first step of a modified two-step PCR protocol was used (Chun et al., 1997). Briefly, the first 12 cycles included an annealing step of 30 sec, initially at 36° C., then increasing 1° C. per cycle; the last 25 cycles included a primer-annealing step of 30 sec at 65° C. After amplification, the PCR products were purified using the "Qiaquick PCR purification kit" (Qiagen, Valencia, Calif.) and were sequenced in a "2X" Big Dye Terminator sequencing reactions (Applied Biosystems, Foster City, Calif.), using the outward primer kan-2 fp-1 by the Division of Biological Sciences DNA sequencing facility at UC Davis.

An additional hemagglutinin-like mutant strain, Xf1246 was also identified by sequencing the insertion sites of the random mutants from the library described above.

Six of the Tn5 insertion sites were confirmed using as forward primers kan-2 fp-1 and kan-2 rp-1 that bind close to the right and left borders of the transposome, respectively, and reverse primers derived from the sequences obtained in the mutated ORF. The identity of the two putative hemagglutinin mutated genes, xf2118 and xf1246 was further confirmed by Southern Blot analysis (see below). All PCR reactions were conducted and cycled with standard conditions (Smart et al., 1996). The 35 cycles of PCR included an annealing step of 1 minute at 58° C. The resulting PCR products were sequenced to further confirm the location of the Tn5 insertion sites.

DNA sequences were analyzed with the program Bioedit version 5.0.6 (Tom Hall, N.C. State University, Department of Microbiology) and database searches were performed with the BLAST program accessed through the National Center for Biotechnology Information (NCBI) website (Altschul et al., 1990). GenBank comparisons in the NCBI conserved domain were performed to identify conserved domains in hypothetical proteins. This was accomplished using tools available at the NCBI Structure group website on the Internet, which maintains the Molecular Modeling Database of macromolecular 3D structures. The protein alignments were performed using the CLUSTALW method, which is described in Thompson et al., 1994, and on the Internet at the website of the European Bioinformatics Institute.

Results

In order to determine the identity of the mutated gene, the transposon insertion sites of the mutants were identified using a combination of PCR and sequencing (Table 1). Six of the mutated genes corresponded to genes with assignable functions and one gave a significant match with a hypothetical conserved gene. Southern blot analysis of the hypervirulent *Xylella fastidiosa* mutants showed that the clones contained a single transposon insertion (data not shown). Regions flanking the Tn5 mutated gene sequences also were the same as the sequences of their respective regions in the wild type *Xylella fastidiosa* Temecula strain; thus confirming the position of the Tn5 insertion in the hypervirulent mutants.

One hypervirulent Tn5 mutant was disrupted in PD2118, which putatively encodes a hemagglutinin-like secreted protein. A second mutant was disrupted in PD1542, which putatively encodes a dolichol-phosphate mannosyltransferase lipopolysaccharide, dmt, which might be involved in LPS biosynthesis by adding a sugar onto the O-polysaccharide chain. The five other Tn5 mutants were disrupted in PD1198, PD0218, PD0681, PD0875 and PD1244 genes, which putatively encode for a ferric enterobactin receptor bfe A, a serine protease, psp B, a glucose/galactose transporter, glu P, a coenzyme F390 synthetase, paa K and a hemagglutinin-like hypothetical protein, respectively (Table 1).

A number of large exoproteins, including hemagglutinins, are secreted by a two-partner secretion (TPS) pathway (Jacob-Dubuisson et al., 2001). Adhesins secreted through the TPS pathway (Tps proteins), share similar "secretion domains" despite their limited overall sequence similarities (Jacob-Dubuisson et al., 2001). The secretion domain includes a 110-amino acid (aa) conserved region in the N-proximal region (Schonherr et al., 1993). The Tsp secretion domains are conserved in HecA, a hemagglutinin protein in *E. chrysanthemi* (GenBank accession number AF501263; Rojas et al., 2002) The first 200-aa were analyzed in the N-proximal region of the seven gene products that were annotated as hemagglutinin-like proteins in the PD genome sequence (Van Sluys et al., 2003). The putative seven *Xylella fastidiosa* hemagglutinin proteins were aligned with the hemagglutinin HecA of *E. chrysanthemi* (FIG. 3).

Although the three *Xylella fastidiosa* hemagglutinin-like products PD2116, PD2110 and PD0988 showed 34%, 35% and 26% amino acid identity, respectively with a putative hemagglutinin-related protein from *Ralstonia solanaceraum* (GenBank accession number Np_522632.1), comparison of their N-proximal 250 aa sequences did not reveal the previously described Tps secretion domains (FIG. 3). The putative hemagglutinin-related protein from *Ralstonia solanaceraum* mentioned above did not contain the Tps secretion domains. The PD *Xylella fastidiosa* product PD0986, annotated as a hemagglutinin-like protein (Van Sluys et al., 2003), did not possess any homology with putative hemagglutinin or adhesin proteins from other bacteria.

Further amino acid sequence analyses revealed that the Tps secretion domains were only conserved in the last three *Xylella fastidiosa* hemagglutinin-like genes PD2118, PD1792 and PD1246 (FIG. 3). Interestingly, PD gene PD1246 has a frameshift/point mutation in its sequence (Van Sluys et al., 2003); thus PD1246 is most likely not functional in the Temecula strain. In addition to the presence of the Tps secretion domains in their sequence, PD2118 and PD1792 gene products also possess 27% and 37% amino acid identities, respectively with the HecA protein from *E. chrysanthemi*. Therefore, the PD2118 and PD1792 gene products were named HxfA and HxfB, respectively (H indicates hemagglutinin, xf, *Xylella fastidiosa*, A and B for the two first hemagglutinins described in *Xylella fastidiosa*).

HxfB was cloned in *E. coli*, disrupted by Tn5 mutagenesis, and the disrupted gene introduced back into *X. fastidiosa*. The introduced construct replaced the wild type HxfB gene by homologous recombination (see Example 5).

GenBank comparisons of the hemagglutinin-like hypothetical PD1244 ORF, identified in the mutant study (see above), revealed homology only with genes in various *Xylella fastidiosa* genome sequences. The PD1244 product had 82% and 74% amino acid identity with the putative hemagglutinin-like products Xf2196 from the CVC and PD2116 from the PD strain of *Xylella fastidiosa*, respectively (Simpson et al., 2000 and Van Sluys et al., 2003). However, putative PD1244 gene predicts a 79-aa protein, whereas genes Xf2196 and PD2116 predict a 3442-aa and 439-aa protein, respectively. Therefore, the amino acid identity between gene products PD1244, Xf2196 and PD2116 is based only on a small region of the putative proteins. In contrast to Xf2196, the Tsp secretion domains noted in HecA were not identified in PD1244 or PD2116 products (FIG. 3). No conserved domains were identified in PD1244 protein using the NCBI conserved domain database.

Example 3

Hypervirulent Mutations Altered *Xylella fastidiosa* Growth Rate and Increased Movement in Planta Materials and Methods

*Xylella fastidiosa* growth curves and en planta bacterial population determinations. Growth curve determinations were performed in 15 ml polystyrene tubes containing 3 ml of PD3 medium. A total of 14 tubes were prepared for the wild type and each Tn5 mutant, so as to allow destructive sampling of two tubes at every sampling time. Two independent growth curve determinations were performed. Due to the aggregate nature of *Xylella fastidiosa* liquid cultures, immediately after inoculation and after 2, 4, 6, 8, 12 and 16 days, the cultured cells were completely dispersed using a tissue homogenizer (Heidolph RzR 50) and the cell growth was monitored by measuring turbidity at $OD_{600}$ nm. The doubling time of the bacterial populations was calculated using a standard equation (Madigan et al., 1970).

The bacterial populations (number of cells per gram of petiole tissue) of the *Xylella fastidiosa* wild type and Tn5 mutants inoculated into Chardonnay vines were determined in the following manner: 14 weeks after inoculation, petiole tissues from each vine inoculated with either Tn5 mutant or wild-type *Xylella fastidiosa* cells were harvested at the point of inoculation and 25 centimeters above the point of inoculation. Petiole tissues were surface sterilized (1 min in 10% sodium hypochlorite and 1 min in 80% ethanol), rinsed three times in sterile de-ionized water and ground in 2 ml of sterile PBS buffer using a grinding machine (Biorega AG, Switzerland). Serial dilutions were prepared and 3 replicates of 10 μl were plated on PD3 agar medium with or without kanamycin. After incubating 7-10 days at 28° C., the number of bacteria was quantified.

Results

Figure 5:
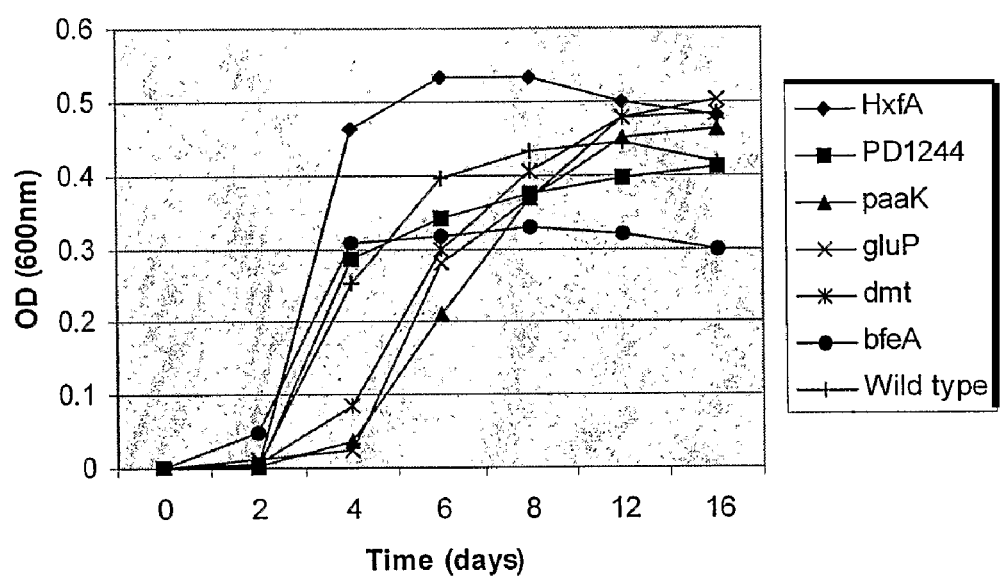
FIG. 5 shows the growth of *Xylella fastidiosa* wild type and Tn5 mutants in liquid PD3 medium. Growth curves were determined based on $OD_{600}$. Data are average of two experiments with two repetitions each.

Growth curves of the Tn5 mutants and wild type *Xylella fastidiosa* strain showed that all the hypervirulent mutants reached the exponential and stationary phase in a manner similar to the wild type *Xylella fastidiosa* strain (FIG. 5).

The doubling time of Tn5 mutants and wild type *Xylella fastidiosa* strain was also determined. The doubling time of the wild type *Xylella fastidiosa* strain was 0.5 day. In contrast, the doubling times of 4 of the Tn5 mutants were longer than the wild type strain, whereas the doubling time of hxfA (PD2118) and PD1244 mutants was faster than the wild type strain (Table 2). The doubling time of PD1198 *Xylella fastidiosa* mutant was not significantly different from the wild type strain.

In order to evaluate possible mechanisms that could explain the hypervirulence phenotype, bacterial populations and movement in infected grapevines was assessed for the seven mutants and wild type strain. The hypervirulent mutants moved faster in inoculated grapevines than the wild type at 25 cm above the point of inoculation 12 weeks post inoculation. In contrast, the population of the hypervirulent mutants was not significantly different than the wild type at the point of inoculation (Table 3). The data suggests that hypervirulent cells colonize more rapidly grapevine tissue than wild type cells.

Example 4

HxfA is Involved in Cell-Cell Aggregation In Vitro and in Planta

Materials and Methods

Surface attachment, cell-cell aggregation and colony morphology assays. The Tn5 mutants or wild type *Xylella fastidiosa* cells were grown in 25 ml of PD3 broth medium in 125 ml glass Erlenmeyer flasks on an orbital shaker at 120 rpm to visualize the formation of bacterial cell clumps within the liquid medium and the formation of aggregated cells that attached to the inside of the flask (Marques et al., 2002).

Additional surface attachment and aggregation assays were performed in polystyrene (15 ml; Falcon 2051 tubes, Becton & Dickinson Labware), polypropylene (5 ml; Falcon 2063 tubes, Becton & Dickinson Labware) and borosilicate glass (10 ml) tubes containing PD3 medium. The cultures were incubated at 28° C. in a vertical position without shaking for 10 days. Attachment on the surface walls of the tubes was assessed by a crystal violet staining method (Espinosa-Urgel et al., 2000 and Leite et al., 2004). Briefly, after the incubation period, the PD3 medium was discarded and a 1% (wt/vol) solution of crystal violet was added to each tube and rinsed with de-ionized water. The remaining stain was eluted from the bacterial ring by ethanol. The absorbance of the ethanol-crystal violet solution was measured at 600 nm.

The cell-cell aggregation assay was performed as described by Burdman et al., (2000) and Leite et al., (2004). After 10 days of static incubation, the *Xylella fastidiosa* cultures were gently agitated and the aggregates allowed to settle for 20 min. The turbidity of the remaining upper culture medium, composed mostly of dispersed cells was measured using a spectrophotometer at 540 nm. The culture medium was returned to the original tube, the aggregate masses were dispersed using a tissue homogenizer (Heidolph RzR 50) for 1 min and the total cell culture was measured (ODt). Relative percentage of aggregated cells was estimated as follows: % aggregated cells=(ODt−ODs)/ODt×100 (Burdman et al., 2000).

The colony morphology of the wild type or mutant cells was assessed by plating one hundred μl of a 10⁸ cfu/ml solution onto 2 PD3 plates (4 plates total). Aberrant colony morphology of mutants was compared to wild type after 10 days growth on PD3 solid medium at 28° C.

Scanning electron microscopy (SEM). The wild type and mutant cells of *Xylella fastidiosa* that were inoculated into grapevines or grown in PD3 broth were examined using scanning electron microscopy (SEM). Petiole samples were collected from symptomatic grapevines three months after inoculation. Petioles sections and bacterial aggregates, harvested by centrifugation from *Xylella fastidiosa* liquid cultures grown in a glass Erlenmeyer flask, were fixed overnight in a 2.4% glutaraldehyde, 0.3% paraformaldehyde solution. Fixed samples were then dehydrated by increasing concentrations of ethanol, critically-point dried in a Tousimis Samdri-780A, placed on aluminum specimen mounts with carbon conductive tabs, and sputter-coated with gold using a Denton Vacuum Desk II cold sputter-etch unit. The morphology of the mutant or wild type *Xylella fastidiosa* aggregates grown in grapevines or grown in PD3 broth was observed at 5-12 khz with a Hitachi S-3500N SEM and images were recorded digitally.

Results

To evaluate whether the hypervirulence phenotype affected cell-cell attachment, the ability of each hypervirulent mutant to aggregate in culture was investigated. Cell-cell aggregation of each mutant was first visually assessed in 125 ml glass Erlenmeyer flasks placed on an orbital shaker. The wild type *Xylella fastidiosa* strain and 6 of the Tn5 mutants formed large aggregates when grown in vitro (FIG. 6A, Table 2). In contrast, the hxfA mutant was impaired in its ability to form cell-cell aggregates in liquid culture (FIG. 6B, Table 2).

The colony morphology of wild type, HxfA and HxfB cells were examined on solid medium. HxfA and HxfB mutants exhibited a homogenous distribution of cells, forming a continuous lawn of cells, whereas the wild type grew in separate clumps composed of small and medium-size individual colonies (FIGS. 6C and D); thus further confirming the inability of HxfA cells to self-aggregate.

An optical density assay (Burdman et al., 2000) was used to quantify the effect of the HxfA mutation on cell-cell aggregation. This assay further confirmed that cell-cell aggregation of HxfA mutant was decreased (Table 4).

Figure 6:
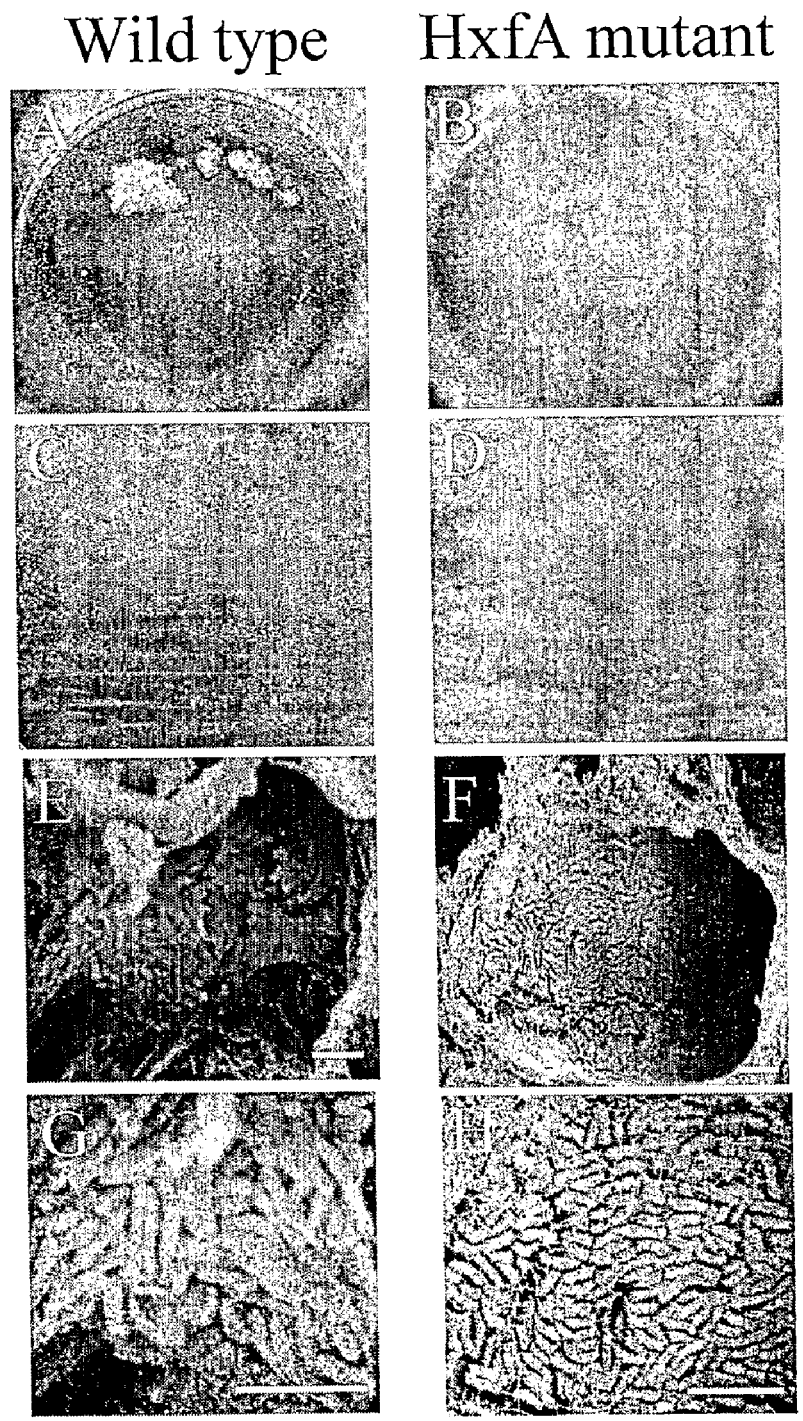
FIG. 6 shows HxfA-dependent aggregation of *Xylella fastidiosa* cells in vitro and in planta. Panels A, C, E and G show *Xylella fastidiosa* wild type cells. Panels B, D, F and H show *Xylella fastidiosa* hxfA mutant cells. Panels A and B show wild type and hxfA mutant cells, respectively, inoculated into PD3 medium in a 125 ml flask and placed on a shaker. The degree of self-aggregation was visualized after 10 days of incubation. Panels C and D show wild type and hxfA mutant cells, respectively, plated onto PD3 medium plates. The colony morphology was examined after 10 days of incubation. Panels E and F show wild type and hxfA cells in xylem vessels. Note the lack of a three dimension array in the HxfA mutant compare to wild type. Panels G and H show higher magnification of wild type and hxfA cells in a biofilm. Note the wild type cells typically aggregated together side to side while the hxfA mutant cells did not aggregate in this manner. Scale bar equivalent to 5 microns in every panel.
Figure 7:
FIG. 7 shows a model of possible mechanisms involved in *X. fastidiosa* adhesion to xylem vessels of grapevines. Rods are *X. fastidiosa* cells. A shows how *Xylella fastidiosa* bacteria attach to the surface using most likely non-fimbrial adhesins, other than hemagglutinins (Tables 4; Feil et al., 2003); B shows how HxfA, HxfB and other adhesins mediate secondary contact between *Xylella fastidiosa* cells allowing in C, which shows microcolony formation. Based on the results, hemagglutinins appear to be important mediators for cell-cell aggregation; D shows bacterial cells finally aggregating to each other via hemagglutinins HxfA and HxfB, fimbriae and exopolysaccharides (EPS) to form matured biofilms within the xylem vessels (Tables 2 and 4, FIG. 6; Feil et al., 2003).

The aggregates of wild type and hxfA mutant cells grown in PD3 medium and in planta were observed by scanning electron microscopy. Wild type cells, grown in vitro were aggregated together typically by cell-cell contact along the length of the cells (data not shown). The hxfA mutant cells did not appear to be aggregated in such a manner (data not shown). This result was further observed in planta (FIG. 6). FIGS. 6F and H shows that HxfA cells did not form large clumps in the plants but rather hxfA cells typically formed a mono-layer of cells on the surface of the xylem vessels. In contrast, wild type cells formed a multiple-layer of cells that clearly aggregated to each others (FIGS. 6E and G).

Example 5

Cloning of the hemagglutinin gene, HxfB (PD1792). The PD1792 gene of a grapevine strain causing Pierce's disease (PD; *Xylella fastidiosa* Temecula isolate; Van Sluys et al., 2003) was amplified using the Expand Long Template PCR system (Roche, Mannhein, Germany) with primers PD1791 rev (5' GGAGCAAGACAGTCGCGGAT 3' (SEQ ID NO: 9)) and PD1793 forw (5' GATATCGTGAACGATTGCCGCCT 3' (SEQ ID NO: 10)), anneal to sequences that flank the ORF encoding the PD1792 gene. Briefly, the annealing temperature in both set of cycles was 58° C. and the elongation times in the first and second set of cycle were 4' for 10 cycles and 4'+20" per cycle for 25 cycles, respectively. A PCR product of the expected 10,134 bp-size was obtained.

The PCR product was cloned into the pCR®-XL-TOPO® vector using the TOPO® XL PCR cloning kit (Invitrogen, Carlsbad, Calif.) following the manufacturer recommendations. Cloning of the PD1792 gene was confirmed by sequencing the end of the cloned PCR product using primers, M13 forward and reverse (5' GTTTTCCCAGTCACGA 3'(SEQ ID NO: 11) and 5'CAGGAAACAGCTATGAC 3' (SEQ ID NO: 12), respectively; Invitrogen, Carlsbad, Calif.). The sequencing was performed in a "2X" Big Dye Terminator sequencing reactions (Applied Biosystems, Foster City, Calif.) by the Division of Biological Sciences DNA sequencing facility at UC Davis. The sequences of the cloned PCR product perfectly matched the sequence of the PD1792 gene that is present in the PD genome sequence (Van Sluys et al., 2003).

Example 6

Site-Directed Mutagenesis of hxfB and Confirmation of the Observed hxfA Phenotypes Materials and Methods Site-directed mutagenesis. A 680 bp region of *Xylella fastidiosa* Temecula genome including a small coding sequence of the PD1792 gene was amplified using primers PD1792 rev and PD1792 forw and cloned into the pCR^R 2.1-TOPO vector (Invitrogen, Carlsbad, Calif.). The plasmid was then digested with EcoRI and the PD1792 insert was ligated into EcoRI-digested pUC18 plasmid creating pXF012. Plasmid pXF012 was linearized at the unique restriction site BstBI of the cloned PCR-amplified PD1792 fragment. Two annealed BstBI-adaptors carrying a MfeI restriction site (5'CAATTGACGT 3' (SEQ OD NO: 13)) were ligated in BstBI-digested pXF012. The Tn903 kanamycin resistance gene (Guilhabert et al., 2001) was cloned into pXF012 cut with MfeI to make pXF013. Insert and junction sequences of pXF013 were determined. Two μg of pXF013 plasmid DNA was electroporated into *Xylella fastidiosa*, and transformants were selected as described (Guilhabert et al., 2001). Disruption of the PD1792 locus was confirmed by using the Expand Long Template PCR system (Roche, Mannhein, Germany) with primers PD1791 rev and PD1793 forw, binding to the flanking ORFs of the mutated PD1792 gene. Briefly, the annealing temperature in both set of cycles was 58° C. and the elongation times in the first and second set of cycle were 4' for 10 cycles and 4'+20" per cycle for 25 cycles, respectively. The identity of the PCR product was confirmed by using the restriction enzyme HindIII that cuts only once into the Tn903 kan-2 cassette.

Southern blot analysis of putative *X. fastidiosa* mutants. *Xylella fastidiosa* genomic DNAs were isolated from the mutant strains as described (Zang et al., 1998). Genomic DNAs from the transformants obtained by random mutagenesis were individually digested by the two restriction enzymes, EcoRI and EagI. In order to confirm the identity of the two random hemagglutinin PD2118 and PD1246 mutant strains, their genomic DNAs were also digested with SalI and XmnI. All digested DNAs were electrophoresed, alkali-denatured, and transferred to a nitrocellulose membrane as previously described (Guilhabert et al., 2001). The Tn5 DNA, used as a probe in the hybridization analyses of restriction digested genomic DNAs from the *Xylella fastidiosa* mutants, was PCR amplified and purified (Guilhabert et al., 2001), and 25 ng was labeled with fluorescein dye using the "Gene Images™ random prime labeling module kit" (Amersham Biosciences, UK). Hybridizations and detection were carried out according to the recommendations of the "Gene Images™ CDP-Star™ detection module kit" (Amersham Biosciences, UK). Stringent post-hybridization wash conditions (15 min per wash) were once in 1×SSC-0.1% SDS at 60° C. and once in 0.5×SSC-0.1% SDS at 68° C.

Results

To confirm that hemagglutinins are involved in *Xylella fastidiosa* virulence and cell-cell aggregation, a mutant in the second hemagglutinin identified above, HxfB (PD1792) was generated. The disruption of gene hxfB was confirmed by a long PCR procedure (data not shown). The mutant strain Xf1792 was inoculated twice in three Chardonnay grapevines and it consistently showed i) earlier symptom development, ii) higher disease score over a period of 32 weeks and iii) earlier death of the inoculated grapevines the wild type cells (FIG. 2); thus confirming that hemagglutinins are involved in attenuating *Xylella fastidiosa* pathogenicity. An optical density assay (Burdman et al., 2000) was used as described above to quantify the effects of the HxfB mutation on cell-cell aggregation. This assay further confirmed that hemagglutinins are involved in *Xylella fastidiosa* cell-cell aggregation (Table 4).

Example 7

Sequence Analysis and Subcloning of Putative Cell-Cell Binding Domains of HxfA and HxfB Detailed sequence analysis of HxfA and B using revealed 7 (HxfA, PD2118) and 8 (HxfB, PD1792) domains in the N-terminal region of the proteins that likely represent the Hxf cell-cell binding domains. This analysis was performed by using the Biozon database, developed by researchers at Cornell University, and accessible through the World Wide Web. Three DNA fragments (AD1, AD2 and AD3, all 1.0 to 1.2 kb in size) were identified in each protein that contained 3 or 4 putative binding domains. The AD2 fragment from HxfA and B were most similar in sequence to each other and therefore chosen as a likely marker for both Hxf proteins. AD2 was PCR-amplified, cloned and expressed in a protein fusion vector in *E. coli* and the AD2 fusion protein was purified by affinity chromatography. The fusion protein was injected into rabbits and antibodies against AD2 were produced. The AD2 antibodies are being used to determine the size and cellular location of native Hxf protein in *X. fastidiosa* and PD-affected grapevines. AD2 antibodies and purified AD2 proteins are being used to determine if the AD2 domain is mediating *X. fastidiosa* cell-cell aggregation.

Because the full-length Hxf genes (10.2 kb) is larger than desirable to transform and be expressed in either plants or grapevine endophytes, a 3.5 kb fragment that contains all three putative binding domains (Ad1-AD3) from HxfA and HxfB were PCR-amplified and cloned in *E. coli*. These two 3.5 kb fragments are being transformed into grapevine (*V. vinifera*), tobacco and *Pseudomonas* and *Agrobacterium* endophytes (D. Darjean-Jones, 2004) using appropriate technologies that have been previously discussed. Fusion protein derived from the 3.5 kb fragments are being prepared and used as previously described for Hxf AD2. Using either individual Hxf AD domains or the 3.5 kb to transform plant or endophytes will be more feasible than engineering the full-length Hxf gene and should confer the same desired resistance phenotype.

Tables and Figures

TABLE 1

PCR primers[1] and strains used in this study

| | | Source |
|---|---|---|
| Primers used to sequence the Tn5 insertion sites | | |
| kan-2 fp-1 | ACCTACAACAAAGCTCTCATCAACC (SEQ ID NO: 14) | Epicentre Technology |
| Arb1 | GGCCACGCGTCGACTAGTACNGATAT (SEQ ID NO: 15) | Caetano-Anoles, 1993 |
| Poforw | CTGGCAGAGCATTACGCTGAC (SEQ ID NO: 16) | This study |

| | Primers used to confirm the random Tn5 insertion sites | Used to confirm putative mutated gene | |
|---|---|---|---|
| kan-2 rp-1 | GCAATGTAACATCAGAGATTTTGAG (SEQ ID NO: 17) | | Epicentre Technology |
| kan-2 fp-1[2] | ACCTACAACAAAGCTCTCATCAACC (SEQ ID NO: 18) | | Epicentre Technology |
| 6191.2 forw | TGCAACCACGCTGAACA (SEQ ID NO: 19) | glucose/galactose transporter, gluP | This study |
| 6211.2 rev | GGCATCGACCTCATT (SEQ ID NO: 20) | glucose/galactose transporter, gluP | This study |
| PD0219 forw | GCTGCACTCCAGATTGAACACTGT (SEQ ID NO: 21) | serine protease, pspB | This study |
| PD0217 forw | ACCTACACCTACACCACTGGA (SEQ ID NO: 22) | serine protease, pspB | This study |
| 23531.2 forw | GATCTACCTGCTGTTGC (SEQ ID NO: 23) | hypothetical protein, PD1244 | This study |
| 23551.2 rev | GTGAGGATTATTACGGGTGGTG (SEQ ID NO: 24) | hypothetical protein, PD1244 | This study |
| 22281.2 forw | CGCGTGCTCGCTCTTCAAT (SEQ ID NO: 25) | coenzyme F390 synthetase, paaK | This study |
| 22311.2 rev | TACCGAATGTGGCTTG (SEQ ID NO: 26) | coenzyme F390 synthetase, paaK | This study |
| 11001.2 forw | ATTCACGCTCCATACG (SEQ ID NO: 27) | iron receptor, bfeA | This study |
| 11021.2 rev | ATGTCGAGTCCTGTTGTG (SEQ ID NO: 28) | iron receptor, bfeA | This study |
| 13991.2 rev | AACAGAGTGCTAGTCACC (SEQ ID NO: 29) | mannosyltransferase, dmt | This study |
| 24521.2 forw | ACGACTTGCATAGCAGTAGC (SEQ ID NO: 30) | mannosyltransferase, dmt | This study |

TABLE 1-continued

PCR primers[1] and strains used in this study

Source

Primers used for the site-directed mutagenesis

```
PD1792 rev        TTGTCCTGACGGTCG (SEQ ID NO: 31)         This study
PD1792 forw       CCACCATTGACAACC (SEQ 10 NO: 32)         This study
PD1791 rev        GGAGCAAGACAGTCGCGGAT (SEQ ID NO: 9)     This study
PD1793 forw       GATATCGTGAACGATTGCCGCCT (SEQ ID NO: 10) This study
```

```
Xf mutants   Relevant characteristics              Putative gene function[3]

Xf2118       PD2118[4]::EZ::TN ™<Kan-2>Tnp[5]      hemagglutinin-like secreted protein, HxfA      This study
Xf1542       PD1542::EZ::TN ™<Kan-2>Tnp            mannosyltransferase (Ips biosynthesis), Dmt    This study
Xf1198       PD1198::EZ::TN ™<Kan-2>Tnp            ferric enterobacyin receptor, BfeA             This study
Xf0218       PD0218::EZ::TN ™<Kan-2>Tnp            serine protease, PspB                          This study
Xf0681       PD0681::EZ::TN ™<Kan-2>Tnp            glucose/galactose transporter, GluP            This study
Xf0875       PD0875::EZ::TN ™<Kan-2>Tnp            coenzyme F390 synthetase, PaaK                 This study
Xf1244       PD1244::EZ::TN ™<Kan-2>Tnp            hypothetical protein (hemagglutinin-like)      This study
Xf1792       PD1792::Tn903 kan-2[6]                hemagglutinin-like secreted protein, HxfB      This study
Xf1246       PD1246::EZ::TN ™<Kan-2>Tnp            hemagglutinin-like secreted protein            This study
```

[1] primer sequences are presented 5' to 3'.
[2] primer kan-2 fp-1 was used to sequence and to confirm the Tn5 insertion sites
[3] putative function of ORF based on homology between regions flanking the Tn5 insertion and other Xf gene sequences
[4] identification number of open reading frame (ORF) in PD strain off.
[5] Tn5 derivative (Epicentre Technologies, Madison, WI).
[6] Tn903 kan-2 = kanamycin resistance cassette from EZ::TN$^{TM}$<Kan-2>Tnp (Epicentre Technologies, Madison, WI).

TABLE 2

Physiological properties of the Xf Tn5 mutants and wild type strain

| | Phenotypes | | |
|---|---|---|---|
| | Doubling time | Attachment assay:[c] | |
| Genotype: | (in days):[a, b] | Cell/cell aggregation | Surface attachment |
| Wild type | 0.50 +/− 0.018 | +++ | +++ |
| HxfA | 0.45 +/− 0.005 | − | ++ |
| Dmt | 0.93 +/− 0.01 | +++ | +++ |
| BfeA | 0.48 +/− 0.003 | +++ | +++ |
| PspB | ND[d] | +++ | +++ |
| GluP | 0.88 +/− 0.13 | +++ | +++ |
| PaaK | 1.14 +/− 0.224 | +++ | +++ |
| hypothetical | 0.24 +/− 0.003 | +++ | +++ |

[a] doubling time calculated as described by Madigan et al., 1970.
[b] significant difference indicated in bold; significance defined as $p < 0.01$
[c] frequency of attachment: −, absent; +, low; ++, moderate; +++, high.
[d] Not determined (PspB mutant lost in storage)

TABLE 3

Bacterial populations of Thompson seedless grapevines 12 weeks after inoculation with wild-type or Tn5 Xf cells

| | Xf bacterial populations (cfu/g of tissue) | |
|---|---|---|
| Genotype: | At the point of inoculation | 25 cm above the point of inoculation[a] |
| Wild type | 10.6 (+/−15) × 10⁶ | 0 |
| HxfA | 6 (+/−7) × 10⁶ | 5.3 (+/−8) × 10⁵ |
| Dmt | 36.6 (+/−5.2) × 10⁶ | 3.6 (+/−1.8) × 10⁵ |
| BfeA | 4.3 (+/−4.6) × 10⁶ | 4.6 (+/−4.4) × 10⁴ |
| Gluc | 2.8 (+/−2.6) × 10⁶ | 1.4 (+/−0.9) × 10⁷ |
| PaaK | 25 (+/−10) × 10⁶ | 1.8 (+/−0.1) × 10⁷ |
| hypothetical | 6.3 (+/−4.5) × 10⁶ | 2.4 (+/−16) × 10⁴ |

[a] significance indicated in bold type; significance defined as $p < 0.01$

TABLE 4

Cell-cell aggregation and cell-surface attachment of Xf wild type, hxfA and hxfB Tn5 mutants

| | | Cell-surface attachment[b] on: | | |
|---|---|---|---|---|
| Geno-type: | Cell-cell aggregation[a] | Glass surface | Polystyrene surface | Polypropylene surface |
| Wild type | 36.2 +/− 8.9 | 0.9 +/− 0.7 | 0.07 +/− 0.020 | .25 +/− 0.04 |
| HxfA | 8.9 +/− 6.5[c] | 0.5 +/− 0.3 | 0.06 +/− 0.010 | .20 +/− 0.03 |
| HxfB | 9.2 +/− 1.0 | ND[d] | ND | ND |

[a] percentage of cell-cell aggregation was assessed as described in Burdman et al., 2000
[b] cell-surface attachment was assessed by the crystal violet staining method as in Espinosa-Urgel et al., 2000
[c] numbers in bold type are significantly different than wild type. Significance was defined as $p < 0.01$
[d] not determined

REFERENCES

The following references are hereby incorporated by reference in their entirety.

Altschul, S. F., W. Gish, W. Miller, E. W. Myers, and D. J. Lipman. 1990. Basic local alignment search tool. J. Mol. Biol. 215:403-410

Bayot, R. G., and S. M. Ries. 1986. Role of motility in apple blossom infection by *Erwinia amylovora* and studies of fire blight control with attractant and repellent compounds. Phytopathology 76:441-445.

Beattie, G. A., and S. E. Lindow. 1994. Epiphytic fitness of phytopathogenic bacteria: physiological adaptations for growth and survival. Curr Top Microbiol Immunol. 192:1-27.

Bhattacharyya, A., S. Stilwagen, G. Reznik, H. Feil, W. S. Feil, I. Anderson, A. Bernal, M. D'Souza, N. Ivanova, V. Kapatral, N. Larsen, T. Los, A. Lykidis, E. Jr. Selkov, T. L. Walunas, A. Purcell, R. A. Edwards, T. Hawkins, R. Haselkorn, R. Overbeek, N. C. Kyrpides, and P. F. Predki. 2002. Draft sequencing and comparative genomics of Xylella fastidiosa strains reveal novel biological insights. Genome Research 10:1556-1563.

Burdman, S., E, Jurkevirtch, M. Soria-Diaz, A. M. Serrano, and Y. Okon. 2000. Extracellular polysaccharide composition of *Azospirillum brasilense* and its relation with cell aggregation. FEMS Microbiol. Lett. 189:259-264.

Caetano-Anoles G. 1993. Amplifying DNA with arbitrary oligonucleotide primers. PCR Methods Appl. 3:85-94.

Chun, K. T., H. J. Edenberg, M. R. Kelley, and M. G. Goebl. 1997. Rapid amplification of uncharacterized transposon-tagged DNA sequences from genomic DNA. Yeast 13:233-40.

Cotter, P. A., M. H. Yuk, S. Mattoo, B. J. Akerley, J. Boschwitz, D. A. Relman, and J. F. Miller. 1998. Filamentous hemagglutinin of *Bordetella bronchiseptica* is required for efficient establishment of tracheal colonization. Infect Immun. 66:5921-9.

Cunningham, M. L., R. G. Titus, S. J. Turco, and S. M. Beverley. 2001. Regulation of differentiation to the infective stage of the protozoan parasite *Leishmania major* by tetrahydrobiopterin. Science 292:285-287.

da Silva, F. R., A. L. Vettore, E. L. Kemper, A. Leite, and P. Arruda. 2001. Fastidian gum: the *Xylella fastidiosa* exopolysaccharide possibly involved in bacterial pathogenicity. FEMS Microbiol Lett. 203:165-71 de Souza, A. A., M. A. Takita, H. D. Coletta-Filho, C. Caldana, G. M. Yanai, N. H. Muto, R. C. de Oliveira, L. R. Nunes, and M. A. Machado. 2004. Gene expression profile of the plant pathogen *Xylella fastidiosa* during biofilm formation in vitro. FEMS Microbiol. Lett. 237:341-53.

Davis, M. J., W. J. French, and N. W. Schaad. 1981. Axenic culture of the bacteria associated with phony peach disease of peach and plum leaf scald. Curr. Microbiol. 6:309-314.

De Lima, J. E. O., V. S. Miranda, J. S. Hartung, R. H. Brlansky, A. Coutinho, S. R. Roberto, and E. F. Carlos. 1998. Coffee leaf scorch bacterium: Axenic culture, pathogenicity, and comparison with *Xylella fastidiosa* of citrus. Plant Disease 82:94-97.

DeLoney, C. R., T. M. Bartley, and K. L. Visick. 2002. Role for phosphoglucomutase in *Vibrio fischeri*-Euprymna scolopes symbiosis. J. Bacteriol. 184:5121-5129.

Dow, J. M., B. R. Clarke, D. E. Milligan, J. L. Tang, and M. J. Daniels. 1990. Extracellular proteases from *Xanthomonas campestris* pv. *campestris*, the black rot pathogen. Appl. Environ. Microbiol. 56:2994-2998.

Erbs, G. and M.-A. Newman. 2003. The role of lipopolysaccharides in induction of plant defense. Mol. Plant. Pathol. 4:421-425.

Espinoas-Urgel, M., A. Salido, and J. L. Ramos. 2000. Genetic analysis of functions involved in adhesion of *Pseudomonas putida* to seeds. J. Bacteriol. 182:2363-2369.

Feil, H., W. S. Feil, J. C. Detter, A. H. Purcell, and S. E. Lindow. 2003. Site-directed disruption of the fimA and fimB fimbrial genes of *Xylella fastidiosa*. Phytopathology. 93:675-682.

Fernandez, L., I. Marquez, and J. A. Guijarro. 2004. Identification of specific in vivo-induced (ivi) genes in *Yersinia ruckeri* and analysis of ruckerbactin, a catecholate siderophore iron acquisition system. Appl. Environ. Microbiol. 70:5199-5207.

Guilhabert, M. R., L. M. Hoffman, D. A. Mills, B. C. and Kirkpatrick. 2001. Transposon mutagenesis of *Xylella fastidiosa* by electroporation of Tn5 synaptic complexes. Mol. Plant-Microbe Interact. 14:701-706.

Guilhabert, M. R., and B. C. Kirkpatrick. 2003. Transformation of *Xylella fastidiosa* with broad host range RSF1010 plasmids. Mol. Plant. Pathol. 4:279-285.

Guilhabert, M. R., and B. C. Kirkpatrick, 2005. Identification of *Xylella fastidiosa* Antivirulence genes: hemagglutinin adhesions contribute to *X. fastidiosa* biofilm maturation and colonization and attenuate virulence. Molecular Plant Microbe Interactions 18: 856-868.

Hatterman, D. R., and S. M. Ries. 1989. Motility of *Pseudomonas syringae* pv. *glycinea* and its role in infection. Phytopathology 79:284-289.

Hawes, M. C., and L. Y. Smith. 1989. Requirement for chemotaxis in pathogenicity of *Agrobacterium tumefaciens* on roots of soil-grown pea plants. J. Bacteriol. 171: 5668-5671

Hermann, S. R., J. A. Miller, S. O'Neill, T. T. Tsao, R. M. Harding, and J. L. Dale. 2000. Single-primer amplification of flanking sequences. Biotechniques 29:1176-8, 1180.

Hill, B. L., and A. H. Purcell. 1995. Multiplication and movement of *Xylella fastidiosa* within grapevine and four other plants. Phytopathology 85:1368-1372.

Hopkins, D. L. 1989. Xylem-limited bacterial pathogen of plants. Ann. Rev. Phytopathol. 27:271-290.

Inzana, T. J., and M. A. Apicella. 1999. Use of a bilayer stacking gel to improve resolution of lipopolysaccharides and lipooligosaccharides in polyacrylamide gels. Electrophoresis. 20:462-465.

Iocco, P., T. Franks, and M. R. Thomas. 2001. Genetic transformation of major wine grape cultivars of *Vitis vinifera* L. Transgenic Research 10(2):105-112.

Jacob-Dubuisson, F., C. Locht, and R. Antoine. 2001. Two-partner secretion in Gram-negative bacteria: a thrifty, specific pathway for large virulence proteins. Mol. Microbiol.

Kang Y., H. Liu, S. Genin, M. A. Schell, and T. P. Denny. 2002. *Ralstonia solanacearum* requires type 4 pili to adhere to multiple surfaces and for natural transformation and virulence. Mol. Microbiol. 46:427-37

Kannenberg, E. L., S. Perotto, V. Bianciotto, E. A. Rathbun, and N. J. Brewin. 1994. Lipopolysaccharide epitope expression of *Rhizobium bacteroids* as revealed by in situ immunolabelling of pea root nodule sections. J. Bacteriol. 176:2021-32.

Kwakman, J. H., and P. W. Postma. 1994. Glucose kinase has a regulatory role in carbon catabolite repression in *Streptomyces coelicolor*. J. Bacteriol. 176:694-8.

Leite, B., P. C. Andersen, and M. L. Ishida. 2004. Colony aggregation and biofilm formation in xylem chemistry-based media for *Xylella fastidiosa*. FEMS Microbiol. Lett. 230:283-290.

Li, W-B., C. H. Zhou, W. D. Pria, D. C. Teixeira, V. S. Miranda, E. O. Pereira, A. J. Ayres, C. X. He, P. L. Costa, and J. S. Hartung. 2002. Citrus and coffee strains of *Xylella fastidiosa* induce Pierce's disease in grapevines. Plant Disease 86:1206-1211.

Locht, C., R. Antoine, and F. Jacob-Dubuisson. 2001. *Bordetella pertussis*, molecular pathogenesis under multiple aspects. Curr. Opin. Microbiol. 4:82-89.

Lyon, W. R., and M. G. Caparon. 2004. Role for serine protease HtrA (DegP) of *Streptococcus pyogenes* in the biogenesis of virulence factors SpeB and the hemolysin streptolysin S. Infect Immun. 72:1618-1625.

Madigan, M. T., J. M. Martinko, and J. Parker. 1970. Brock biology of microorganisms. Prentice Hall, Upper Saddle River, N.J.

Marques, L. L. R., H. Ceri, G. P. Manfio, D. M. Reid, and M. E. Olson. 2002. Characterization of biofilm formation by *Xylella fastidiosa* in vitro. Plant Disease. 86:633-638.

Matthysse, A. G. and S. McMahan. 1998. Root colonization by *Agrobacterium tumefaciens* is reduced in cel, attB, attD, and attR mutants. Appl. Environ. Microbiol. 64:2341-2345.

Mezzetti, B., T. Pandolfini, O. Navacchi, and L. Landi. 2002. Genetic transformation of *Vitis vinifera* via organogenesis, BMC Biotechnology 2:18.

Mouslim, C., F. Hilbert, H. Huang, and E. A. Groisman. 2002. Conflicting needs for a *Salmonella* hypervirulence gene in host and non-host environments. Mol. Microbiol.

Newman, M. A., E. von Roepenack-Lahaye, A. Parr, M. J. Daniels, and J. M. Dow. 2002. Prior exposure to lipopolysaccharide potentiates expression of plant defenses in response to bacteria. Plant J. 29:487-495.

Ojanen-Reuhs, T., N. Kallkinen, B. Westerlund-Wikstrom, J. van Doom, K. Haahtela, E. L. Nurmiaho-Lassila, K. Wengelnik, U. Bonas, and T. K. Korhonen. 1997. Characterization of the fimA gene encoding bundle-forming fimbriae of the plant pathogen *Xanthomonas campestris* pv. *vesicatoria*. J. Bacteriol. 179:1280-90

Otteman, K. M., and J. F. Miller. 1997. Roles for motility in bacterial-host interactions. Mol. Microbiol. 24:1109-1117

Panapoulos, N. J., and M. N. Schroth. 1974. Role of flagellar motility in the invasion of bean leaves by *Pseudomonas phaseolicola*. Phytopathology 64:1389-1397.

Park, J. Y., N. Takahara, A. Gabriele, E. Chou, K. Naruse, K. Suzuma, T. Yamauchi, S. W. Ha, M. Meier, C. J. Rhodes, and G. L. King. 2000. Induction of endothelin-1 expression by glucose: an effect of protein kinase C activation. Diabetes 49:1239-48.

Pennings, J. L., J. T. Keltjens, and G. D. Vogels. 1998. Isolation and characterization of *Methanobacterium thermoautotrophicum* DeltaH mutants unable to grow under hydrogen-deprived conditions. J. Bacteriol. 180:2676-81.

Purcell, A. H. 1997. *Xylella fastidiosa*, a regional problem or global threat? J. Plant. Pathol. 79:99-105.

Purcell, A. H. and S. R. Saunders. 1999. Fate of Pierce's disease strains of *Xylella fastidiosa* in common riparian plants in California. Plant Disease 83:825-830.

Purcell, A., H. and D. L. Hopkins. 1996. Fastidious xylem-limited bacterial plant pathogens. Annu. Rev. Phytopathol. 34:131-51.

Qin X., and J. S. Hartung. 2001. Construction of a shuttle vector and transformation of *Xylella fastidiosa* with plasmid DNA. Curr. Microbiol. 43:158-62

Ray, S., K., R. Rajeshwari, Y. Sharma, and R. V. Sonti. 2002. A high-molecular-weight outer membrane protein of *Xanthomonas oryzae* pv. *oryzae* exhibits similarity to non-fimbrial adhesins of animal pathogenic bacteria and is required for optimum virulence. Mol. Microbiol. 46:637-47.

Rojas, C. M., J. H. Ham, W.-L. Deng, and J. J. Doyle. 2002. HecA, a member of a class of adhesins produced by diverse pathogenic bacteria, contributes to the attachment, aggregation, epidermal cell killing, and virulence phenotypes of *Erwinia chrysanthethemi* EC16 on *Nicotiana clevelandii* seedlings. Proc. Natl. Acad. Sci. USA 99:13142-13147.

Romantschuk, M., and D. H. Bamford. 1986. The causal agent of halo blight in bean, *Pseudomonas syringae* pv. *phaseolicola*, attaches to stomata via its pili. Microb. Pathog.

Schonherr R, R. Tsolis, T. Focareta, and V. Braun. 1993. Amino acid replacements in the *Serratia marcescens* haemolysin ShIA define sites involved in activation and secretion. Mol. Microbiol. 9:1229-1237.

Simpson, A. J. G. et al. 2000. The genome sequence of the plant pathogen *Xylella fastidiosa*. Nature 406:151-157.

Skurnik, M. and P. Toivanen. 1993. *Yersinia enterocolitica* lipopolysaccharide: genetics and virulence. Trends Microbiol. 1:148-152.

Smart C. D., B. Schneider, C. L. Blomquist, L. J. Guerra, N. A. Harrison, U. Ahrens, K. H. Lorenz, E. Seemuller, and B. C. Kirkpatrick. 1996. Phytoplasma-specific PCR primers based on sequences of the 16S-23S rRNA spacer region. Appl Environ Microbiol. 62:2988-2993.

Sohel, I., J. L. Puente, W. J. Murray, J. Vuopio-Varkila, and G. K. Schoolnik. 1993. Cloning and characterization of the bundle-forming pilin gene of enteropathogenic *Escherichia coli* and its distribution in *Salmonella* serotypes. Mol. Microbiol. 7:563-575.

Spath, C., A. Kraus, and W. Hillen. 1997. Contribution of glucose kinase to glucose repression of xylose utilization in *Bacillus megaterium*. J. Bacteriol. 179:7603-7605.

Strom, M. S. and S. Lory, S. 1993. Structure-function and biogenesis of the type IV pili. Annu. Rev. Microbiol. 47:565-96.

Tans-Kersten, J., H. Huang, and C. Allen. 2001. *Ralstonia solanacearum* needs motility for invasive virulence on tomato. J. Bacteriol. 183:3597-3605

Thompson, J. D., D. G. Higgins, and T. J. Gibson. 1994. CLUSTAL W: improving the sensitivity of progressive multiple sequence alignment through sequence weighting, position-specific gap penalties and weight matrix choice. Nucleic Acids Res. 22:4673-4680.

Tsai C. M., and C. E. Frasch. 1982. A sensitive silver stain for detecting lipopolysaccharides in polyacrylamide gels. Anal. Biochem. 119:115-9 van Doom, J., P. M. Boonekamp, and B. Oudega, B. 1994. Partial characterization of fimbriae of *Xanthomonas campestris* pv. *hyacinthi*. Mol. Plant. Microbe Interact. 7:334-344.

Van Sluys, M. A., et al., 2003. Comparative analyses of the complete genome sequences of Pierce's disease and citrus variegated chlorosis strains of *Xylella fastidiosa*. J. Bacteriol. 185:1018-1026.

VandeBroek, A., and J. Vanderleyden. 1995. The role of bacterial motility, chemotaxis, and attachment in bacteria-plant interactions. Mol. Plant-Microbe Interact. 8:800-810.

Wagner, E., S. Marcandier, O. Egeter, J. Deutscher, F. Gotz, and R. Bruckner. 1995. Glucose kinase-dependent catabolite repression in *Staphylococcus xylosus*. J. Bacteriol. 177: 6144-6152.

Zhang, Y. P., J. K. Uyemoto, and B. C. Kirkpatrick. 1998. Small-scale procedure for extracting nucleic acids from woody plants infected with various phytopathogens for PCR assay. J. Virol. Methods 71:45-50.

We claim:

1. A construct comprising a nucleic acid molecule encoding a recombinant polypeptide with at least about 85% identity to SEQ ID NO: 5 (HxfA) or at least about 85% identity to SEQ ID NO: 3 (HxfB).

2. The construct of claim 1 wherein the nucleic acid molecule encodes a polypeptide with at least about 90% identity to SEQ ID NO: 5 (HxfA).

3. The construct of claim 1 wherein the nucleic acid molecule encodes a polypeptide with at least about 90% identity to SEQ ID NO: 3 (HxfB).

4. The construct of claim 1 wherein the nucleic acid molecule encodes a polypeptide with at least about 95% identity to SEQ ID NO: 5 (HxfA).

5. The construct of claim 1 wherein the nucleic acid molecule encodes a polypeptide with at least about 95% identity to SEQ ID NO: 3 (HxfB).

6. The construct of claim 1 wherein the nucleic acid molecule encodes a polypeptide with at least about 97% identity to SEQ ID NO: 5 (HxfA).

7. The construct of claim 1 wherein the nucleic acid molecule encodes a polypeptide with at least about 97% identity to SEQ ID NO: 3 (HxfB).

8. The construct of claim 1 wherein the nucleic acid molecule encodes a polypeptide comprising the polypeptide sequence of SEQ ID NO: 5 (HxfA).

9. The construct of claim 1 wherein the nucleic acid molecule encodes a polypeptide comprising the polypeptide sequence of SEQ ID NO: 3 (HxfB).

10. The construct of claim 1 wherein said nucleic acid molecule is operably linked to a promoter.

11. The construct of claim 10 wherein the promoter is selected from the group consisting of constitutive promoters, inducible promoters, tissue- and cell-specific promoters, and developmentally-regulated promoters.

12. A host cell expressing a recombinant polypeptide with at least about 85% identity to SEQ ID NO: 5 (HxfA) or at least about 85% identity to SEQ ID NO: 3 (HxfB), wherein said polypeptide confers resistance to *Xylella fastidiosa* infection when expressed in plants.

13. The host cell of claim 12, wherein said host cell is selected from the group consisting of *Pseudomonas, Agrobacterium*, and avirulent *Xylella fastidiosa*.

14. A plant containing the host cell of claim 12.

15. A transgenic plant expressing a recombinant polypeptide with at least about 85% identity to SEQ ID NO: 5 (HxfA) or at least about 85% identity to SEQ ID NO: 3 (HxfB), wherein said transgenic plant is more resistant to *Xylella fastidiosa* infection as compared to a corresponding plant not expressing said recombinant polypeptide.

16. The transgenic plant of claim 15 wherein the plant is selected from the group consisting of grapevines, citrus, peach, plum, oleander, elm, sycamore, oak, maple and coffee.

17. The transgenic plant of claim 16 where the plant is a grapevine.

18. A seed produced by the transgenic plant of claim 15, wherein the seed comprises a nucleic acid molecule encoding the recombinant polypeptide with at least about 85% identity to SEQ ID NO: 5 (HxfA) or at least about 85% identity to SEQ ID NO: 3 (HxfB).

* * * * *

SEQUENCE LISTING

```
<160> NUMBER OF SEQ ID NOS: 33

<210> SEQ ID NO 1
```

```
<211> LENGTH: 438
<212> TYPE: PRT
<213> ORGANISM: Xylella fastidiosa

<400> SEQUENCE: 1
```

| | | | | | | | | | | | | | | |
|---|---|---|---|---|---|---|---|---|---|---|---|---|---|---|
| Met | Ala | Thr | Gly | Gln | Leu | Thr | Glu | Gly | Ser | Pro | Leu | His | Ala | Leu |
| 1 | | | | 5 | | | | | 10 | | | | | 15 |
| His | Ala | Leu | Leu | Ala | Cys | Ala | Gly | Ala | Ala | Ser | Gln | Gln | Arg | Cys |
| | | | 20 | | | | | 25 | | | | | 30 | |
| Ser | Ser | Gly | Ala | Gln | Gly | Ala | Ala | Ser | Ser | Val | Leu | Thr | Gly | Leu |
| | | 35 | | | | | 40 | | | | | 45 | | |
| Phe | Ser | Asp | Pro | Arg | Pro | Glu | Asp | Thr | Ala | Gln | Asp | Arg | Glu | Ala | Lys |
| 50 | | | | | 55 | | | | | 60 | | | | | |
| Arg | Asn | Leu | Ile | Thr | Ser | Ile | Val | Thr | Gly | Ile | Ala | Ser | Thr | Thr | His |
| 65 | | | | | 70 | | | | | 75 | | | | | 80 |
| Thr | Asp | Ala | Ala | Thr | Ala | Thr | His | Ala | Ala | Ile | Ala | Ala | Val | Asp | Asn |
| | | | | 85 | | | | | 90 | | | | | 95 | |
| Asn | Trp | Leu | Ala | Ala | Lys | Gln | Tyr | Val | Gln | Met | Val | Ser | Glu | Leu |
| | | | 100 | | | | | 105 | | | | | 110 | |
| Glu | Ala | Ala | Thr | Glu | Lys | Asp | Lys | Gly | Arg | Leu | Glu | Glu | Lys | Val |
| | | | 115 | | | | | 120 | | | | | 125 | |
| Arg | Ala | Lys | Trp | Arg | Glu | Ile | Ser | Ala | Arg | Gln | Asp | Lys | Leu | Thr | Ala |
| 130 | | | | | 135 | | | | | 140 | | | | | |
| Asp | Gly | Leu | Leu | Lys | Gly | Leu | Lys | Glu | Ser | Gly | Ile | Ser | Asn | Ile | Asn |
| 145 | | | | | 150 | | | | | 155 | | | | | 160 |
| Gly | Leu | Glu | His | Leu | Ile | Leu | His | Pro | Val | Asp | Val | Phe | His | Glu | Leu |
| | | | | 165 | | | | | 170 | | | | | 175 | |
| Glu | Lys | Ile | Leu | Thr | His | Pro | Lys | Leu | Leu | Val | Gln | Leu | Gly | Glu | Arg |
| | | | 180 | | | | | 185 | | | | | 190 | | |
| Ala | Val | Gln | Asp | Leu | Leu | Asn | Lys | Val | Ser | Arg | Met | Ala | Glu | Ala | Leu |
| | | | 195 | | | | | 200 | | | | | 205 | | |
| Tyr | Val | Gly | Gly | Asp | Gln | His | Ala | Lys | Gln | Phe | Gly | Glu | Asp | Leu | Gly |
| | | 210 | | | | | 215 | | | | | 220 | | | |
| Ser | Val | Ile | Ala | Asp | Val | Gly | Phe | Ala | Leu | Ala | Ala | Gly | Thr | Val |
| 225 | | | | | 230 | | | | | 235 | | | | | 240 |
| Lys | Ala | Gly | Glu | Ile | Leu | Ala | Glu | Ala | Gly | Ile | Asn | Leu | Ser | Lys | Asp |
| | | | | 245 | | | | | 250 | | | | | 255 | |
| Val | Leu | Glu | Gly | Met | Ala | Thr | Ser | Lys | Ala | Asn | Lys | Leu | Ser | Asn | Val |
| | | | 260 | | | | | 265 | | | | | 270 | | |
| Asp | Asp | Ile | Val | Ser | Ala | Glu | Gln | Glu | Ala | Leu | Thr | Arg | Ile | Gly | Asn |
| | | 275 | | | | | 280 | | | | | 285 | | | |
| His | Pro | Asn | Gly | Pro | Asp | Leu | Thr | Gln | Lys | Pro | Gly | Gln | Phe | Ile |
| | 290 | | | | | 295 | | | | | 300 | | | | |
| Ala | Leu | Gln | Gln | Glu | Lys | Arg | Ile | Glu | Asp | Val | Lys | Ser | Val | Val | Gly |
| 305 | | | | | 310 | | | | | 315 | | | | | 320 |
| Arg | Arg | Ser | Pro | Lys | Asn | Glu | Leu | Val | Val | Asp | Arg | Ile | Lys | Ile | Glu |
| | | | | 325 | | | | | 330 | | | | | 335 | |
| Tyr | Ile | Pro | Tyr | Asp | Pro | Leu | Val | Lys | Gly | Gly | Ser | Asn | Lys | Ala | Gly |
| | | | 340 | | | | | 345 | | | | | 350 | | |
| Asn | Val | Arg | Val | Phe | Lys | Ser | Glu | Ala | Leu | Thr | Asp | Lys | Gln | Ile | Met |
| | | 355 | | | | | 360 | | | | | 365 | | | |
| Asn | Tyr | Ala | Gln | Gln | Leu | Ala | Gly | Asp | Val | Pro | Leu | Lys | Glu | Thr | Ser |
| | 370 | | | | | 375 | | | | | 380 | | | | |
| Lys | Lys | Gly | Val | Tyr | Leu | Ala | Glu | Leu | Ser | Asp | Gly | Thr | Lys | Val | Thr |
| 385 | | | | | 390 | | | | | 395 | | | | | 400 |

Leu Arg Ser Val Ser Ser Asp Gln Val Thr Lys Ala Arg Trp Thr
        405                 410                 415

Ile Asp Ile Ala Asn Asn Pro Ser Leu Arg Glu Ile Thr Lys Glu Lys
            420                 425                 430

Val Glu Leu Lys Phe Arg
        435

<210> SEQ ID NO 2
<211> LENGTH: 436
<212> TYPE: PRT
<213> ORGANISM: Xylella fastidiosa

<400> SEQUENCE: 2

Met Ala Thr Gly Gln Leu Thr Glu Gly Ser Pro Leu His Ala Ala Leu
 1               5                  10                  15

His Ala Leu Leu Ala Cys Ala Gly Ala Gly Ala Ser Gln Gln Arg Cys
            20                  25                  30

Ser Ser Gly Ala Gln Gly Ala Ala Ser Ser Val Leu Thr Gly Leu
        35                  40                  45

Phe Ser Asp Pro Arg Pro Glu Asp Thr Ala Gln Asp Arg Glu Ala Lys
 50                  55                  60

Arg Asn Leu Ile Thr Ser Ile Val Thr Gly Ile Ala Ser Thr His
65                   70                  75                  80

Thr Asp Ala Ala Thr Ala Thr His Ala Ala Ile Ala Ala Val Asp Asn
                85                  90                  95

Asn Trp Leu Ala Ala Lys Gln Tyr Val Gln Met Val Ser Glu Glu Leu
            100                 105                 110

Glu Ala Ala Thr Glu Lys Asp Lys Gly Arg Leu Glu Glu Glu Lys Val
        115                 120                 125

Arg Ala Lys Trp Arg Glu Ile Ser Ala Arg Gln Asp Lys Leu Thr Ala
130                 135                 140

Asp Gly Leu Leu Lys Gly Leu Lys Glu Ser Gly Ile Ser Asn Ile Asn
145                 150                 155                 160

Gly Leu Glu His Leu Ile Leu His Pro Val Asp Val Phe His Glu Leu
                165                 170                 175

Glu Lys Ile Leu Thr His Pro Lys Leu Leu Val Gln Leu Gly Glu Arg
            180                 185                 190

Ala Phe Gln Glu Leu Leu Asn Lys Val Ser Arg Met Ser Glu Ala Leu
        195                 200                 205

Ile Val Gly Gly Asp Gln His Ala Lys Gln Phe Gly Glu Asp Leu Gly
210                 215                 220

Ser Val Ile Ala Asp Val Gly Phe Ala Leu Ala Ala Gly Thr Val
225                 230                 235                 240

Lys Ala Gly Glu Ile Leu Ala Glu Ala Gly Ile Asn Leu Ser Lys Asp
                245                 250                 255

Val Leu Glu Gly Met Ala Thr Ser Lys Ala Asn Lys Leu Ser Asn Val
            260                 265                 270

Asp Asp Ile Val Ser Ala Glu Gln Glu Ala Leu Thr Arg Ile Gly Asn
        275                 280                 285

His Pro Asn Gly Pro Asp Val Thr Gln Lys Pro Gly Gln Tyr Ile
290                 295                 300

Ala Leu Gln Gln Gly Ala Phe Asn Lys Ala Ile Ala Leu Val Asp Lys
305                 310                 315                 320

Ser Asn Ser Ser Ser Glu Phe Val Phe Ser Gly Leu Lys Ala Lys Val
                325                 330                 335

```
Thr Pro Arg Gly Ser Val Gly Ser Asn Lys Ala Gly Asn Val Lys
            340                 345                 350

Val Leu Glu Ser Glu Ala Phe Ser Asp Gln Lys Ile Arg Glu Phe Ala
355                 360                 365

Gln Gln Leu Ala Gly Asp Val Pro Leu Lys Glu Thr Arg Thr Pro Gly
    370                 375                 380

Val Tyr Ala Ala Lys Leu Ser Asp Gly Ser Trp Val Arg Leu Arg Ser
385                 390                 395                 400

Val Ser Ser Asn Asn Glu Thr Lys Ala Arg Trp Thr Ile Asp Ile
                405                 410                 415

Glu Lys Asn Pro Thr Leu Met Glu Leu Thr Lys Thr Glu Lys Phe Glu
                420                 425                 430

Ile Lys Phe Arg
        435

<210> SEQ ID NO 3
<211> LENGTH: 3377
<212> TYPE: PRT
<213> ORGANISM: Xylella fastidiosa

<400> SEQUENCE: 3

Met Asn Lys Asp Leu Tyr Arg Leu Ile Tyr Asn Arg Ala Leu Arg Leu
1               5                   10                  15

Trp Gln Val Ala Ser Glu Arg Thr Thr Ala Pro Gly Gly Thr Ser Asp
                20                  25                  30

Pro Ser Pro Thr Ala Gln Pro Pro Ala Arg Ala Cys Leu His Pro Ile
            35                  40                  45

Pro Phe Ala Leu Trp Leu Thr Leu Gly Trp Val Thr Ile Thr Gly Ile
        50                  55                  60

Ala Thr Ala Gln Val Val Ala Asp Pro His Ala Pro Gly Gln Gln Arg
65                  70                  75                  80

Pro Thr Val Leu Ala Ala Pro Asn Gly Thr Pro Leu Ile Asn Ile Gln
                85                  90                  95

Thr Pro Ser Pro Ala Gly Val Ser Arg Asn Thr Tyr Gln Gln Phe Asp
            100                 105                 110

Ile Thr Pro Gln Gly Ala Ile Leu Asn Asn Ala Arg Thr Pro Thr Gln
        115                 120                 125

Thr His Leu Ala Gly Thr Val Gln Gly Asn Pro Trp Leu Ala Ala Gly
    130                 135                 140

Thr Ala Lys Ile Ile Leu Asn Glu Val Asn Ser Pro Thr Ser Thr Gln
145                 150                 155                 160

Leu His Gly Thr Met Glu Val Ala Gly Ala Arg Ala Gln Leu Ile Ile
                165                 170                 175

Ala Asn Pro Ser Gly Ile Thr Cys Asn Gly Cys Gly Val Ile Asn Ala
            180                 185                 190

His Gln Leu Thr Leu Thr Thr Gly Thr Pro Ile Phe Asn Ala Arg Gly
        195                 200                 205

Ala Leu Asp His Tyr Arg Val Gln Gly Gly Ala Ile Gln Ile Asp Gly
    210                 215                 220

Leu Gly Leu Asp Ser His Ser Thr Asp Tyr Thr Ala Leu Ile Ala Arg
225                 230                 235                 240

Thr Val Gln Leu Asn Ala Gly Leu Trp Ala His Thr Leu Gln Thr Thr
                245                 250                 255

Thr Gly Pro Ala Thr Val Ala Leu Asp Gly His Pro Thr Ala Ser Leu
            260                 265                 270
```

```
Pro Ala Pro Pro Gly Asp Arg Pro Thr Val Ala Leu Asp Val Ser Ala
            275                 280                 285

Leu Gly Gly Met Tyr Ala Gly Lys Ile Thr Leu Ile Gly Thr Glu His
    290                 295                 300

Gly Leu Gly Val Arg Asn Ala Gly Gln Leu Ser Ala Thr Ser Ala Pro
305                 310                 315                 320

Leu Thr Val Thr Val Asp Gly Leu Leu Glu Asn Thr Gly Arg Leu Gln
                325                 330                 335

Ser Ala Thr Asp Thr Gln Leu Asn Ala Thr Ala Gln Val Thr Asn Ser
            340                 345                 350

Gly Leu Ile Ser Ala Ala Gln Thr Leu Thr Leu His Thr Pro Thr Thr
    355                 360                 365

Ile Asp Asn Arg Ser Gly Thr Leu Asn Ala Ala Arg Leu Asp Ile Thr
370                 375                 380

Gly Thr Arg Leu Asp Asn Arg Gly Gly His Ile Gln Gln Thr Gly Leu
385                 390                 395                 400

Gln Pro Leu Thr Leu Gln Thr Gln His Leu Asp Asn Gln Asp Gln Gly
                405                 410                 415

Arg Leu Gly Val Leu Asp Thr Pro Ala Pro Ala Thr Pro Ala Thr Pro
            420                 425                 430

Thr Val Thr Ala Pro Ile Ser Asn Ala Pro Pro Thr Val Thr Ala Pro
    435                 440                 445

Pro Ala Thr Asp Pro Thr Thr Ser Pro Val Ala Pro Thr Val Pro His
450                 455                 460

Leu Ala His Gly Thr Leu Thr Leu Thr Gln Thr Ile Asp Asn Arg Gly
465                 470                 475                 480

Gly His Ile Thr Ala Gly Gly Pro Ile Asp Ala Ile Leu Thr Asp Leu
                485                 490                 495

Asp Asn Arg Asp Gly Thr Ala Ala Leu Asn Arg Leu Thr Leu Gln Gly
            500                 505                 510

Gln Arg Leu Asp Asn Gln His Gly Ile Leu Thr Leu Ala Thr Asp Ala
    515                 520                 525

Thr Ile His Thr His Thr Leu Asn Asn Thr Ala Gly Gln Leu His Ala
530                 535                 540

Asn Gly Thr Leu Asp Leu Thr Ala Gln Arg Phe Ser Asn Gln Asn Gly
545                 550                 555                 560

Gln Leu Leu His Thr Gly Ser Gln Asn Ala Thr Leu Thr Ile Thr Asp
                565                 570                 575

Leu Leu Asp Asn Gln His Gly Leu Val Ala Ser Ala Ala Asn Ala Leu
            580                 585                 590

Thr Leu His Thr Asp His Leu Asn Asn Asp Ala Gly Gln Phe Gln Thr
    595                 600                 605

Asn Gly Ala Leu Asp Leu Thr Ala Gln Arg Phe Ser Asn Gln His Gly
610                 615                 620

Gln Phe Leu His Asn Ser Pro Gln Ser Ala His Leu Arg Ile Asp Gly
625                 630                 635                 640

Gln Leu Asp Asn Gln Gln Gly Val Leu Ala Ser Asn Ala Ala Glu Leu
                645                 650                 655

Thr Leu Glu Thr Gly Gln Phe Asn Asn Asp Ser Gly Thr Leu Gln Gln
            660                 665                 670

Ser Gly Gln Gly Thr Leu His Ile Asp Ala Ala Thr Leu Thr Gly His
    675                 680                 685

Gly Gly Thr Leu Thr Ser Gln Gly Ala Leu Thr Leu Thr Gly Thr His
```

```
                690              695              700
Thr Asp Leu Ser His Ala Thr Thr Ala Gln His Ile Thr Ile His
705                  710                  715                  720

Thr Asp Asp Leu Thr Thr Ala Gly Gly His Leu Thr Ala Tyr Gly Glu
                 725                  730                  735

His Thr Leu Gln Leu Asn Ala Arg Thr Arg Ile Asp Asn Thr Ala Gly
                 740                  745                  750

Thr Ile Ala Thr Asn Gly Ser Leu Asp Leu His Thr Ala Ala Leu Asp
                 755                  760                  765

Asn Thr Gly Gly Thr Leu His Ser Thr Ala Thr Gly Pro Asn Arg Leu
770                  775                  780

Asp Ile Thr His Thr Leu Thr Asn Thr Ala Gly His Leu Leu Leu Asn
785                  790                  795                  800

Gly Pro Thr Thr Leu Thr Thr Gly Thr Trp Thr Asn Thr Gly Gly Gln
                 805                  810                  815

Leu Gln Ile Thr Gly Pro Ala Thr Leu His Ala Thr Thr Leu Asp Asn
                 820                  825                  830

Arg Gly Gly Ile Leu His Thr Ala Thr Gly Pro Leu Asp Leu Arg Val
                 835                  840                  845

Thr Gly Thr Ile Asn Asn Gln Asp Asn Gly Ile Leu Ser Ser Thr Ala
850                  855                  860

Ala Leu Thr Leu Thr Ala Ala Ser Leu His Asn Gln His Gly Thr Leu
865                  870                  875                  880

Asp Ala Ala Gly Pro Ala His Leu Thr Leu Thr Gly Leu Leu Asp Asn
                 885                  890                  895

Thr Ala Gly Leu Leu Gln Thr Ala His Thr Leu Trp Leu Thr Ser Ala
                 900                  905                  910

Gly Leu Thr Asn Arg Ser Gly Thr Leu Thr Ala Ala Ala Leu Thr Leu
                 915                  920                  925

Asp Thr Gln Ala His Thr Leu Asp Asn Thr Ser Gly Arg Leu Gly Thr
                 930                  935                  940

Thr Thr Gly Asn Leu Thr Leu His Thr Gly Leu Leu Asp Asn Thr Ala
945                  950                  955                  960

Gly Leu Leu Gln Thr Ala Ala Thr Leu Thr Ile Asp Thr Gly Ala Ala
                 965                  970                  975

Pro Leu Thr Asn Arg Asp Gly Gly Thr Leu Leu Ala Ala Asp Thr Leu
                 980                  985                  990

Asp Leu His Thr Thr Thr Leu Asp Asn Arg Gly Gly Thr Ile Asp Ser
                 995                  1000                 1005

Gln Thr Ala Thr His Leu His Thr Thr Thr Ile Asp Asn Thr Thr Ala
                 1010                 1015                 1020

Gly His Ile Ser Ser Asn Gly Thr Leu Gln Ile Asp Gly Thr Thr Leu
1025                 1030                 1035                 1040

Thr Asn Thr Gly Gly Arg Leu His Ser Gly Gly Asp Thr Arg Leu His
                 1045                 1050                 1055

Leu Gln Asp Thr Leu Asn Asn His Asp Gly Arg Ile Thr Ala Ala Gly
                 1060                 1065                 1070

Thr Leu Asp Ile Thr Thr Thr Leu Asp Asn His Ser Thr Pro Leu
                 1075                 1080                 1085

Thr Ala Pro Pro Ala Thr Gln Thr Arg Ala Pro Thr Gly Ala Pro Asp
                 1090                 1095                 1100

Asn Gly Leu Tyr Ala Thr His Ile Gln Ile Ala Ser Thr Thr Leu Asp
1105                 1110                 1115                 1120
```

```
Asn Thr Ala Gly Thr Leu Ser Ala Ala Gln Asn Leu Thr Leu Thr Leu
            1125                1130                1135

Ser Asp Thr Leu Thr Asn Thr Ala Gly His Leu Ser Ala Gly Ala Thr
            1140                1145                1150

Leu Asp Leu Thr Ala Asp His Leu Ser Asn His Thr Gly Thr Leu Leu
            1155                1160                1165

Ser Gly Ala Ser Gln Thr Leu His Leu His Arg Leu Thr Gly Asp Gly
            1170                1175                1180

Arg Leu His Ala Gly Asn Ala Leu Thr Leu Thr Leu Gln Asp Ser Leu
1185                1190                1195                1200

Asp Thr Ala Gly Thr Leu Ser Ala Thr Gly Leu Leu Thr Leu Thr Thr
            1205                1210                1215

Ala Gly Asp Leu Thr Asn Arg Gly Leu Ile Gln Ala Ala Asp Leu Thr
            1220                1225                1230

Ala Arg Ala Arg Asp Ile Thr Thr Thr Ala Thr Gly Gln Leu Leu Ala
            1235                1240                1245

Thr Gly His Thr Gln Leu Thr Ala Thr Gly Thr Leu Asn Asn Ser Gly
            1250                1255                1260

His Leu Gln Ala Ala Asp Leu Thr Ala Gln Ala Arg Asp Ile Thr Thr
1265                1270                1275                1280

Thr Ala Thr Gly Gln Leu Leu Thr Thr Gly His Thr His Leu Thr Ala
            1285                1290                1295

Thr Gly Thr Leu Thr Asn Ser Gly Leu Leu Gln Ala Pro Asp Leu Thr
            1300                1305                1310

Ala Gln Ala Asn Thr Ile Thr Thr Thr Ala Thr Gly Arg Leu Leu Thr
            1315                1320                1325

Ser Gly His Ala Gln Leu Thr Ala Thr Asp Thr Leu Thr Asn Ser Gly
            1330                1335                1340

Leu Ala Gln Ala Gly Asp Leu Thr Val His Ala Arg Asp Ile Thr Asn
1345                1350                1355                1360

Thr Ala Thr Gly Gln Leu Ile Ala Asn Asn Leu Ala His Leu Thr Ala
            1365                1370                1375

Thr Gly Thr Leu Thr Asn Arg Gly Leu Ile Asp Ala Phe Thr Thr His
            1380                1385                1390

Leu Ser Ala Ala Thr Ile Asp Asn Leu Gly Thr Gly Arg Leu Tyr Gly
            1395                1400                1405

Asp His Ile Ala Leu Gln Ala Gln Thr Leu Thr Asn Arg Asp Glu Thr
            1410                1415                1420

Ser Asp Gly His Thr His Thr Ala Thr Ile Ala Ala Arg Gln Arg Leu
1425                1430                1435                1440

Asp Ile Gly Ala Asp Thr Leu Arg Asn Thr Ala Asn Ala Met Ile Leu
            1445                1450                1455

Ser Asp Gly Asp Ala Ala Ile Gly Ala Thr Leu Asp Asn Ala Leu His
            1460                1465                1470

Ala Thr Gly Ile Ala Ala Leu Leu Asp Asn Arg Ser Ala Thr Ile Asp
            1475                1480                1485

Ile Thr Gly Asn Leu Asn Ile Thr Thr Thr Leu Asn Asn Ile Arg
            1490                1495                1500

Glu Asn Val His Ile Ala His Ala Pro Asp Val Val Thr Glu Ala Arg
1505                1510                1515                1520

Leu Glu Gln Pro His Trp Arg Lys Asn Gln Pro Asn Gly Gly Ser Gly
            1525                1530                1535

Asp Phe Arg Leu Ser Ser Asn Tyr Asp Ala His Glu Ile Tyr Tyr Leu
            1540                1545                1550
```

```
Asn Pro Ala Asp Ile Leu Lys Asp Glu Pro Tyr Ile Thr Pro Asp Gly
        1555                1560                1565

Gln Gln Ile Arg Arg Ala Ile Val Arg Leu Thr Pro Gln Thr Ser Ala
    1570                1575                1580

Tyr Phe Tyr Ala Arg Gly Gly Leu Tyr Ala Ser Gln Ala Glu Arg Arg
1585                1590                1595                1600

Arg Met Asp Leu Thr Ala Arg Thr Gly Asp Ser Val Leu Leu Tyr Tyr
            1605                1610                1615

Thr Asp Arg Gln Asp Lys Gln Pro Asn Pro Asp His Ser Ala Ala Ala
        1620                1625                1630

Ala Thr Asn Asp Ser Ala Phe Ile Gly Leu Asp Thr Pro Gln Gln Asn
    1635                1640                1645

Glu Arg Leu Gln Thr Val Pro Ile Thr Tyr Ala Pro Gly Asp Asp Arg
1650                1655                1660

Leu Thr Tyr Asp Pro Thr Tyr Gly Thr Cys Thr Asp Asp Cys Val Arg
1665                1670                1675                1680

Leu Val Thr Trp His Asp Tyr Thr Asp Pro Asp Arg Thr Leu Ile Asp
            1685                1690                1695

Met His Arg Gly Pro Asn Asp Val Arg Asp Asn Glu Arg Tyr Arg Gln
        1700                1705                1710

Ala Thr Lys Thr Thr Gln Gln Glu Ile Leu Asn Pro Asp Ala Gly Ala
    1715                1720                1725

Ala Thr Leu Ile Gln Ser Gly Gly Thr Met Met Ile Gln Ala Ala Thr
1730                1735                1740

Leu Arg Asn His Tyr Ala Asp Leu Leu Ala Gly Gly Asp Gln Thr Ile
1745                1750                1755                1760

Val Gly Leu Pro Pro His Pro Pro Lys Asp Asn Pro Glu Asp Glu Gln
            1765                1770                1775

Lys Tyr Thr Pro Ala Leu Leu Ile Asp Asn Arg Ala Leu Gln Leu Ser
        1780                1785                1790

Arg Thr Asp Thr Phe Gln Asn Ile Ser Thr Thr Tyr Arg Gly Asp Thr
    1795                1800                1805

His Thr Trp Ser Asn Glu Ser Arg Thr Thr Pro Thr Ala Leu Ile Gly
1810                1815                1820

Gly Arg Ile Thr Ser Gly Gly His Gln His Ile Ala Ala Gln Lys Val
1825                1830                1835                1840

Asn Asn Val Thr Asp Ser Thr His Thr Pro Glu Pro Ile Gln His Leu
            1845                1850                1855

Thr Tyr Asn Pro Ser Thr Gln Thr Leu Ser Val Val Asn Gly Val Ile
        1860                1865                1870

Thr Ile Thr Asp Asn Ser Pro Ser Leu His Thr Val Ser Leu Ala Asp
    1875                1880                1885

Asn Gly Phe Ser His Gly Gln Glu Leu Thr Tyr Ile Pro Asp Gln Ser
1890                1895                1900

Ile Thr Thr Pro Asn Ala Pro Ile Arg Asp Pro Ala Ala Pro Pro Ala
1905                1910                1915                1920

Val Thr Val Thr Pro Thr Gly Pro Leu Thr Leu Pro Asn Asn Ser Leu
            1925                1930                1935

Phe Thr Ile His Pro Asp Thr Thr Leu Ile Thr Thr Asp Pro His
        1940                1945                1950

Phe Thr Leu Gly Arg Pro Tyr Thr Ser Ala Asp Ser Gln Leu His Ala
    1955                1960                1965

Leu Gly Asp His Asp Thr Leu His Lys Arg Leu Gly Asp Gly Tyr Tyr
```

```
                1970                1975                1980
Glu Gln Arg Leu Ile Arg Glu Gln Ile Ala Gln Leu Thr Gly Arg Arg
1985                1990                1995                2000

Arg Leu Asp Gly Tyr Thr Asp Asp His Gln Tyr Arg Ala Leu Leu
                2005                2010                2015

Asp Ala Gly Val Thr Val Thr Lys His Tyr Gly Leu Arg Pro Gly Ile
                2020                2025                2030

Ala Leu Ser Ala Asp Gln Leu Ala Gln Leu Thr Ser Asp Ile Val Trp
                2035                2040                2045

Leu Val Gln Gln Asn Val Gln Leu Pro Asp Gly Thr Thr Thr Arg Ala
                2050                2055                2060

Leu Val Pro Arg Leu Tyr Leu Arg Pro Arg Thr Gly Asp Leu Thr Gln
2065                2070                2075                2080

Asp Gly Ala Leu Met Ala Ala Ala Ser Thr Thr Ile Asn Ala His Thr
                2085                2090                2095

Leu Thr Asn Thr Gly Thr Ile Glu Ala Arg His Leu Ile Asp Ile Asn
                2100                2105                2110

Ala His Ile Met Asp Gln Gln Gly Gly Arg Leu Thr Ala Asp Ala Ile
                2115                2120                2125

Asp Ile His Thr Thr Gly Asp Phe Thr Thr Leu Gly Gly Gln Phe Lys
                2130                2135                2140

Ala Arg Asp Tyr Leu Asn Ile His Ala Gln Gly Asn Phe Val Ala Ser
2145                2150                2155                2160

Ser Thr Leu Arg Gln Ala Thr Thr Gln Gly Thr Arg His His Ser Leu
                2165                2170                2175

Thr Ala Leu Asp Gln Gln Ala Ser Phe Glu Val Thr Gly Pro Asp Ala
                2180                2185                2190

Thr Leu Gly Leu Ser Thr Asn Gln Ala Met Thr Gln Gln Ala Val Ala
                2195                2200                2205

Ile Ser Asn Thr Gly Thr Asp Gly Tyr Thr Ser Leu Lys Ala Thr Gly
                2210                2215                2220

Pro Leu His Leu Gly Thr Leu Asn Thr His Arg Ser Asp Thr Thr Gln
2225                2230                2235                2240

Trp Asp Pro Arg Asn Ser Arg His Ser Arg Ile Asp Thr Glu His Gly
                2245                2250                2255

Thr Ser Ile Arg Thr Ala Gly Asp Ile Ser Ile Ser Ala Asp Ala Gly
                2260                2265                2270

Ile Thr Gly Arg Ala Val Thr Leu Asp Ser Ser Ala Gly Asp Leu Thr
                2275                2280                2285

Leu Thr Ser Arg His Gly Ala Val Thr Leu Leu Ala Gly Glu Ala Arg
                2290                2295                2300

Leu Ser Asp Gln Gln Glu Arg Thr Ser Arg Arg Ser Gly Leu Leu Arg
2305                2310                2315                2320

Ser Ser Ser Ser His Ser Thr Ser Ser Ser Thr Asp Thr Val Ala Leu
                2325                2330                2335

Ser Ser Val Leu Gly Gly Lys Asn Ile Thr Ile Ala Ala Ala Asp Thr
                2340                2345                2350

Val His Ser Val Gly Thr Gln Phe Ile Ala Asp Gln Asp Val Thr Leu
                2355                2360                2365

Phe Gly Thr Lys Gly Val Arg Leu Glu Ser Ala Gln Asn Thr His Ser
                2370                2375                2380

Ser His Tyr Thr Leu Gln Gln Arg Asn Ser Gly Phe Ser Arg Ala Gly
2385                2390                2395                2400
```

-continued

Leu Gly Ile Ser Ile Gly Ser Ser Arg Ser Ser Glu Gln Gly Asp Thr
            2405                2410                2415

Gln Ala Thr Ser Ser Val Ala Asn Thr Val Ala Ala Leu Asn Gly Asn
        2420                2425                2430

Ile Thr Ile His Ser Ser Gln Gly Asn Val Asp Ala Ala Gly Ser Glu
    2435                2440                2445

Leu Leu Ala Ala Gly Asn Leu Ser Ala Ser Gly Val Asn Val Asp Leu
        2450                2455                2460

Gly Glu Val Tyr Asp Thr Leu Ser Thr His Glu Gln Gln Ser Ser Lys
2465                2470                2475                2480

Gln Ser Gly Leu Thr Ile Gly Phe Asn Ser Ala Leu Thr Ser Thr Ala
            2485                2490                2495

Gln Gly Val Ser Ala Asp Leu Lys Asn Arg Arg Asn Ala Pro Thr Gly
        2500                2505                2510

Arg Leu Ser Ser Leu Tyr Gly Trp Arg Ala Leu Ser Thr Ala Ala Ser
    2515                2520                2525

Ala Gly Tyr Gln Ala Tyr Gly Glu Ile Asp Thr Leu Arg Lys Thr Ser
        2530                2535                2540

Ser Leu Pro Ser Thr Phe Gln Ile Gly Val Ser Val Gly Thr Ser Ser
2545                2550                2555                2560

Ser Gln Ser Gln Ser Ser Met Ser Ala Arg Thr Ala Arg Gly Thr Gln
            2565                2570                2575

Leu Arg Ala Gly Gly Asp Ile Ser Ile Thr Ala Phe Gly Val Tyr Glu
        2580                2585                2590

Leu Asp Glu Lys Gly Asn Pro Thr Leu Lys Ala Gly Thr Gly Asn Ile
    2595                2600                2605

Asn Ala Thr Ala Ala Gln Phe Ser Ser His Asn Leu Asn Leu Thr Ala
        2610                2615                2620

Ala Gly Asn Leu Asp Ala His Ser Ala Gln Ser Thr Gln Glu Gln Thr
2625                2630                2635                2640

Ser Ser Gln Arg His Arg Ser Ala Ser Leu Gly Ala Lys Ile Gly Val
            2645                2650                2655

Thr Gly Gly Gly Thr Ser Val Ser Ala Asp Val Ala Arg Gly Arg Gly
        2660                2665                2670

Ser Ser Arg Gln Gln Ser Val Thr Gln Val Asp Thr Val Phe Thr Val
    2675                2680                2685

Ala Asn His Ala Thr Ile Ser Val Gly Gly Asp Ala Thr Met Lys Gly
        2690                2695                2700

Ala His Leu Asn Ala His Ser Ile Lys Ala Thr Ile Ala Gly Asn Leu
2705                2710                2715                2720

Asp Ile Thr Ser Leu Gln Asp Thr Leu Gln Ala Ser Ala Gln Gln Arg
            2725                2730                2735

Gln Ser Ser Ile Gly Gly Thr Trp Val Ile Asn Gly Ala Gly Ser Thr
        2740                2745                2750

Ala Thr Phe Ser Arg Asn Arg Gln Asp Ala Thr Gln Asp Tyr Ala Ser
    2755                2760                2765

Val Arg Asn Gln Ser Gly Leu Phe Ala Gly Ala Gly Gly Tyr Asp Ile
        2770                2775                2780

Thr Val Gly Gly His Ser Gln Phe Asn Gly Gly Ala Leu Thr Ser Thr
2785                2790                2795                2800

Ala Pro Gln Ala Leu Gln Ala Phe Ser Thr Asn Thr Ile Gly Tyr Thr
            2805                2810                2815

Asp Ile His Asn His Asn Ser Ala Asn Ala Ser Ala Ser Gly Ile Thr
        2820                2825                2830

```
Ile Gly Ser Asp Leu Val Ser Gly Leu Ser Lys Asn Pro Asn Gly
         2835                2840                2845

Thr Ala Asn Leu Gly Leu Ser Ile Tyr Ser Gly Leu Arg Ser Gly Ala
2850                2855                2860

Gly Gln Trp Met Ala Asn Ala Asp Arg Ser Val Asn Gln His Ser Thr
2865                2870                2875                2880

Thr Ala Ala Val Val Ser Ala Thr Asn Ile Gln Val Ser Asp Pro Gly
         2885                2890                2895

Ser Ser Gly Ala Leu Ala Thr Leu Arg Arg Asp Pro Ile Gly Ala His
         2900                2905                2910

Gln Ala Leu Ser Pro Thr Asp Leu Gly Ala Leu Gln Thr Asp Val Gln
         2915                2920                2925

Gln Arg Ser Gln Gly Gly Ala Leu Leu Ala Asp Ile Gly Arg Thr Met
         2930                2935                2940

Val Asp Gln Ser Ile Ser Asn Met Leu Thr Pro Thr Leu Asn Arg Val
2945                2950                2955                2960

Phe Cys Ile Gln Gln Pro Cys Thr Asn Asp His Val Ala Asn Asp Ala
         2965                2970                2975

Leu Val Lys Glu Arg Thr Glu Ala Leu Arg Gln Ala His Pro Gly Trp
         2980                2985                2990

Ser Asp Arg Lys Leu Arg Gln His Ala Val Ala Glu Leu Ala Leu Thr
         2995                3000                3005

Asp His Asn Ala Asn Arg Val Leu Asp Gln Asp Lys Val Lys Glu Met
3010                3015                3020

Ile Ala Asn Lys Gly Glu Gly His Tyr Ser Leu Gln His Asp Leu Leu
3025                3030                3035                3040

Ala Ser Gly Arg Trp Gly Ile Ser Arg Gly Ile Gly Asn Val Gln Val
         3045                3050                3055

Leu Pro Val Ser Leu Ala Asp Leu Ser Arg Leu Ser Asp Glu Glu Lys
         3060                3065                3070

Lys His Val Thr Leu Tyr Gly Asn Gly Ile Ser Asn Asp Ile His Arg
         3075                3080                3085

Ala Gly Glu Leu Ala Leu Gln Met Thr Pro Lys Asn Asp Asn Arg Gly
         3090                3095                3100

Asp Ile Ala Asn Ser Gly Glu Thr Tyr Gln Asn Thr Thr Tyr Gln Ala
3105                3110                3115                3120

Tyr Thr Lys Pro Thr His Gln Leu Gly Glu Leu Val Thr Ala Gly Ile
         3125                3130                3135

Glu Lys Leu Leu Glu Ile Thr Lys Ile Ala Ser Pro Ala Ser Arg Leu
         3140                3145                3150

Lys Ala Ala Ala Ala Lys Glu Leu Met Tyr Asn Ala Glu Asp Lys Lys
         3155                3160                3165

Tyr Thr Asn Pro Ile Tyr Leu Glu Gly His Ser Arg Gly Thr Met Lys
         3170                3175                3180

Leu Ser Asn Ala Leu Arg Val Leu Ala Ala Asp His Val Phe Ser Asp
3185                3190                3195                3200

Thr Leu Glu Ile Arg Ala Tyr Asn Pro Ala Ala Glu Gly Asn Arg Leu
         3205                3210                3215

Ala Glu Ala Ala Ala Leu Val Thr Lys Lys Pro Val Lys Thr Trp Ala
         3220                3225                3230

Pro Pro Lys Asp Phe Val Ala Asn Lys Ile Gly Gly Tyr Ala Gly Asn
         3235                3240                3245

Ala Thr Phe His Asp Leu Trp Glu Ile Phe Gln Thr Asn Tyr Ser Val
```

```
                    3250                3255                3260
His Ser Ser Gly Gly Thr Ala Leu Gly Ser Asp Ser Asn His Val
3265                3270                3275                3280

Asn Ala Pro Glu Leu Phe Ser Tyr Glu Gly Leu Asp Ile Lys Asp Met
                3285                3290                3295

Asn Ala Lys Arg Gln Gly Arg Thr Ile Gly Leu Leu Gln Gln Trp Gln
            3300                3305                3310

Lys Thr Pro Ser Pro Glu Asn Pro Val Ala Thr Gln Leu Thr Gln Leu
        3315                3320                3325

Gln Arg Leu Leu Trp Gln Ser Gly Gln Trp Gln Gln Leu Asp Asn
    3330                3335                3340

Thr Pro Gly Leu Leu Thr Arg Pro Thr Pro Thr Thr Pro Asp Ala Pro
3345                3350                3355                3360

Ser Ala Arg Gln Gln Gln Leu Gln Gln Leu Arg Gln Ser Leu Thr Pro
                3365                3370                3375

Tyr

<210> SEQ ID NO 4
<211> LENGTH: 3489
<212> TYPE: PRT
<213> ORGANISM: Xylella fastidiosa

<400> SEQUENCE: 4

Met Asn Lys Asp Leu Tyr Arg Leu Ile Tyr Asn Arg Ala Leu Arg Leu
1               5                   10                  15

Trp Gln Val Ala Ser Glu Arg Thr Thr Ala Pro Gly Gly Thr Pro Gly
            20                  25                  30

Pro Ser Pro Thr Ala Gln Arg Pro Ala Arg Ala Cys Leu His Pro Ile
        35                  40                  45

Pro Phe Ala Leu Trp Leu Ser Leu Gly Trp Val Ser Ile Thr Gly Met
    50                  55                  60

Ala Thr Ala Gln Val Val Ala Asp Pro His Ala Pro Gly Gln Gln Arg
65                  70                  75                  80

Pro Thr Ile Leu Thr Ala Pro Asn Gly Ala Pro Leu Ile Asn Ile Gln
                85                  90                  95

Thr Pro Ser Pro Ala Gly Val Ser Arg Asn Thr Tyr Gln Gln Phe Asp
            100                 105                 110

Ile Thr Pro Gln Gly Ala Ile Leu Asn Asn Ala Arg Thr Pro Thr Gln
        115                 120                 125

Thr His Leu Ala Gly Thr Val Gln Gly Asn Pro Trp Leu Ala Ala Gly
    130                 135                 140

Thr Ala Lys Ile Ile Leu Asn Glu Val Asn Ser Pro Thr Ser Thr Gln
145                 150                 155                 160

Leu His Gly Thr Met Glu Val Ala Gly Ala Arg Ala Gln Leu Ile Ile
                165                 170                 175

Ala Asn Pro Ser Gly Ile Thr Cys Asn Gly Cys Gly Val Ile Asn Ala
            180                 185                 190

His Gln Leu Thr Leu Thr Thr Gly Thr Pro Ile Phe Asn Ala Arg Gly
        195                 200                 205

Ala Leu Asp His Tyr Arg Val Gln Gly Gly Ala Ile Gln Ile Asp Gly
    210                 215                 220

Leu Gly Leu Asp Ser His Ser Thr Asp Tyr Thr Ala Leu Ile Ala Arg
225                 230                 235                 240

Thr Val Gln Leu Asn Ala Gly Leu Trp Ala His Thr Leu Gln Thr Thr
                245                 250                 255
```

```
Thr Gly Pro Ala Thr Val Ala Leu Asp Gly His Pro Thr Ala Ser Leu
            260                 265                 270

Pro Ala Pro Pro Gly Asp Arg Pro Thr Val Ala Leu Asp Val Ser Ala
        275                 280                 285

Leu Gly Gly Met Tyr Ala Gly Lys Ile Thr Leu Ile Gly Thr Glu His
        290                 295                 300

Gly Leu Gly Val Arg Asn Ala Gly Gln Leu Ser Ala Thr Ser Ala Pro
305                 310                 315                 320

Leu Thr Val Thr Val Asp Gly Leu Leu Glu Asn Thr Gly Arg Leu Gln
            325                 330                 335

Ser Ala Thr Asp Thr Gln Leu Asn Ala Thr Ala Glu Val Asn Asn Ser
            340                 345                 350

Gly Leu Ile Ser Ala Ala Gln Thr Leu Thr Leu His Thr Pro Thr Thr
        355                 360                 365

Ile Asp Asn Arg Ser Gly Thr Leu Asn Ala Ala Arg Leu Asp Ile Thr
    370                 375                 380

Gly Ala Arg Leu Asp Asn Arg Gly Gly His Ile Gln Gln Thr Gly Leu
385                 390                 395                 400

Gln Pro Leu Thr Leu Gln Thr Gln His Leu Asp Asn Gln Asp Gln Gly
            405                 410                 415

Arg Leu Gly Val Leu Asp Thr Pro Ala Pro Ala Ser Pro Ala Thr Pro
        420                 425                 430

Thr Val Thr Ala Pro Ile Ser Asn Ala Pro Thr Val Thr Ala Pro
        435                 440                 445

Pro Ala Thr Asp Pro Thr Thr Ser Pro Val Ala Pro Thr Val Pro His
    450                 455                 460

Leu Ala His Gly Thr Leu Thr Leu Thr Gln Thr Ile Asp Asn Arg Gly
465                 470                 475                 480

Gly His Ile Thr Ala Gly Gly Ala Ile Asp Ala Ile Leu Thr Asp Leu
            485                 490                 495

Asp Asn Arg Asp Gly Thr Ala Ala Leu Asn Arg Leu Thr Leu Gln Gly
            500                 505                 510

Gln Arg Leu Asp Asn Gln His Gly Ile Leu Thr Leu Ala Thr Asp Ala
        515                 520                 525

Thr Ile His Thr His Thr Leu Asn Asn Ala Ala Gly Gln Leu His Ala
    530                 535                 540

Asn Gly Thr Leu Asp Leu Thr Ala Asp Thr Phe Ser Asn Gln Asn Gly
545                 550                 555                 560

Gln Leu Leu His Thr Gly Ser Gln Asn Ala Thr Leu Thr Ile Thr Asp
            565                 570                 575

Leu Leu Asp Asn Gln His Gly Ile Ile Ala Ser Ala Ala Asn Leu Leu
        580                 585                 590

Thr Leu Lys Thr Asp His Leu Asn Asn Ala Ala Gly Gln Leu His Ala
    595                 600                 605

Asn Gly Ala Leu Asp Leu Thr Ala Gln Arg Phe Ser Asn Gln Asn Gly
610                 615                 620

Gln Leu Leu His Thr Gly Ser Gln Asn Ala Thr Leu Thr Ile Ala Asn
625                 630                 635                 640

Leu Leu Asp Asn Gln His Gly Leu Val Ala Ser Ala Ala Asn Ala Leu
            645                 650                 655

Thr Leu His Thr Gly His Leu Asn Asn Asp Ala Gly Gln Phe Gln Thr
            660                 665                 670

Asn Gly Ala Leu Asp Leu Thr Ala Gln Arg Phe Ser Asn Gln His Gly
```

```
              675                 680                 685
Gln Phe Leu His Asn Ser Pro Gln Ser Ala His Leu Arg Ile Asp Gly
690                 695                 700
Gln Leu Asp Asn Gln Gln Gly Val Leu Ala Ser Asn Ala Ala Glu Leu
705                 710                 715                 720
Thr Leu Glu Thr Gly Gln Phe Asn Asn Asp Ser Gly Thr Leu Gln Gln
                725                 730                 735
Ser Gly Gln Gly Thr Leu His Ile Asp Ala Ala Thr Leu Thr Gly His
            740                 745                 750
Gly Gly Thr Leu Thr Ser Gln Gly Ala Leu Thr Leu Thr Gly Thr His
        755                 760                 765
Thr Asp Leu Ser His Ala Thr Thr Ala Gln His Ile Thr Ile His
    770                 775                 780
Thr Asp Asp Leu Thr Thr Ala Gly Gly His Leu Thr Ala Tyr Gly Glu
785                 790                 795                 800
His Thr Leu Gln Leu Asn Ala Arg Thr Arg Ile Asp Asn Thr Ala Gly
                805                 810                 815
Thr Ile Ala Thr Asn Gly Ser Leu Asp Leu His Thr Ala Ala Leu Asp
            820                 825                 830
Asn Thr Gly Gly Thr Leu His Ser Thr Ala Thr Gly Pro Asn Arg Leu
        835                 840                 845
Asp Ile Thr His Thr Leu Thr Asn Thr Ala Gly His Leu Leu Leu Asn
    850                 855                 860
Gly Pro Thr Thr Leu Thr Thr Gly Thr Trp Thr Asn Thr Gly Gly Gln
865                 870                 875                 880
Leu Gln Ile Thr Gly Pro Ala Thr Leu His Ala Thr Leu Asp Asn
                885                 890                 895
Arg Gly Gly Ile Leu His Thr Ala Thr Gly Pro Leu Asp Leu Arg Val
            900                 905                 910
Thr Gly Thr Ile Asn Asn Gln Asp Asn Gly Ile Leu Ser Ser Thr Ala
        915                 920                 925
Ala Leu Thr Leu Thr Ala Ala Ser Leu His Asn Gln His Gly Thr Leu
    930                 935                 940
Asp Ala Ala Gly Pro Ala His Leu Thr Leu Thr Gly Leu Leu Asp Asn
945                 950                 955                 960
Thr Ala Gly Leu Leu Gln Thr Ala His Thr Leu Trp Leu Thr Ser Ala
                965                 970                 975
Gly Leu Thr Asn Arg Ser Gly Thr Leu Thr Ala Ala Leu Thr Leu
            980                 985                 990
Asp Thr Gln Ala His Thr Leu Asp Asn Thr Ser Gly Arg Leu Gly Thr
        995                 1000                1005
Thr Thr Gly Asn Leu Thr Leu His Thr Gly Leu Leu Asp Asn Thr Ala
    1010                1015                1020
Gly Leu Leu Gln Thr Ala Ala Thr Leu Thr Ile Asp Thr Gly Ala Ala
1025                1030                1035                1040
Pro Leu Thr Asn Arg Asp Gly Gly Thr Leu Leu Ala Ala Asp Thr Leu
                1045                1050                1055
Asp Leu His Thr Thr Leu Asp Asn Arg Gly Gly Thr Ile Asp Ser
            1060                1065                1070
Gln Thr Ala Thr His Leu His Thr Thr Thr Ile Asp Asn Thr Thr Ala
        1075                1080                1085
Gly His Ile Ser Ser Asn Gly Thr Leu Gln Ile Asp Gly Thr Thr Leu
    1090                1095                1100
```

```
Thr Asn Thr Gly Gly Arg Leu His Ser Gly Gly Asp Thr Arg Leu His
1105                1110                1115                1120

Leu Gln Asp Thr Leu Asn Asn His Asp Gly Arg Ile Thr Ala Ala Gly
            1125                1130                1135

Thr Leu Asp Ile Thr Thr Thr Thr Leu Asp Asn His Ser Thr Pro Leu
        1140                1145                1150

Thr Ala Pro Pro Ala Thr Gln Thr Arg Ala Pro Thr Gly Ala Pro Asp
    1155                1160                1165

Asn Gly Leu Tyr Ala Thr His Ile Gln Ile Ala Ser Thr Thr Leu Asp
1170                1175                1180

Asn Thr Ala Gly Thr Leu Ser Ala Ala Gln Asn Leu Thr Leu Thr Leu
1185                1190                1195                1200

Ser Asp Thr Leu Thr Asn Thr Ala Gly His Leu Ser Ala Gly Ala Thr
                1205                1210                1215

Leu Asp Leu Thr Ala Asp His Leu Ser Asn His Thr Gly Thr Leu Leu
            1220                1225                1230

Ser Gly Ala Ser Gln Thr Leu His Leu His Arg Leu Thr Gly Asp Gly
        1235                1240                1245

Arg Leu His Ala Gly Asn Ala Leu Thr Leu Thr Leu Gln Asp Ser Leu
    1250                1255                1260

Asp Thr Ala Gly Thr Leu Ser Ala Thr Gly Leu Leu Thr Leu Thr Thr
1265                1270                1275                1280

Ala Gly Asp Leu Thr Asn Arg Gly Leu Ile Gln Ala Ala Asp Leu Thr
                1285                1290                1295

Ala Gln Ala Arg Asp Ile Thr Thr Ala Thr Gly Gln Leu Leu Thr
            1300                1305                1310

Thr Gly His Thr His Leu Thr Ala Thr Gly Thr Leu Asn Asn Ser Gly
        1315                1320                1325

His Leu Gln Ala Ala Asp Leu Thr Ala Gln Ala His Asp Ile Thr Thr
    1330                1335                1340

Thr Ala Thr Gly Gln Leu Leu Thr Thr Gly His Thr His Leu Thr Ala
1345                1350                1355                1360

Thr Gly Thr Leu Asn Asn Ser Gly His Leu Gln Ala Ala Asp Leu Thr
                1365                1370                1375

Ala Gln Ala Asn Thr Ile Thr Asn Thr Gly Thr Phe Leu Ala Thr Ser
            1380                1385                1390

His Ala Thr Leu Thr Ala Thr Asp Thr Leu Thr Asn Ser Gly Leu Leu
        1395                1400                1405

Gln Ala Ala Asp Leu Thr Ala Gln Ala Asn Thr Ile Thr Asn Thr Ala
    1410                1415                1420

Thr Gly Arg Leu Leu Thr Thr Ala His Thr Gln Leu Thr Ala Thr Asp
1425                1430                1435                1440

Thr Leu Thr Asn Ser Gly Leu Val His Ala Gly Asp Leu Thr Val His
                1445                1450                1455

Ala Arg Asp Ile Thr Asn Thr Ala Thr Gly Gln Leu Ile Ala Ser Asn
            1460                1465                1470

Leu Ala Gln Leu Thr Ala Thr Ala Thr Leu Thr Asn Arg Gly Leu Ile
        1475                1480                1485

Asp Ala Phe Thr Thr His Leu Ser Ala Pro Ile Asp Asn Leu Gly
    1490                1495                1500

Thr Gly Arg Leu Tyr Gly Asp His Ile Ala Leu Gln Ala His Thr Leu
1505                1510                1515                1520

Thr Asn Arg Asp Glu Thr Ser Asp Gly His Thr His Thr Ala Thr Ile
                1525                1530                1535
```

```
Ala Ala Arg Glu Arg Leu Asp Ile Gly Ala Asp Thr Leu Arg Asn Thr
        1540                1545                1550

Ala Asn Ala Met Ile Leu Ser Asp Gly Asp Ala Ala Ile Gly Ala Thr
        1555                1560                1565

Leu Asp Asn Thr Leu His Ala Thr Gly Ile Ala Thr Leu Ile Asp Asn
        1570                1575                1580

Arg Ser Ala Thr Ile Asp Ile Thr Gly Thr Leu Asn Ile Thr Thr Thr
1585                1590                1595                1600

Thr Leu Asn Asn Ile Arg Glu Asn Val His Ile Ala His Ala Pro Asp
        1605                1610                1615

Val Val Thr Glu Thr Pro Met Tyr Gln Pro His Trp Arg Lys Asn Lys
        1620                1625                1630

Pro Asn Gly Gly Ser Gly Asp Phe Arg Leu Ser Ser Asn Tyr Asp Ala
        1635                1640                1645

His Asp Ile Tyr Tyr Leu Asn Pro Ala Asp Ile Leu Glu Asp Thr Pro
        1650                1655                1660

Tyr Ile Thr Pro Asp Gly Gln Lys Ile His Arg Ala Ile Val Arg Leu
1665                1670                1675                1680

Thr Pro Gln Thr Ser Ala Tyr Phe Tyr Ala Arg Gly Gly Leu His Ala
        1685                1690                1695

Ser Gln Ala Glu Arg Arg Arg Leu Asp Leu Thr Ala Arg Thr Gly Asp
        1700                1705                1710

Ser Val Val Leu Tyr Tyr Thr Asp Arg Gln Asp Lys Gln Pro Asn Pro
        1715                1720                1725

Asp His Val Ala Ala Ala Thr Asn Asp Ser Ala Phe Ile Gly Leu
        1730                1735                1740

Asp Ala Pro Gln Gln Asn Glu Arg Leu Lys Ile Val Pro Ile Thr Tyr
1745                1750                1755                1760

Ala Pro Gly Asp Asp Arg Leu Thr Tyr Asp Pro Thr Tyr Gly Thr Cys
        1765                1770                1775

Thr Asp Asp Cys Val Arg Leu Val Thr Trp His Asp Tyr Thr Asp Pro
        1780                1785                1790

Asp His Thr Leu Ile Asp Met Arg Arg Gly Pro Asn Asp Val Asp Asp
        1795                1800                1805

Asn Glu Arg Glu Arg His Ala Thr Arg Thr Thr Gln Gln Glu Ile Leu
        1810                1815                1820

Asn Pro Asp Ala Gly Ala Pro Ala Leu Ile Gln Ser Gly Gly Thr Met
1825                1830                1835                1840

Arg Ile Asp Val Gly Tyr Leu Tyr Asn His Tyr Ala Asp Leu Leu Ala
        1845                1850                1855

Gly Gly Asp Gln Thr Ile Val Gly Leu Pro Pro His Pro Thr Lys Glu
        1860                1865                1870

Thr Ala Asp Asp Glu His Lys Tyr Asn Arg Ala Leu Leu Ile Asp Asn
        1875                1880                1885

Arg Ala Leu Gln Leu Ser Arg Thr Asp Arg Phe Gln Asn Ile Ser Thr
        1890                1895                1900

Thr Tyr Arg Gly Lys Asp Ser Ala Pro Trp Ser Asn Glu Ser Arg Thr
1905                1910                1915                1920

Thr Pro Thr Thr Gln Ile Gly Gly Arg Ile Thr Ser Gly Gly His Gln
        1925                1930                1935

His Ile Ala Ala Gln Thr Phe Asn Asn Val Thr Asp Ser Thr His Ala
        1940                1945                1950

Pro Glu Pro Ile Gln His Val Thr Tyr Asn Pro Ser Thr Gln Thr Leu
```

-continued

```
                1955                1960                1965

Thr Ile Ala Asp Gly His Ile Thr Val Thr Asp Thr Pro Ser Leu
    1970                1975                1980

His Thr Val Ser Leu Ala Asp Asn Gly Phe Ser His Gly Gln Glu Leu
1985                1990                1995                2000

Thr Tyr Ile Pro Glu Lys Ser Ile Thr Thr Pro Asn Ala Pro Ile Arg
                2005                2010                2015

Asp Pro Ala Ala Pro Pro Arg Arg His Arg His Pro His Arg Pro Pro
                2020                2025                2030

His Pro Ala Gln Gln Gln Pro Leu His His Ser Pro Arg His Arg His
            2035                2040                2045

Pro His His His Arg Pro Pro Leu Tyr Pro Arg Pro Pro Leu His Gln
        2050                2055                2060

Arg Arg Gln Pro Thr Pro Arg Pro Gly Arg Pro Arg His Pro Pro Gln
2065                2070                2075                2080

Thr Pro Arg Arg Arg Leu Leu Arg Thr Thr Pro His Pro Arg Thr Asn
                2085                2090                2095

Arg Pro Thr His Arg Pro Pro Pro Gly Arg Leu His Arg Arg Arg
                2100                2105                2110

Pro Pro Ile Pro Arg Pro Pro Gly Arg Arg Pro His Arg Arg Gln Thr
            2115                2120                2125

Ala Pro Thr Ala Pro Arg His Cys Pro Gln Cys Arg Pro Asn Gly Pro
            2130                2135                2140

Thr His Gln Arg His Arg Leu Ala Arg Pro Thr Arg Arg Pro Pro Ala
2145                2150                2155                2160

Arg Arg His His His Arg Arg Pro Arg Pro Pro Leu Pro Ala Pro
                2165                2170                2175

Pro His Arg Arg Pro His Pro Arg Arg Pro Pro Gly Gly Arg Gln
            2180                2185                2190

His His His Gln Arg Pro His Pro His Gln Arg His His Arg Pro
            2195                2200                2205

Arg Pro His Gln His Gln His Pro His His Gly Pro Thr Arg Arg Pro
        2210                2215                2220

Pro Tyr Arg Arg Arg His Gln His Pro His His Arg Arg Leu His Gln
2225                2230                2235                2240

Pro Gly Arg Thr Ile His Arg Arg Arg Leu Pro Gln Ser Pro Cys Pro
                2245                2250                2255

Arg Gln Leu Pro Cys Gln His Pro Pro Arg Arg His His Pro Arg His
                2260                2265                2270

Pro Pro Pro Gln Arg Asp Arg Thr Gly Pro Thr Gly Arg Leu His Arg
            2275                2280                2285

His Arg Pro Arg Cys Leu Pro Trp Leu Glu His Arg Pro Ser His Asp
            2290                2295                2300

Pro Thr Ser Arg Cys His Gln Gln His Arg His Arg Leu His Leu Pro
2305                2310                2315                2320

Gln Ser His Arg Pro Pro Thr Pro Arg His Pro Gln His Pro Pro Gln
                2325                2330                2335

Arg His His Pro Val Gly Pro Pro Gln Gln Pro Pro Gln Pro His Arg
            2340                2345                2350

His Arg Thr Arg His Gln His Pro Gln Arg Arg His Pro Thr Gln
            2355                2360                2365

Gln Arg Pro Arg His Gln Pro Ala Cys Arg His Pro Pro Gln His Pro
        2370                2375                2380
```

-continued

Arg His Arg Gln Arg Pro Gly His Arg Gln Arg His His Tyr Ala Arg
2385                2390                2395                2400

Gly His Pro Pro Ile His Gln Pro Arg Pro Gln Gln Thr Gln Arg Pro
            2405                2410                2415

Pro Gln Gln Pro His His His Pro Arg Arg Pro Thr Thr Asp Pro
        2420                2425                2430

Gly His Glu Gln His Pro Gln Arg His Ser Pro Arg Gln Arg Gln Gln
        2435                2440                2445

His His Arg His Arg Gln Pro Pro Pro Phe Arg Cys Arg His Leu His
    2450                2455                2460

Ala Gly Gln Arg Arg Pro His Pro Pro Ser Arg His Gln His His Pro
2465                2470                2475                2480

Ile His Leu Leu Arg Thr His Gln Thr Lys Trp Pro His Pro Gln Arg
            2485                2490                2495

Arg Arg Leu Pro His Pro Gly Gln Pro Lys Pro Ala His Arg Gln His
        2500                2505                2510

His His Ser His His His His Arg Leu Pro His Arg His Gln Arg
    2515                2520                2525

Gln Cys Asp Pro Ala Gly Gly Arg Pro Leu Pro Thr Asp Arg Gln Arg
        2530                2535                2540

Arg Pro Val Pro Arg Arg His Arg His Pro Arg Gln Lys Ser Arg His
2545                2550                2555                2560

His Pro Ser Pro Pro His Gln Pro His His Pro Thr His Arg His Pro
            2565                2570                2575

Pro Lys Arg Pro His Arg Arg Pro Gln His Pro Pro Asp Cys Arg Cys
        2580                2585                2590

Pro Asp Arg Pro Ala Asn Ala Thr Arg Arg Ser Gln Arg Arg Pro
        2595                2600                2605

Pro Pro Pro Arg Pro Gly Arg Pro His His Arg Pro Gly Arg Gln Lys
    2610                2615                2620

His His Cys Arg Ala Pro Arg Pro Pro Arg Pro Gly Arg Pro Gln Arg
2625                2630                2635                2640

Leu Pro His Pro Trp Pro Gln His Thr Arg Gln His His His Asp His
            2645                2650                2655

His His His Arg Arg Arg Leu Gln Arg Gln Arg Arg Arg Pro His
        2660                2665                2670

Gln Arg His Arg Arg Arg Ser Leu His Pro His His Pro Arg Gln Pro
        2675                2680                2685

Arg Pro Arg Arg Gln His Asp Leu Pro Gln Ser Arg Trp Arg His Arg
    2690                2695                2700

Pro Thr Gly Arg Arg Gln His His His Gln Arg Pro Ser Lys Pro Arg
2705                2710                2715                2720

Pro Gln Arg Arg Cys Arg Arg Gly Arg Glu Pro Arg Leu Gln Arg His
            2725                2730                2735

Gln Cys Arg Pro His Arg Pro Arg Gln His Leu His Arg Gln Arg Pro
        2740                2745                2750

Val Tyr Arg Pro His Leu Asp Gln Gln Pro Arg Arg Arg Gln Pro
        2755                2760                2765

Thr Asp His Ser Arg Arg Pro Pro His Glu Arg Arg His Trp His
    2770                2775                2780

Arg Gln Thr Arg His Cys Arg His Cys Trp Gln Pro His Pro Lys
2785                2790                2795                2800

Pro Pro Arg His Pro Pro Leu Pro Gln Gln Arg Pro Gln Pro Trp Arg
            2805                2810                2815

```
Gln Pro His Arg Arg Arg Arg Gln Arg Gln Arg Gln Pro Gln Gln
            2820                2825                2830

Pro Asn His Pro Gln Arg Leu Arg Gln Arg His Arg Thr Lys Arg Pro
            2835                2840                2845

Val Tyr Trp Arg Trp Arg Leu His His Arg Trp Arg Pro Asp Pro Pro
            2850                2855                2860

Tyr Arg Arg Arg His His Leu Gln Gln His Arg His Pro Gln Arg Pro
2865                2870                2875                2880

Glu His Pro Gly His Arg His Pro Asp Pro Ala Arg His Lys Pro Arg
            2885                2890                2895

His Leu His Arg His Pro Ser Gln Pro Gly Arg Arg Leu Gln Pro Gln
            2900                2905                2910

Arg Arg His Arg Arg His Arg Pro Thr Arg Pro Arg Arg His Arg His
            2915                2920                2925

Pro Gly Ser Trp His His Leu Thr His Pro Gln Arg Pro Gln Arg Cys
            2930                2935                2940

Pro Ser Trp Arg His Asp Arg Gln Arg Gln Pro Gln His His Leu
2945                2950                2955                2960

Gln Arg His Gln Pro Arg Arg Pro His His Pro Arg Pro Arg Arg Pro
            2965                2970                2975

Thr Arg Pro His Arg Pro His Arg Arg Pro Asp His Arg Arg Pro Gln
            2980                2985                2990

Pro Arg His Pro His Arg His Arg His Gln Arg Pro His Pro His
            2995                3000                3005

Leu Arg Thr Thr His Gln Arg Arg Leu His Arg His Arg Pro Thr Thr
            3010                3015                3020

Gly Asn Arg His Leu His Gln Gln Pro Cys Arg Arg Ser Arg Ser Gln
3025                3030                3035                3040

Asn Pro Pro Ser His Arg Arg Pro Ser Arg Thr Arg Pro His Gln
            3045                3050                3055

Arg Ile Gln Pro Thr Ala Ala Asn Ile Thr Pro Ser His His Pro His
            3060                3065                3070

Gln Arg Ser Pro Gly His Gln Arg Arg Leu Gly Thr Gly Arg His Leu
            3075                3080                3085

Pro Pro Asn His His Arg Leu Ser Arg Arg Cys Gln Arg Gln Arg Gln
            3090                3095                3100

Arg Cys Gln Gln Arg Pro Cys Gln Thr His Asp Arg Gln Leu Arg Pro
3105                3110                3115                3120

Thr Thr Arg Arg His Arg His Trp Pro Leu Gly Gly His Arg Pro Thr
            3125                3130                3135

Asp Arg Arg Gln Pro Pro Thr Arg Pro Pro Cys Pro Ala Gly Leu
            3140                3145                3150

Arg Arg Cys Cys Gly Gln Pro Thr Thr Leu Gln Gln Trp Arg Pro Arg
            3155                3160                3165

Arg Arg Arg Leu Gln Arg Pro His Gly Ile Ile Arg Pro Pro Arg
            3170                3175                3180

Arg His Arg Pro Arg Pro Arg Ser Gln Thr Gln Pro His Tyr Leu His
3185                3190                3195                3200

Arg His Arg His Arg Gln His His Ala His Arg Cys Gly His Arg His
            3205                3210                3215

Pro Cys Arg His Arg Cys Arg Gly Gln Leu Val Gly Gly Gln Thr Ile
            3220                3225                3230

Arg Ser Asn Gly Lys Arg Gly Ala Gly Arg Tyr Gly Glu Arg Gln Arg
```

```
                    3235                3240                3245
Ser Leu Gly Arg Gly Glu Ser Lys Ser Glu Val Ala Asp Gln Cys Pro
        3250                3255                3260
Pro Arg Thr His Cys Trp Thr Leu Lys Arg Leu Lys Gly Val Arg His
3265                3270                3275                3280
Gln Gln Tyr Gln Arg Ala Gly Ala Leu Asp Pro Ala Ser Gly Gly Cys
                3285                3290                3295
Leu Ser Val Gly Glu Asn Pro Tyr Pro Pro Lys Ile Thr Gly Ala Ile
        3300                3305                3310
Arg Ala Arg Arg Ser Arg Thr Ala Gln Gly Phe Ser His Val Gly Ser
        3315                3320                3325
Ser His Cys Trp Arg Arg Ser Thr Cys Gln Ala Val Trp Arg Arg Ser
        3330                3335                3340
Arg Leu Ser Asp Arg Gly Cys Arg Leu Cys Ile Gly Cys Gly Arg His
3345                3350                3355                3360
Arg Gln Ser Gly Arg Asp Pro Arg Arg Ser Arg His Gln Ser Gln Arg
                3365                3370                3375
Cys Leu Gly Gly Asp Gly Tyr Phe Gln Ser Gln Ala Val Gln Arg His
        3380                3385                3390
Cys Gln Arg Arg Thr Arg Ser Thr Asp Ala Asp Arg Ser Pro Gln Arg
        3395                3400                3405
Pro Gly Phe Asn Pro Lys Thr Ala Trp Ser Ile His Arg Val Ala Ala
        3410                3415                3420
Gly Gly Ile Ser Asn Ser Leu Ser Lys Leu Lys Arg Ile Cys Phe Phe
3425                3430                3435                3440
Gly Phe Lys Ser Gln Ser His Thr Ala Arg Leu Cys Arg Arg Glu Ser
                3445                3450                3455
Gly Cys Glu Gly Ala Ile Arg Ser Ile Gln Ser Glu Asn Gln Arg Val
        3460                3465                3470
Cys Thr Ala Ile Gly Gly Gly Cys Ala Phe Lys Gly Asp Glu Gln Lys
        3475                3480                3485
Met
```

<210> SEQ ID NO 5
<211> LENGTH: 3457
<212> TYPE: PRT
<213> ORGANISM: Xylella fastidiosa

<400> SEQUENCE: 5

```
Met Ala Ser Glu Leu Ala Thr Ala Ser Gly Gly Thr Pro Gly Pro Ser
 1               5                  10                  15
Pro Thr Ala Gln Arg Pro Ala Arg Ala Cys Leu His Pro Ile Pro Phe
            20                  25                  30
Ala Leu Trp Leu Thr Leu Gly Trp Val Thr Ile Thr Gly Ile Ala Thr
        35                  40                  45
Ala Gln Val Val Ala Asp Pro His Ala Pro Gly Gln Gln Arg Pro Thr
    50                  55                  60
Val Leu Ala Ala Pro Asn Gly Thr Pro Leu Ile Asn Ile Gln Thr Pro
65                  70                  75                  80
Ser Pro Ala Gly Val Ser Arg Asn Thr Tyr Gln Gln Phe Asp Ile Thr
                85                  90                  95
Pro Gln Gly Ala Ile Leu Asn Asn Ala Arg Thr Pro Thr Gln Thr His
            100                 105                 110
Leu Ala Gly Thr Val Gln Gly Asn Pro Trp Leu Ala Ala Gly Thr Ala
        115                 120                 125
```

```
Lys Ile Ile Leu Asn Glu Val Asn Ser Ser Thr Pro Ser Gln Leu His
    130                 135                 140

Gly Ser Met Glu Val Ala Gly Ala Arg Ala Gln Leu Ile Ile Ala Asn
145                 150                 155                 160

Pro Ser Gly Ile Thr Cys Asn Gly Cys Gly Val Ile Asn Ala His Gln
            165                 170                 175

Leu Thr Leu Thr Thr Gly Thr Pro Ile Phe Asn Ala Arg Gly Ala Leu
        180                 185                 190

Asp His Tyr Arg Val Gln Gly Ala Ile Gln Ile Asp Gly Leu Gly
        195                 200                 205

Leu Asp Ser Arg Ser Ala Asp Tyr Thr Ala Leu Ile Ala Arg Thr Val
    210                 215                 220

Gln Leu Asn Ala Gly Leu Trp Ala His Thr Leu Gln Thr Thr Thr Gly
225                 230                 235                 240

Pro Ala Thr Val Ala Leu Asp Gly His Pro Thr Ala Ser Leu Pro Val
                245                 250                 255

Thr Pro Gly Asp Arg Pro Thr Val Ala Leu Asp Val Ser Ala Leu Gly
            260                 265                 270

Gly Met Tyr Ala Gly Lys Ile Thr Leu Ile Gly Thr Glu His Gly Leu
        275                 280                 285

Gly Val Arg Asn Ala Gly Gln Leu Ser Ala Thr Ser Ala Pro Leu Thr
    290                 295                 300

Val Thr Val Asp Gly Leu Leu Glu Asn Thr Gly Arg Leu Gln Ser Ala
305                 310                 315                 320

Thr Asp Thr Gln Leu Asn Ala Thr Ala Glu Val Asn Ser Gly Leu
                325                 330                 335

Ile Ser Ala Ala Gln Thr Leu Thr Leu His Thr Pro Thr Thr Ile Asp
            340                 345                 350

Asn Arg Ser Gly Thr Leu Asn Ala Ala Arg Leu Asp Ile Thr Gly Ala
        355                 360                 365

Arg Leu Asp Asn Arg Gly Gly His Ile Gln Gln Thr Gly Leu Gln Pro
    370                 375                 380

Leu Thr Leu Gln Thr Gln His Leu Asp Asn Gln Asp Gln Gly Arg Leu
385                 390                 395                 400

Gly Val Leu Asp Thr Pro Ala Pro Ala Ser Pro Ala Thr Pro Thr Val
                405                 410                 415

Thr Ala Pro Ile Ser Asn Ala Pro Pro Thr Val Thr Ala Pro Pro Ala
            420                 425                 430

Thr Asp Pro Thr Thr Ser Pro Val Ala Pro Thr Val Pro His Leu Ala
        435                 440                 445

His Gly Thr Leu Thr Leu Thr Gln Thr Ile Asp Asn Arg Gly Gly His
    450                 455                 460

Ile Thr Ala Gly Gly Ala Ile Asp Ala Ile Leu Thr Asp Leu Asp Asn
465                 470                 475                 480

Arg Asp Gly Thr Ala Ala Leu Asn Arg Leu Thr Leu Gln Gly Gln Arg
                485                 490                 495

Leu Asp Asn Gln His Gly Ile Leu Thr Leu Ala Thr Asp Ala Thr Ile
            500                 505                 510

His Thr His Thr Leu Asn Asn Ala Ala Gly Gln Leu His Ala Asn Gly
        515                 520                 525

Thr Leu Asp Leu Thr Ala Asp Thr Phe Ser Asn Gln Asn Gly Gln Leu
    530                 535                 540

Leu His Thr Gly Ser Gln Asn Ala Thr Leu Thr Ile Thr Asp Leu Leu
```

```
                545                 550                 555                 560
Asp Asn Gln His Gly Ile Ile Ala Ser Ala Ala Asn Leu Leu Thr Leu
                565                 570                 575
Lys Thr Asp His Leu Asn Asn Ala Ala Gly Gln Leu His Ala Asn Gly
                580                 585                 590
Ala Leu Asp Leu Thr Ala Gln Arg Phe Ser Asn Gln Asn Gly Gln Leu
                595                 600                 605
Leu His Thr Gly Ser Gln Asn Ala Thr Leu Thr Ile Ala Asn Leu Leu
                610                 615                 620
Asp Asn Gln His Gly Leu Val Ala Ser Ala Asn Ala Leu Thr Leu
625                 630                 635                 640
His Thr Gly His Leu Asn Asn Asp Ala Gly Gln Phe Gln Thr Asn Gly
                645                 650                 655
Ala Leu Asp Leu Thr Ala Gln Arg Phe Ser Asn Gln His Gly Gln Phe
                660                 665                 670
Leu His Asn Ser Pro Gln Ser Ala His Leu Arg Ile Asp Gly Gln Leu
                675                 680                 685
Asp Asn Gln Gln Gly Val Leu Ala Ser Asn Ala Ala Glu Leu Thr Leu
                690                 695                 700
Glu Thr Gly Gln Phe Asn Asn Asp Ser Gly Thr Leu Gln Gln Ser Gly
705                 710                 715                 720
Gln Gly Thr Leu His Ile Asp Ala Ala Thr Leu Thr Gly His Gly Gly
                725                 730                 735
Thr Leu Thr Ser Gln Gly Ala Leu Thr Leu Thr Gly Thr His Thr Asp
                740                 745                 750
Leu Ser His Ala Thr Thr Thr Ala Gln His Ile Thr Ile His Thr Asp
                755                 760                 765
Asp Leu Thr Thr Ala Gly Gly His Leu Thr Ala Tyr Gly Glu His Thr
                770                 775                 780
Leu Gln Leu Asn Ala Arg Thr Arg Ile Asp Asn Thr Ala Gly Thr Ile
785                 790                 795                 800
Ala Thr Asn Gly Ser Leu Asp Leu His Thr Ala Ala Leu Asp Asn Thr
                805                 810                 815
Gly Gly Thr Leu His Ser Thr Ala Thr Gly Pro Asn Arg Leu Asp Ile
                820                 825                 830
Thr His Thr Leu Thr Asn Thr Ala Gly His Leu Leu Leu Asn Gly Pro
                835                 840                 845
Thr Thr Leu Thr Thr Gly Thr Trp Thr Asn Thr Gly Gly Gln Leu Gln
                850                 855                 860
Ile Thr Gly Pro Ala Thr Leu His Ala Thr Thr Leu Asp Asn Arg Gly
865                 870                 875                 880
Gly Ile Leu His Thr Ala Thr Gly Pro Leu Asp Leu Arg Val Thr Gly
                885                 890                 895
Thr Ile Asn Asn Gln Asp Asn Gly Ile Leu Ser Ser Thr Ala Ala Leu
                900                 905                 910
Thr Leu Thr Ala Ala Ser Leu His Asn Gln His Gly Thr Leu Asp Ala
                915                 920                 925
Ala Gly Pro Ala His Leu Thr Leu Thr Gly Leu Leu Asp Asn Thr Ala
                930                 935                 940
Gly Leu Leu Gln Thr Ala His Thr Leu Trp Leu Thr Ser Ala Gly Leu
945                 950                 955                 960
Thr Asn Arg Ser Gly Thr Leu Thr Ala Ala Leu Thr Leu Asp Thr
                965                 970                 975
```

```
Gln Ala His Thr Leu Asp Asn Thr Ser Gly Arg Leu Gly Thr Thr Thr
            980                 985                 990

Gly Asn Leu Thr Leu His Thr Gly Leu Leu Asp Asn Thr Ala Gly Leu
            995                1000                1005

Leu Gln Thr Ala Ala Thr Leu Thr Ile Asp Thr Gly Ala Ala Pro Leu
           1010                1015                1020

Thr Asn Arg Asp Gly Gly Thr Leu Leu Ala Ala Asp Thr Leu Asp Leu
1025                1030                1035                1040

His Thr Thr Thr Leu Asp Asn Arg Gly Gly Thr Ile Asp Ser Gln Thr
           1045                1050                1055

Ala Thr His Leu His Thr Thr Thr Ile Asp Asn Thr Thr Ala Gly His
           1060                1065                1070

Ile Ser Ser Asn Gly Thr Leu Gln Ile Asp Gly Thr Thr Leu Thr Asn
           1075                1080                1085

Thr Gly Gly Arg Leu His Ser Gly Gly Asp Thr Arg Leu His Leu Gln
           1090                1095                1100

Asp Thr Leu Asn Asn His Asp Gly Arg Ile Thr Ala Ala Gly Thr Leu
1105                1110                1115                1120

Asp Ile Thr Thr Thr Thr Leu Asp Asn His Ser Thr Pro Leu Thr Ala
           1125                1130                1135

Pro Pro Ala Thr Gln Thr Arg Ala Pro Thr Gly Ala Pro Asp Asn Gly
           1140                1145                1150

Leu Tyr Ala Thr His Ile Gln Ile Ala Ser Thr Thr Leu Asp Asn Thr
           1155                1160                1165

Ala Gly Thr Leu Ser Ala Ala Gln Asn Leu Thr Leu Thr Leu Ser Asp
           1170                1175                1180

Thr Leu Thr Asn Thr Ala Gly His Leu Ser Ala Gly Ala Thr Leu Asp
1185                1190                1195                1200

Leu Thr Ala Asp His Leu Ser Asn His Thr Gly Thr Leu Leu Ser Gly
           1205                1210                1215

Ala Ser Gln Thr Leu His Leu His Arg Leu Thr Gly Asp Gly Arg Leu
           1220                1225                1230

His Ala Gly Asn Ala Leu Thr Leu Thr Leu Gln Asp Ser Leu Asp Thr
           1235                1240                1245

Ala Gly Thr Leu Ser Ala Thr Gly Leu Leu Thr Leu Thr Thr Ala Gly
           1250                1255                1260

Asp Leu Thr Asn Arg Gly Leu Ile Gln Ala Ala Asp Leu Thr Ala Gln
1265                1270                1275                1280

Ala Arg Asp Ile Thr Thr Thr Ala Thr Gly Gln Leu Leu Thr Thr Gly
           1285                1290                1295

His Thr His Leu Thr Ala Thr Gly Thr Leu Asn Asn Ser Gly His Leu
           1300                1305                1310

Gln Ala Ala Asp Leu Thr Ala Gln Ala His Asp Ile Thr Thr Thr Ala
           1315                1320                1325

Thr Gly Gln Leu Leu Thr Thr Gly His Thr His Leu Thr Ala Thr Gly
           1330                1335                1340

Thr Leu Asn Asn Ser Gly His Leu Gln Ala Ala Asp Leu Thr Ala Gln
1345                1350                1355                1360

Ala Asn Thr Ile Thr Asn Thr Gly Thr Phe Leu Ala Thr Ser His Ala
           1365                1370                1375

Thr Leu Thr Ala Thr Asp Thr Leu Thr Asn Ser Gly Leu Leu Gln Ala
           1380                1385                1390

Ala Asp Leu Thr Ala Gln Ala Asn Thr Ile Thr Asn Thr Ala Thr Gly
           1395                1400                1405
```

```
Arg Leu Leu Thr Thr Ala His Thr Gln Leu Thr Ala Thr Asp Thr Leu
    1410                1415                1420

Thr Asn Ser Gly Leu Val His Ala Gly Asp Leu Thr Val His Ala Arg
1425                1430                1435                1440

Asp Ile Thr Asn Thr Ala Thr Gly Gln Leu Ile Ala Ser Asn Leu Ala
        1445                1450                1455

Gln Leu Thr Ala Thr Ala Thr Leu Thr Asn Arg Gly Leu Ile Asp Ala
        1460                1465                1470

Phe Thr Thr His Leu Ser Ala Pro Thr Ile Asp Asn Leu Gly Thr Gly
        1475                1480                1485

Arg Leu Tyr Gly Asp His Ile Ala Leu Gln Ala His Thr Leu Thr Asn
        1490                1495                1500

Arg Asp Glu Thr Ser Asp Gly His Thr His Thr Ala Thr Ile Ala Ala
1505                1510                1515                1520

Arg Glu Arg Leu Asp Ile Gly Ala Asp Thr Leu Arg Asn Thr Ala Asn
        1525                1530                1535

Ala Met Ile Leu Ser Asp Gly Asp Ala Ala Ile Gly Ala Thr Leu Asp
        1540                1545                1550

Asn Thr Leu His Ala Thr Gly Ile Ala Thr Leu Ile Asp Asn Arg Ser
        1555                1560                1565

Ala Thr Ile Asp Ile Thr Gly Thr Leu Asn Ile Thr Thr Thr Thr Leu
        1570                1575                1580

Asn Asn Ile Arg Glu Asn Val His Ile Ala His Ala Pro Asp Val Val
1585                1590                1595                1600

Thr Glu Ala Arg Met Tyr Gln Pro His Trp Arg Lys Asn Lys Pro Asn
        1605                1610                1615

Gly Gly Ser Gly Asp Phe Arg Leu Ser Ser Asn Tyr Asp Ala His Asp
        1620                1625                1630

Ile Tyr Tyr Leu Asn Pro Ala Asp Ile Leu Glu Asp Thr Pro Tyr Ile
        1635                1640                1645

Thr Pro Asp Gly Gln Lys Ile His Arg Ala Ile Val Arg Leu Thr Pro
        1650                1655                1660

Gln Thr Ser Ala Tyr Phe Tyr Ala Arg Gly Gly Leu Tyr Ala Ser Gln
1665                1670                1675                1680

Ala Glu Arg Arg Arg Leu Asp Leu Thr Ala Arg Thr Gly Asp Ser Leu
        1685                1690                1695

Val Leu Tyr Tyr Thr Asp Arg Gln Asp Lys Gln Pro Asn Pro Asp His
        1700                1705                1710

Val Ala Ala Ala Ala Thr Asn Asp Ser Ala Phe Ile Gly Leu Asp Thr
        1715                1720                1725

Pro Gln Gln Asn Glu Arg Leu Lys Ile Val Pro Ile Thr Tyr Ala Pro
        1730                1735                1740

Gly Asp Asp Arg Leu Thr Tyr Asp Pro Thr Tyr Gly Thr Cys Thr Asp
1745                1750                1755                1760

Asp Cys Val Arg Leu Val Thr Trp His Asp Tyr Thr Asp Pro Asp His
        1765                1770                1775

Thr Leu Ile Asp Met Arg Arg Gly Pro Asn Asp Val Asp Asp Asn Glu
        1780                1785                1790

Arg Glu Arg His Ala Thr Arg Thr Thr Gln Gln Glu Ile Leu Asn Pro
        1795                1800                1805

Asp Ala Gly Ala Pro Ala Leu Ile Gln Ser Gly Gly Thr Met Arg Ile
        1810                1815                1820

Asp Val Gly Tyr Leu Tyr Asn His Tyr Ala Asp Leu Leu Ala Gly Gly
```

-continued

```
                1825                1830                1835                1840
Asp Gln Thr Ile Val Gly Leu Pro Pro His Pro Thr Lys Glu Thr Ala
                    1845                1850                1855

Asp Asp Glu His Lys Tyr Asn Arg Ala Leu Leu Ile Asp Asn Arg Ala
                1860                1865                1870

Leu Gln Leu Ser Arg Thr Asp Arg Phe Gln Asn Ile Ser Thr Thr Tyr
            1875                1880                1885

Arg Gly Lys Asp Ser Ala Pro Trp Ser Asn Glu Ser Arg Thr Thr Pro
        1890                1895                1900

Thr Thr Gln Ile Gly Gly Arg Ile Thr Ser Gly Gly His Gln His Ile
1905                1910                1915                1920

Ala Ala Gln Thr Phe Asn Asn Val Thr Asp Ser Thr His Ala Pro Glu
                1925                1930                1935

Pro Ile Gln His Val Thr Tyr Asn Pro Ser Thr Gln Thr Leu Thr Ile
            1940                1945                1950

Ala Asp Gly His Ile Thr Val Thr Asp Thr Pro Pro Ser Leu His Thr
        1955                1960                1965

Val Ser Leu Ala Asp Asn Gly Phe Ser His Gly Gln Glu Leu Thr Tyr
    1970                1975                1980

Ile Pro Glu Lys Ser Ile Thr Thr Pro Asn Ala Pro Ile Arg Asp Pro
1985                1990                1995                2000

Ala Ala Pro Pro Ala Val Thr Val Thr Pro Thr Gly Pro Leu Thr Leu
                2005                2010                2015

Pro Asn Asn Ser Leu Phe Thr Ile His Pro Asp Thr Ala Thr Leu Ile
            2020                2025                2030

Thr Thr Asp Pro Arg Phe Thr Leu Gly Arg Pro Tyr Thr Ser Ala Asp
        2035                2040                2045

Ser Gln Leu His Ala Leu Gly Asp His Asp Thr Leu His Lys Arg Leu
    2050                2055                2060

Gly Asp Gly Tyr Tyr Glu Gln Arg Leu Ile Arg Glu Gln Ile Ala Gln
2065                2070                2075                2080

Leu Thr Gly Arg Arg Arg Leu Asp Gly Tyr Thr Asp Asp His Gln
                2085                2090                2095

Tyr Arg Ala Leu Leu Asp Ala Gly Leu Thr Val Ala Lys Gln His Gln
            2100                2105                2110

Leu Arg Pro Gly Ile Ala Leu Ser Ala Asp Gln Met Ala Gln Leu Thr
        2115                2120                2125

Ser Asp Ile Val Trp Leu Val Gln Gln Asp Val His Leu Pro Asp Gly
    2130                2135                2140

Thr Thr Thr Val Ala Leu Val Pro Arg Leu Tyr Leu Arg Pro Arg Thr
2145                2150                2155                2160

Gly Asp Leu Thr Pro Asp Gly Ala Leu Leu Ala Ala Ser Thr Thr
                2165                2170                2175

Ile Asn Ala His Thr Leu Thr Asn Thr Gly Thr Ile Asp Ala Arg Asp
            2180                2185                2190

Leu Ile Asn Ile Asn Thr His Ile Met Asp Gln Gln Gly Gly Arg Leu
        2195                2200                2205

Thr Ala Asp Ala Ile Asn Ile His Thr Thr Gly Asp Phe Thr Asn Leu
    2210                2215                2220

Gly Gly Gln Phe Thr Ala Gly Asp Phe Leu Lys Val His Ala Gln Gly
2225                2230                2235                2240

Asn Phe Leu Ala Ser Ser Thr Leu Arg Asp Ala Thr Thr Gln Gly Thr
            2245                2250                2255
```

-continued

Arg His His Ser Val Thr Glu Leu Asp Gln Gln Ala Gly Phe Thr Val
            2260                2265                2270

Thr Gly Pro Gly Ala Tyr Leu Gly Leu Ser Thr Asp Gln Ala Met Thr
            2275                2280                2285

Gln Gln Ala Val Ala Ile Ser Asn Thr Gly Leu Asp Gly Tyr Thr Ser
            2290                2295                2300

Leu Lys Ala Thr Gly Arg Leu His Leu Gly Thr Leu Asn Thr His Arg
2305                2310                2315                2320

Ser Asp Thr Thr Gln Trp Asp Pro Arg Asn Ser Arg His Thr Arg Ile
            2325                2330                2335

Asp Thr Glu His Gly Thr Ser Ile Arg Ser Ala Gly Asp Ile Gln Leu
            2340                2345                2350

Asn Ser Gly Gln Asp Ile Asn Leu Arg Ala Val Thr Leu His Ser Thr
            2355                2360                2365

Gln Gly Thr Val Ser Ala Leu Ala Thr Gly Asn Val Thr Ile Thr His
            2370                2375                2380

Gly Asp Thr Leu Gln Tyr Thr Ser Gln Asp Asn His Ser Lys Arg Ser
2385                2390                2395                2400

Gly Leu Leu Asn Ser Arg Thr Thr Thr His Ala Asp Gln Gln Gln
            2405                2410                2415

Thr Gln Ala Met Ser Ser Thr Leu Ser Gly Thr Lys Val Leu Val Lys
            2420                2425                2430

Gly Asn Asn Ile Thr Val Thr Gly Ser His Leu Leu Ser Asp Ala Gly
            2435                2440                2445

Thr Tyr Met Gln Ala Lys Gly Asp Leu Thr Leu Gln Ala Ala Thr Asn
            2450                2455                2460

Thr Thr Gln Ser Thr Tyr Ser Glu His Thr Lys Gln Arg Gly Leu Ile
2465                2470                2475                2480

Arg Asn Gly Gly Ala Ser Leu Thr Leu Gly Asn Gln Ser Gln Arg Thr
            2485                2490                2495

Asp Ser Thr Thr Thr Ala Thr Thr Thr Gly Ser Leu Ile Gly Ala
            2500                2505                2510

Thr Asn Gly Asn Val Thr Leu Leu Ala Gly Gly His Tyr Gln Gln Ile
            2515                2520                2525

Gly Ser Asp Val Leu Ser Pro Asn Gly Asp Ile Asp Ile His Ala Lys
            2530                2535                2540

Lys Val Asp Ile Ile Gln Ala His His Thr Ser His Thr Thr Gln His
2545                2550                2555                2560

Thr Ala Thr Arg Gln Ser Gly Leu Thr Val Gly Leu Ser Thr Pro Leu
            2565                2570                2575

Ile Ala Gly Ala Gln Thr Ala Gln Gln Met Gln His Ala Ala Ala Arg
            2580                2585                2590

Ser Gly Asp Pro Arg Leu His Ala Leu Ala Gly Leu Thr Thr Ala Leu
            2595                2600                2605

Gly Ala Lys Asn Thr Ile Asp Ala Val Arg Gln Asp Pro Arg Ala Leu
            2610                2615                2620

Gly Gly Leu Asn Ala Ser Leu Thr Leu Gly Arg Ser Thr His Asp Ser
2625                2630                2635                2640

Thr Thr Thr Thr Thr Thr Thr Thr Ala Ala Gly Ser Asn Val Asn Ala
            2645                2650                2655

Gly Gly Asn Val Arg Ile Ser Ala Thr Gly Asp Gly Glu Ala Ser Thr
            2660                2665                2670

Leu Thr Ile Gln Gly Ser His Val Arg Gly Asp Asn Met Thr Tyr Leu
            2675                2680                2685

-continued

Lys Ala Asp Gly Asp Ile Ala Leu Leu Ala Ala Asn Thr Thr Thr
    2690                2695                2700

Ser Asp Arg Gln Ser Arg Gly Arg Ser Ala Gly Val Gly Val Ala Val
2705                2710                2715                2720

Asn Leu Gly Ser Ser Gly Thr Ser Ala Gly Leu Thr Ala His Ala Ser
            2725                2730                2735

Thr Ser Thr Gly Ser Gly Gln Ser Thr Asp Leu Thr Trp Thr Asn Ser
            2740                2745                2750

His Val Gly Gly Gly Asn Leu Leu Thr Ile Glu Ala Gly Gly Asp Leu
            2755                2760                2765

Leu Met Lys Gly Ala Ile Gly Thr Ala Lys His Val Ile Ala Asp Ile
    2770                2775                2780

Ala Gly Asn Leu Thr Ile Gln Ser Leu Gln Asp Thr His His Tyr Arg
2785                2790                2795                2800

Ser Lys Asp Arg Ser Leu Gly Gly Ser Leu Thr Val Gly Ala Gly Val
            2805                2810                2815

Ser Gly Ser Ala Asn Leu Asn Asn Gln Thr Ile Arg Ser Asp Tyr Ala
            2820                2825                2830

Ser Val Thr Glu Gln Ser Gly Leu Phe Thr Gly Asp Gly Gly Tyr Asp
            2835                2840                2845

Ile Thr Val Gly Gly Gln Thr His Leu Ile Gly Ala Ile Thr Ser
    2850                2855                2860

Asn Ser Thr Ala Ile His Asn Gly Leu Asn Thr Leu Asp Thr Gly Thr
2865                2870                2875                2880

Leu Ile Leu Gln Asp Ile Glu Asn Arg Ala Thr Tyr Thr Ala Thr Gln
            2885                2890                2895

Val Asn Leu Gly Gly Gly Tyr Ser Arg Asn Gly Gly Thr Val Gly Thr
            2900                2905                2910

Asp Gln Gln Gly His Ala Ala Thr Ala Thr Gln Val Pro Gly Thr Thr
            2915                2920                2925

Leu Pro Thr His Asn Gly Leu Ser Ala Ala Pro Pro Gly Ala Met Thr
    2930                2935                2940

Ala Ser Asp Ser Ser His Ser Thr Thr Tyr Ser Gly Ile Ser Gln Gly
2945                2950                2955                2960

Ala Leu Thr Ile Arg Asp Pro Ala Ala Gln His Ala Leu Thr Gly His
            2965                2970                2975

Thr Ala Ala Gln Thr Ile Ala Gly Leu Asn Arg Asp Ile Leu Thr Asp
            2980                2985                2990

Thr Ala Thr Ser Asn Ala Leu Thr Pro Ile Phe Asp Glu Gln Arg Ile
            2995                3000                3005

Asn Ala Ala Phe Asp Ile Val Thr Ala Leu Gln Arg Glu Thr Gly Thr
            3010                3015                3020

Phe Ile Asn Asn Arg Ala Ala Glu Ala Thr Gln Ala Gln Gln Ala Leu
3025                3030                3035                3040

Gln Ala Glu His Ala Lys Pro Ala Asp Gln Arg Asp Pro Ala His Ile
            3045                3050                3055

Ala Ala Leu Gln Gln Arg Ile Gln Asn Thr Thr Thr Trp Glu Leu Gly
            3060                3065                3070

Gly Thr Gly His Thr Ile Val Thr Ala Leu Thr Leu Ala Ala Gly Gln
            3075                3080                3085

Gln Val Thr Gly Pro Ala Thr Gln Met Leu Gln Asn Ala Ala Val Asn
            3090                3095                3100

Tyr Ile Gln Ser Leu Gly Ala Arg Glu Ile Lys Asp Leu Ala Asp Thr

Leu Gly Ser Asp Thr Ala Arg Ser Ala Leu Gln Gly Leu Leu Gly Cys
            3125                3130                3135

Ala Gly Ala Ala Ala Gln Gly Gln Ala Cys Gly Ala Gly Ala Val Gly
        3140                3145                3150

Gly Ala Ala Ala Val Val Ile Asn Ser Leu Leu Asp Arg Ala Asn Gly
        3155                3160                3165

Ala Glu Ala Ala Ser Leu Ser Ala Glu Glu Lys Gln His Arg Thr Asp
        3170                3175                3180

Leu Val Thr Ser Leu Val Ala Gly Ile Thr Thr Ala Ala Gly Gly Asp
3185                3190                3195                3200

Ala Ala Val Ser Ser Ala Ala Ala Arg Leu Glu Thr Glu Asn Asn Ala
        3205                3210                3215

Ala Phe Ile Pro Val Ile Leu Gly Ala Val Trp Leu Ala Asp Lys Gly
        3220                3225                3230

Ile Thr Ala Tyr Gln Ala Trp Gln Asp Ile Lys Ala Ile Arg Ser Gly
        3235                3240                3245

Glu Lys Thr Leu Glu Gln Val Ala Leu Glu Arg Gly Gln Asp Tyr Val
        3250                3255                3260

Thr Ser Ile Val Ile Gly Asn Leu Ala Lys Tyr Gly Leu Lys Ala Ala
3265                3270                3275                3280

Met Ile Gly Gly Arg Trp Ile Ser Gly Thr Ala Lys Glu Ile Ala Asn
        3285                3290                3295

Ala Glu Lys Glu Ala Leu Arg Gln Ile Arg Asn Asn Pro Lys Gly Pro
        3300                3305                3310

Asp Leu Thr Gln Lys Pro Pro Gly Gln Ile Met Ala Leu Gln Arg Gln
        3315                3320                3325

Lys Arg Leu Asp Asp Val Lys Ser Val Ile Gly Arg Arg Ser Gln Lys
        3330                3335                3340

Asp Thr Leu Val Val Gly Gly Ile Glu Val Lys Ala Val Pro Tyr Asp
3345                3350                3355                3360

Arg Asn Val Pro Gly Gly Ser Asn Lys Ser Gly Thr Thr Lys Val Phe
        3365                3370                3375

Asp Ser His Ala Leu Thr Asp Ala Gln Ile Lys Asp Tyr Ala Gln Gln
        3380                3385                3390

Leu Thr Gly Gly Val Pro Leu Lys Gln Thr Ser Arg Pro Gly Val Tyr
        3395                3400                3405

Thr Ala Lys Leu Ser Asp Gly Ser Thr Val Thr Leu Arg Ser Val Ser
        3410                3415                3420

Lys Ser Asn Gln Glu Thr Gln Ala Arg Trp Thr Ile Asp Ile Lys Asp
3425                3430                3435                3440

Asn Pro Ala Leu Ser Glu Ile Thr Asn Lys Thr Val Glu Leu Lys Phe
        3445                3450                3455

Arg

<210> SEQ ID NO 6
<211> LENGTH: 3848
<212> TYPE: PRT
<213> ORGANISM: E. chrysanthemi

<400> SEQUENCE: 6

Met Leu Ser Arg Tyr Trp Ala Phe His Thr Ala Lys Leu Arg Ser Ser
1               5                   10                  15

Gly Met Lys Ala Val Lys Thr Ser Gln Arg Val Met Val Trp Ala Leu
            20                  25                  30

```
Val Trp Leu Thr Gly Leu Gln Pro Val Leu Ala Trp Ala Ala Gly
         35                  40                  45

Val Thr Val Ala Ser Gly Asn Thr Ala Leu Glu Ala Ala Gly Asn Gly
 50                  55                  60

Val Pro Val Val Asn Ile Ala Thr Pro Asp Ala Ser Gly Leu Ser His
 65                  70                  75                  80

Asn Arg Tyr His Asp Phe Asn Val Asp Asn Arg Gly Leu Ile Leu Asn
                 85                  90                  95

Asn Gly Thr Ala Arg Leu Thr Pro Ser Gln Leu Gly Gly Leu Ile Gln
            100                 105                 110

Asn Asn Pro Asn Leu Asn Gly Arg Ala Ala Ala Ile Leu Asn Glu
            115                 120                 125

Val Val Ser Pro Asn Arg Ser Arg Leu Ala Gly Tyr Leu Glu Val Ala
        130                 135                 140

Gly Gln Ala Ala Asn Val Val Ala Asn Pro Tyr Gly Ile Thr Cys
145                 150                 155                 160

Ser Gly Cys Gly Phe Leu Asn Thr Pro Arg Leu Thr Leu Thr Thr Gly
                165                 170                 175

Thr Pro Gln Phe Asp Ala Ala Gly Leu Ser Gly Leu Asp Val Arg
            180                 185                 190

Gly Gly Asp Ile Leu Ile Asp Gly Ala Gly Leu Asp Ala Ser Arg Ser
        195                 200                 205

Asp Tyr Phe Gly Leu Ile Ala Arg Thr Ala Ser Leu Gln Ala Gly Leu
210                 215                 220

Asn Ala Arg Asp Ala Gln Val Val Leu Gly Ala Asn Arg Val Gly Ala
225                 230                 235                 240

Asp Gly Arg Val Thr Ala Gln Ala Gly Ser Gly Pro Ala Pro Val Leu
            245                 250                 255

Ala Leu Asp Thr Gly Ala Leu Gly Gly Met Tyr Ala Asn Arg Ile Arg
            260                 265                 270

Leu Val Ser Thr Glu Gln Gly Val Gly Val Asn Thr Ala Gly Leu Ser
        275                 280                 285

Ala Arg Glu Gly Asp Ile Arg Leu Ser Ala Asn Gly Arg Leu Gln Val
        290                 295                 300

Arg Gly Ala Val Ala Gln Gly Glu Leu Thr Ala Gln Gly Glu Thr Leu
305                 310                 315                 320

Ala Leu Gln Gly Asn Gln Gln Ala Gln Gly Ser Ile Thr Leu Arg Gly
            325                 330                 335

Ala Gln Gly Val Thr Leu Thr Gly Ser Arg Thr Arg Ala Gly Gln Gly
            340                 345                 350

Leu Thr Leu Ala Ser Asp Gly Arg Ile Thr Ala Ala Asp Ala Gly Leu
        355                 360                 365

Ser Ala Gly Val Arg Glu Asp Gly Thr Val Gln Pro Gly Asp Gly Leu
    370                 375                 380

Ser Leu Thr Gly Arg Glu Leu Ala Leu Gly Gln Ser Gln Leu Ala Gly
385                 390                 395                 400

Asp Arg Val Ser Leu Asn Ser Thr Gly Ala Val Ser Gln Ser Arg Ala
            405                 410                 415

Gly Val Ala Gly Gly Ser Val Leu Thr Val Asn Gly Gly Ala Leu Ser
            420                 425                 430

Leu Asp Gly Asp Ala Gly Ala Gln Thr Leu Thr Val Ser Gly Ser Gly
        435                 440                 445

Leu Ser Gly Ser Gly Arg Trp Gln Ala Thr Gly Asp Leu Thr Leu Asp
```

```
              450             455             460
Gly Leu Asp Arg Gly Ala Val Gly Arg Gly Ala Ala Gly Gly Arg Gly
465                 470                 475                 480

Ala Val Gly Ala Gly Gly Glu Pro Gly Gln Pro Gly His Ala Gly Gly
                485                 490                 495

Arg Ala Gly Thr Leu Thr Thr Pro Gly Leu Asp Asn Arg Gly Thr Val
                500                 505                 510

Ser Gly Arg Gln Val Ala Val Arg Thr Ala Gln Leu Gly Asn Ala Gly
                515                 520                 525

Thr Leu Ser Ala Asp Glu Thr Leu Thr Ile Gln Ala Gln Thr Gly Leu
530                 535                 540

Asp Asn Ser Gly Ser Leu Leu Ser Gly Gly Ala Leu Thr Ile Ala Ala
545                 550                 555                 560

Gly Gln Thr Asp Asn Arg Gly Val Leu Ser Gly Ala Val Thr Leu
                565                 570                 575

Ser Gly Asp Ser Leu Trp Asn Gly Gly Thr Leu Gln Gly Arg Gln Ser
                580                 585                 590

Leu Gly Val Asn Ala Leu Ala Gly Phe Ser Gln Thr Ala Asp Gly Ala
                595                 600                 605

Leu Thr Ser Gly Gly Thr Val Thr Val Ser Ser Gly Thr Leu Glu Thr
                610                 615                 620

Ala Gly Ala Leu Ser Ala Gln Gly Leu Gln Leu Arg Thr Gly Leu Trp
625                 630                 635                 640

Arg Asn Gln Gly Ala Val Ser Leu Thr Gly Asp Gly Gln Leu Thr Val
                645                 650                 655

Asp Glu Leu Asp Asn Ser Gly Thr Leu Leu Ser Ser Gly Ala Trp Asp
                660                 665                 670

Ile Ala Gly Gly Arg Leu Gly Asn Ser Gly Thr Leu Gln Gly Asp Arg
                675                 680                 685

Leu Thr Leu Arg Gly Asp Arg Leu Asp Asn Gln Gly Ala Leu Thr Gly
                690                 695                 700

Thr Thr Gln Thr Ala Leu Arg Leu Gly Gly Ala Leu Ala Asn Arg Gly
705                 710                 715                 720

Thr Val Ser Gly Asn Arg Leu Ala Val Thr Ala Ala Leu Asp Asn
                725                 730                 735

Gly Gly Thr Leu Leu Gly Val Glu Ala Leu Thr Leu Thr Thr Asp Gly
                740                 745                 750

Ala Leu Thr Asn Arg Gly Thr Gly Arg Leu Leu Thr Gln Gly Ala Ala
                755                 760                 765

Val Leu Thr Ala Ala Ser Val Val Asn Ala Gly Glu Gly Gln Ala Gly
                770                 775                 780

Arg Leu Gln Leu Thr Gly Gly Thr Leu Ala Asn Thr Gly Thr Leu Ala
785                 790                 795                 800

Val Asn Gly Gly Ala Ser Leu Thr Leu Asp Gly Leu Asp Asn Arg Gly
                805                 810                 815

Thr Leu Ser Ala Gly Gly Asp Leu Thr Val Thr Gly Ala Asp Leu Arg
                820                 825                 830

Asn Ala Gly Gln Met Ala Ala Gln Gly Ala Leu Thr Leu Thr Gly Asn
                835                 840                 845

Tyr Gly Gly Ala Gly Ser Leu Tyr Ser Glu Gly Ala Leu Ser Leu Ser
                850                 855                 860

Gly Ala Ala Leu Val Asn Gly Gly Arg Trp Gln Gly Ala Thr Val
865                 870                 875                 880
```

-continued

Ala Val Arg Gly Gly Pro Leu Thr Asn Ser Gly Val Thr Gly Leu
            885                 890                 895

Thr Ala Leu Thr Val Thr Thr Asp Gly Thr Leu Ser Asn Thr Gly Arg
                900                 905                 910

Leu Glu Gly Arg Arg Leu Asp Leu Thr Ala Glu Ala Leu Asp Asn Gly
            915                 920                 925

Gly Thr Leu Leu Gly Val Asp Ala Leu Thr Leu Ala Ile Thr Gly Thr
        930                 935                 940

Ala Arg Asn Gln Ala Gly Gly Arg Phe Leu Ser Gln Gly Asp Gly Arg
945                 950                 955                 960

Leu Thr Ala Ala Thr Leu Asp Asn Gln Gly Asp Trp Gln Gly Gly Arg
            965                 970                 975

Ile Asp Val Thr Ala Gly Arg Val Arg Asn Ala Gly Gln Val Leu Gly
            980                 985                 990

Ile Ala Ala Leu Thr Leu Thr Ala Asp Asn Ala Leu Thr Asn Thr Gly
            995                 1000                1005

Thr Gly Arg Leu Leu Thr Pro Gly Ala Ala Val Leu Thr Ala Ala Thr
            1010                1015                1020

Ala Val Asn Asp Gly Glu Trp Gln Ala Gly Ser Leu Arg Leu Thr Ala
1025                1030                1035                1040

Asp Arg Leu Arg Asn Gly Gly Arg Ile His Ser Asp Gly Asp Leu Val
            1045                1050                1055

Val Thr Leu Pro Thr Ala Asp Gly Asp Pro Arg Arg Ala Ala Gln
            1060                1065                1070

Arg Leu Ala Gln Glu Val Gln Thr Leu Gly Ala Gly Glu Leu Ser Asn
            1075                1080                1085

Ser Gly Thr Leu Val Ala Asp Gly Asp Gly Arg Leu Thr Ala Arg Gln
            1090                1095                1100

Val Asp Asn Ala Gly Thr Leu Ser Thr Gly Gly Ala Leu Thr Leu Thr
1105                1110                1115                1120

Ala Gly Ala Ile Thr Asn Ala Gly Arg Leu Glu Ser Arg Thr Leu Ser
            1125                1130                1135

Leu Thr Gly Asp Ser Leu Asp Asn Gly Gly Thr Leu Leu Ala Glu Gln
            1140                1145                1150

Gly Gly Gly Leu Thr Leu Ser Asp Arg Leu Thr Val Gly Ala Asp Gly
            1155                1160                1165

Gln Val Leu Ser Asn Gly Asp Trp Gln Ile Gln Ala Gly Ala Val Thr
            1170                1175                1180

Ser Leu Gly Gln Trp Gln Gly Lys Asn Leu Arg Leu Ser Ala Asp Thr
1185                1190                1195                1200

Leu Thr His Asp Gly Val Leu Gln Ala Glu Arg Asp Ile Thr Leu Ala
            1205                1210                1215

Leu Leu Gln Asp Tyr Thr Gly Gly Ala Gly Ser Gln Val Arg Gly Asn
            1220                1225                1230

Gly Ala Val Thr Leu Thr Ala Asp Arg Val Thr Gln Gln Gly Asp Ile
            1235                1240                1245

Gly Gly Glu Arg Leu Gln Leu Thr Thr Gly Thr Leu Thr Asn Gly Gly
            1250                1255                1260

Arg Leu Val Gly Leu Ser Gln Leu Asp Val Thr Ser Arg Gly Gln Leu
1265                1270                1275                1280

Thr Asn Ser Ala Asp Gly Ala Leu Leu Gly Asn Gly Thr Ala Gly Ile
            1285                1290                1295

Thr Ala Ala Ala Leu Ser Asn Ala Gly Val Leu Gln Gly Asp Ala Leu
            1300                1305                1310

```
Thr Val Arg Ala Gly Thr Val Asp Asn Ala Gly Ser Met Gln Gly Thr
            1315                1320                1325

Ala Ala Leu Thr Leu Asp Gly Val Thr Arg Tyr Asp Gly Gly Ala Asp
            1330                1335                1340

Ser Arg Leu Leu Ser Gly Gly Ala Met Thr Leu Ala Leu Asp Thr Ala
1345                1350                1355                1360

Asp Asn Gly Gly Val Trp Gln Ala Gly Glu Leu Arg Val Ser Gly Thr
            1365                1370                1375

Ser Leu Thr Asn Arg Gly Gln Ile Thr Gly Leu Ser Gly Leu Thr Ile
            1380                1385                1390

Asp Ala Thr Gly Leu Ser Asn Ala Gly Arg Leu Ala Thr Gln Gly Arg
            1395                1400                1405

Ala Thr Leu Arg Gly Arg Gln Phe Asp Asn Gly Gly Thr Leu Thr Ala
            1410                1415                1420

Leu Gly Asp Leu Thr Ala Asp Phe Arg Asp Gly Ile Val Asn Gln Ala
1425                1430                1435                1440

Gly Gly Gln Leu Leu Ser Gly Gly Ala Gly Gln Leu Thr Thr Gly Thr
            1445                1450                1455

Leu Thr Asn Ala Gly Trp Val Gln Gly Gln Asp Leu Thr Leu Thr Ala
            1460                1465                1470

Asp Thr Leu Phe Asn Gln Gly Ser Leu Leu Gly Leu Asp Asp Gly Ala
            1475                1480                1485

Ile Gln Leu Thr Gly Ala Tyr Val Gly Gly Val Asn Ser Arg Val Gly
            1490                1495                1500

Gly Asn Gly Ala Phe Ser Leu Ser Ala Ala Thr Ile Asp Gln Ala Gly
1505                1510                1515                1520

Gln Trp Gln Ala Arg Asp Val Thr Leu Arg Ala Thr Arg Leu Arg Asn
            1525                1530                1535

Gln Gly Thr Leu Thr Ala Gly Gly Gln Leu Thr Ala Thr Leu Asp Asp
            1540                1545                1550

Ala Leu Glu Asn Thr Ala Gly Ala Val Leu Ser Gly Gly Thr Val Ser
            1555                1560                1565

Leu Gly Ala Ala Thr Val Ser Asn Ala Gly Gln Leu Glu Gly Arg His
            1570                1575                1580

Gly Leu Thr Val Ala Gly Gly Ser Arg Leu Asp Asn Gln Arg Gly Gly
1585                1590                1595                1600

Gln Leu Leu Ser Gly Gly Gln Leu Ala Leu Ser Ala Pro Gln Leu Thr
            1605                1610                1615

Asn Ala Gly Trp Val Gln Gly Gln Asp Leu Thr Leu Thr Thr Ala Gln
            1620                1625                1630

Leu Asp Asn Gly Gly Thr Leu Gln Ala Gln Ser Gly Leu Thr Leu His
            1635                1640                1645

Leu Pro Gln Trp Thr Asn Arg Gly Thr Val Gln Ala Gly Gln Leu Asp
            1650                1655                1660

Ile Thr Thr Asp Gly Ala Leu Glu Asn Arg Gly Thr Leu Leu Gly Leu
1665                1670                1675                1680

Thr Arg Leu Ala Leu Gln Ala Ala Arg Leu Asp Asn Ala Asp Gly Ala
            1685                1690                1695

Arg Leu Tyr Ser Ala Gly Asn Leu Gln Leu Arg Thr Gly Gln Leu Val
            1700                1705                1710

Gln Asn Gly Gln Leu Ala Ala Leu Gly Asp Leu Arg Ala Asp Ile Gly
            1715                1720                1725

Asn Ala Phe Thr Phe Thr Arg Thr Leu Ala Ala Gly Gly Gln Leu Thr
```

```
                  1730               1735               1740
Leu Asn Val Thr Gly Asp Leu Val Gln Ala Gly Thr Leu Gln Gly Asn
1745                1750                1755                1760
Gly Val Thr Val Thr Ser Thr Gly Thr Leu Thr Gln Gln Gly Arg Ile
                1765                1770                1775
Val Ala Gly Thr Gly Asp Ser Thr Leu Ser Ala Ala Ala Ile Asn Gln
            1780                1785                1790
Thr Ala Ser Gly Ser Ile Gln Ala Gly Ala Leu Arg Leu Arg Ala
        1795                1800                1805
Glu Gly Asn Ile Val Asn Arg Gly Phe Val Gly Thr Ala Ala Asp Leu
    1810                1815                1820
Leu Leu Gln Ala Gly Gly Val Ile Asp Asn Gly Gly Leu Leu Tyr Gly
1825                1830                1835                1840
Gly Gly Asn Leu Trp Leu Leu Ser Asp Ala Leu Val Asn Arg Phe Gly
                1845                1850                1855
Asn Ile Leu Ala Gly Asn Ser Leu Trp Ile Gln Arg Asp Ala Ala Gly
            1860                1865                1870
Asn Ala Ser Gly Ser Val Leu Asn Ser Ser Gly Thr Ile Glu Thr Gln
        1875                1880                1885
Arg Gly Asp Ile Thr Val Arg Thr Gly Thr Leu Thr Asn Gln Arg Glu
    1890                1895                1900
Gly Leu Val Val Thr Glu Gly Glu Ser Lys Thr Glu Val Val Pro Asp
1905                1910                1915                1920
Trp Val Gly Gly Glu Arg Val Glu Val Pro Leu Thr Trp Phe Lys Glu
                1925                1930                1935
Gly Glu Leu Gly Ile Ala Glu Phe Tyr Thr Gly Cys Leu Arg Gly Gly
            1940                1945                1950
Lys Ala Ser Gly Ala Asn Cys Glu Tyr Ser Ala Gly Tyr Leu Leu Ala
        1955                1960                1965
Pro Phe Ser Ser Ala Ala Ile Gln Lys Val Ala Leu Glu Ser Lys Ser
    1970                1975                1980
Val Ser Val Ser Ala Gln Gly Gly Glu Ala Arg Ile Asn Ser Ala His
1985                1990                1995                2000
Asp Thr Leu Ile Thr Ser Ser Ile Leu Thr Asn Glu Ala Ser Ala Ile
                2005                2010                2015
Tyr Ala Arg Asn Asn Ile Val Leu Ser Gly Asn Ser Leu Asn Asn Thr
            2020                2025                2030
Ser Tyr Gln Ala Gly Asp Leu Lys Arg Tyr Leu Thr Tyr Arg Tyr Asp
        2035                2040                2045
Ser Val Glu Phe Val Tyr Gly Thr Trp Ser Trp Ile Asn Asp Phe Ala
    2050                2055                2060
Asn Asp Asp Gln Ser Ala Tyr Val Gly Gly Ser Ser Pro Ile Thr
2065                2070                2075                2080
Lys Gln Leu Asp Leu Ala Asp Lys Phe Glu Ile Gln Asn Lys His Tyr
                2085                2090                2095
Ser Ile Asn Tyr Lys Pro Val Gly Glu Pro Thr Ser Glu Leu Ile Asn
            2100                2105                2110
Gly Gln Thr Tyr Ala Ala Thr Ile Gln Ala Gly Gly Ala Ile Thr Ala
        2115                2120                2125
Ser Phe Thr Gln Asn Ile Ser Asn Thr Ser Leu Gln Pro Gly Ser Gly
    2130                2135                2140
Gly Val Met Pro Ala Leu Ala Thr Pro Thr Leu Ala Gly Val Ser Ala
2145                2150                2155                2160
```

-continued

```
Phe Thr Pro Val Gly Ala Gln Ala Gly Arg Glu Leu Ser Gly Gly Thr
            2165                2170                2175
Ala Ala Ala Val Ser Gly Ser Pro Leu Ser Gly Thr Gly Asn Gly Val
        2180                2185                2190
Ala Leu Ala Gly Gln Ala Glu Arg Pro Gly Thr Ala Ala Gly Ala Val
        2195                2200                2205
Thr Arg Ala Gly Thr Asp Ala Gly Gly Gly Leu Thr Pro Ala Gly
        2210                2215                2220
Ile Asp Ser Gly Leu Gly Thr Ala Ala Pro Val Ala Pro Gly Ala Leu
2225                2230                2235                2240
Ser Pro Gly Asp Leu Gln Ala Ala Leu Arg Gln Gly Leu Ala Gln Val
            2245                2250                2255
Ala Gly Pro Ser Leu Thr Asp Tyr Pro Leu Pro Thr Ser Gln Asn Gly
            2260                2265                2270
Leu Phe Val Ala Asp Thr Ala Gly Asp Ser Arg Tyr Leu Ile Arg Ser
            2275                2280                2285
Asn Pro Thr Leu Ser Gln Leu Gly Gln Val Asp Asn Ser Leu Phe Gly
            2290                2295                2300
Asp Leu Arg Gly Leu Leu Gly Gln Thr Pro Gly Thr Ser Val Pro Val
2305                2310                2315                2320
Glu Thr Thr Pro Thr Leu Thr Asp Pro Thr Gln Phe Leu Gly Ser Ser
            2325                2330                2335
Tyr Leu Leu Gly Lys Leu Asn Leu Asp Ala Glu His Asp Tyr Arg Phe
            2340                2345                2350
Leu Gly Asp Ala Ala Phe Asp Thr Arg Tyr Ile Ser Asn Ala Val Leu
            2355                2360                2365
Ser Gln Thr Gly Gln Arg Tyr Leu Asn Gly Val Gly Ser Glu Leu Ala
            2370                2375                2380
Gln Met Gln Gln Leu Met Asp Asn Ala Ala Ala Glu Lys Ser Arg Leu
2385                2390                2395                2400
Asn Leu Gln Leu Gly Val Ser Leu Ser Pro Ala Gln Val Ala Gly Leu
            2405                2410                2415
Ser His Ser Ile Val Trp Trp Glu Asn Ile Thr Val Gly Gly Gln Thr
            2420                2425                2430
Val Leu Ala Pro Lys Leu Tyr Leu Ala Gln Ala Asp Asn Thr His Leu
            2435                2440                2445
Gln Gly Ser Arg Leu Val Ala Asp Arg Val Ser Leu Ser Ala Gly Gly
            2450                2455                2460
Asp Ile Asp Asn Arg Gly Ser Thr Val Thr Ala Gln Glu Val Leu Asn
2465                2470                2475                2480
Ile Ala Ser Gly Gly Asn Leu Ser Asn Ser Glu Gly Gly Leu Leu Ser
            2485                2490                2495
Ala Gly Gly Ala Leu Asn Leu Val Ala Leu Gly Asn Leu Thr Asn Arg
            2500                2505                2510
Ser Ala Thr Leu Gln Gly Asn Thr Val Thr Leu Ala Ser Val Asn Gly
            2515                2520                2525
Asp Ile Val Asn Ser Thr Thr Thr Asp Gln Trp Gln Phe Glu Ser Ile
            2530                2535                2540
Asn Gly Arg Glu Arg Leu Thr His Thr Asp Ile Gly Gln Thr Gly Leu
2545                2550                2555                2560
Ile Thr Ala Gln Asn Gly Leu Thr Leu Gln Ala Gly His Asp Ile Val
            2565                2570                2575
Leu Asn Gly Ala Gln Leu Ser Ala Gly Gly Pro Leu Ala Leu Ala Ala
            2580                2585                2590
```

```
Gly Asn Asp Ile Gln Leu Asn Ala Leu Thr Thr Leu Thr Asp Thr Val
        2595                2600                2605

Arg Glu Gly Gly Gly Ala Thr Thr Glu Arg Arg Ser Gln Gly Leu Val
    2610                2615                2620

Arg Ser Thr Val Ala Gly Gly Asp Leu Ser Leu Ser Ala Gly Arg
2625                2630                2635                2640

Asp Leu Ser Gly Thr Ala Ala Gln Leu Ser Ala Ala Gly Thr Leu Ala
        2645                2650                2655

Leu Ser Ala Gly Arg Asp Leu Ser Leu Leu Ser Ala Arg Glu Glu Gln
        2660                2665                2670

Phe Gly Ser Asn Ala Trp Ser Arg His Leu Asp Trp Gln Gln Thr Val
        2675                2680                2685

Thr Gln Gln Gly Thr Gly Leu Asn Ala Gly Glu Gly Leu Ser Leu Arg
        2690                2695                2700

Ala Gly Gln Asp Leu Thr Leu Gln Gly Ala Gln Ala Glu Thr Arg Gly
2705                2710                2715                2720

Ala Leu Thr Ala Gln Ala Gly Arg Asp Leu Ser Leu Ser Ala Thr
        2725                2730                2735

Glu Ser Arg His Asp Phe Phe Glu Glu Thr Thr Val Lys Lys Lys Thr
        2740                2745                2750

Phe Ser Thr Thr Val Thr His Thr Val Arg Glu Thr Ala Gln Thr Thr
        2755                2760                2765

Glu Lys Gly Thr Leu Leu Ser Ala Gly Ser Val Ala Leu Thr Ala Gly
        2770                2775                2780

Gln Asp Ile Gly Val Gln Gly Ser Ser Val Ala Ala Asp Gly Gly Val
2785                2790                2795                2800

Ala Leu Thr Ala Gly Arg Asp Ile Thr Thr Ala Ala Ser Val Glu Asn
        2805                2810                2815

Tyr Arg Ser Tyr Glu Glu Gln Ser Arg Lys Lys Ser Gly Leu Phe Ser
        2820                2825                2830

Gly Gly Gly Ile Gly Phe Thr Val Gly Ser Thr Ser Leu Arg Gln Thr
        2835                2840                2845

Leu Glu Ser Ala Gly Thr Thr Gln Ser Gln Ser Val Ser Thr Leu Gly
        2850                2855                2860

Ser Thr Gly Gly Ser Val Ser Leu Arg Ala Gly Gln Asp Val Ser Leu
2865                2870                2875                2880

Thr Gly Thr Asp Val Ile Ala Ala Arg Asp Ile Asp Leu Ser Gly Arg
        2885                2890                2895

Asn Val Thr Val Thr Pro Gly His Asp Val Arg Arg Thr Thr Gln Thr
        2900                2905                2910

Leu Glu Gln Lys Gln Ser Gly Leu Thr Ile Ala Leu Ser Gly Ser Val
        2915                2920                2925

Gly Gly Ala Leu Asn Ser Met Val Glu Thr Val Gln Ala Val Ser Arg
        2930                2935                2940

Glu Ser Asp Ser Arg Leu Lys Ser Leu Ala Gly Val Lys Ala Ala Leu
2945                2950                2955                2960

Ser Ala Gly Gln Gly Ala Gln Ala Thr Arg Leu Ala Met Ala Gln Arg
        2965                2970                2975

Glu Ala Ala Gly Ala Lys Thr Ala Ala Gly Ser Gly Glu Glu Gly Glu
        2980                2985                2990

Gln Pro Gln Ala Val Gly Val Ser Ile Ser Tyr Gly Ser Gln Ser Ser
        2995                3000                3005

Arg Ser Glu Gln Arg Gln Thr Gln Glu Thr Val Ser Gly Ser Ser Val
```

```
                3010            3015            3020
Thr Ala Gly Asp Asn Leu Arg Ile Arg Ala Asp Gly Asp Ile Thr
3025            3030            3035            3040

Val Val Gly Ser Gln Leu Lys Ala Gly Gln Asp Leu Thr Leu Ala Ala
        3045            3050            3055

Thr Gln Asp Ile Arg Leu Leu Ser Gly Ala Asn Thr Gln His Thr Glu
        3060            3065            3070

Gly Ser Asn Gln Ser Arg Gly Gly Ser Ile Gly Val Ser Ile Gly Val
        3075            3080            3085

Ser Ala Ser Gly Ser Phe Gly Leu Ser Val Ser Ala Ser Val Asn Ala
        3090            3095            3100

Ala Lys Gly Asn Leu Arg Gly Asp Gly Leu Thr His Thr Glu Ser Leu
3105            3110            3115            3120

Leu Glu Ala Gly Arg Thr Ala Val Leu Gly Ser Gly Arg Asp Thr Thr
                3125            3130            3135

Leu Gln Gly Ala Gln Val Ser Ala Glu Thr Ile Thr Ala Arg Val Gly
        3140            3145            3150

Arg Asp Leu Leu Val Arg Ser Glu Gln Asp Ser Asp Arg Tyr Asp Ser
        3155            3160            3165

Lys Gln Gln Ser Val Ser Ala Gly Val Thr Ile Pro Ile Tyr Gly Gly
        3170            3175            3180

Gly Gly Gly Ala Ser Phe Ser Phe Ser Arg Asp Lys Val His Ser Asn
3185            3190            3195            3200

Phe Asp Ser Val Gln Glu Gln Ser Gly Leu Phe Ala Gly Thr Gly Gly
        3205            3210            3215

Tyr Asp Ile His Val Gly Ser His Thr Gln Leu Asp Gly Gly Ala Ile
        3220            3225            3230

Ala Ser Thr Ala Gly Ala Asp Arg Ser Arg Leu Glu Thr Gly Thr Leu
        3235            3240            3245

Gly Phe Ser Asn Ile Asp Asn Arg Ala Glu Tyr Ser Ala Ser His His Thr
        3250            3255            3260

Gly Gly Gly Phe Ser Thr Ser Ala Pro Val Gly Leu Gln Val Leu Ser
3265            3270            3275            3280

Asn Val Gly Gly Leu Met Leu Ala Gly Ala Asn Gln Ser Gly Ala Ser
        3285            3290            3295

Ser Gly Thr Thr Tyr Ala Ala Val Ser Asp Gly Thr Leu Ile Ile Arg
        3300            3305            3310

Asp Arg Ala Gly Gln Gln Gln Val Arg Gly Gly Ala Glu Pro Gly Tyr
        3315            3320            3325

Gly Gly Gly Gln Gln Arg Gly Ala Glu Pro Asp Ile Arg Gln Gly Glu
        3330            3335            3340

Gly Gly Glu Pro Ala Ala Ala Gly Thr Thr Ala Val Gly His Arg Asp
3345            3350            3355            3360

Ala Gly Ala Gly Tyr Arg Leu Tyr Gly Arg Gly Asp Ser Gly Asp Glu
        3365            3370            3375

Gly Gly Glu Cys Ala Ala Gly Gly Asp Ala Gly Ser Ala Ala Gly
        3380            3385            3390

Glu Gly Gly Arg Ala Gly Glu Gly Leu Ala Gly Gln Gly Gly Asn Ala
        3395            3400            3405

Gly Gly Gly Asp Ala Gly Ala Val Pro Gly Val Leu Gln Cys Val Ala
        3410            3415            3420

Glu Arg Leu Gly Val Ser Asp Gly Gly Thr Gly Thr Ser Gly Tyr Pro
3425            3430            3435            3440
```

-continued

Gly Gly Gly Gly Gly Ala Ala Gly Cys Ala Gly Glu Cys Gly Ala
            3445                3450                3455

Gly Gly Asp Gly Gly Gly Ala Val Cys Gly Gly Gly Asn Pro Pro
            3460                3465                3470

Ser Asp Asp Gly Cys Gly Gly Gln His Glu Arg Asp Gly Glu His Ala
            3475                3480                3485

Gly Ala Arg Val Ala Gly Cys Gly Gly Gly Ala Gly Gly Arg Glu Thr
            3490                3495                3500

Met Arg Trp Arg Cys Gly Gly Glu Ala Gly Gly Glu Leu Ala Ala Arg
3505                3510                3515                3520

Ala Leu Met Glu Gly Leu Tyr Pro Gly Lys Lys Ala Asp Glu Leu Asn
            3525                3530                3535

Glu Asp Gln Arg Gln Leu Leu Ser Thr Leu Ser Thr Ile Ala Gly Gly
            3540                3545                3550

Leu Ala Ala Gly Val Val Gly Asn Ser Ser Thr Asp Ala Val Gln Gly
            3555                3560                3565

Ala Gln Ser Ala Gln Val Ala Val Glu Asn Asn Leu Leu Ser Ala Lys
            3570                3575                3580

Arg Ser Gln Asp Arg Tyr Glu Lys Leu Ala Ala Cys Asn Gly Asp Lys
3585                3590                3595                3600

Ala Cys Val Ala Glu Val Arg Arg Glu Phe Gly Pro Glu Ser Asp Glu
            3605                3610                3615

Gln Arg Gln Arg Val Glu Asn Cys Ser Ser Ala Ala Asp Cys Tyr Val
            3620                3625                3630

Val Glu Gln Gly Leu Lys Ser Met Arg Ala Glu Tyr Ser Gln Gln Glu
            3635                3640                3645

Ala Ala Leu Ala Glu Lys Ala Arg Thr Gln Gly Val Ser Ser Leu Ser
3650                3655                3660

Glu Ala Glu Gln Lys Glu Trp Ile Ala Ala Arg Ser Ala Leu Thr Glu
3665                3670                3675                3680

Leu Asp Ser Gln Ile Asn Leu Ser Leu His Arg Ala Gln Thr Met Gly
            3685                3690                3695

Gly Ser Thr Glu Val Ser Ala Glu Val Thr Asn Val Met Gly His Ala
            3700                3705                3710

Ala Ile Ala Ser Ala Ala Gly Val Ala Gly Gly Ile Ser Lys Ala Gly
            3715                3720                3725

Ala Asn Gly Ser Lys Asn Gln Gly Gly Asn Thr Asp Lys Leu Pro Asn
            3730                3735                3740

Gly Gln Gln Val Asn His Phe Glu Glu Ser Leu Tyr Asn Leu Pro Pro
3745                3750                3755                3760

Gly Glu Arg Val Ala Leu Val Lys Gln Met Val Asp Gln Val Ala Pro
            3765                3770                3775

Ser Asn Gly Met Val Lys Asp Asn Lys Leu Thr Arg Ile Asn Asn Arg
            3780                3785                3790

Asp Val Tyr Arg Gly Asn Asp Gly Tyr Leu Tyr Ala Val Asp Thr Gln
            3795                3800                3805

His Gly Arg Phe Glu Gln Val Asn Ala Lys Thr Gly Lys His Gln Gly
            3810                3815                3820

Glu Val Asp Met Gly Met Met Pro Ile Ser Asn Ser Met Asp Lys Ser
3825                3830                3835                3840

Gly Gly His Asp Leu Lys Val Lys
            3845

<210> SEQ ID NO 7

<211> LENGTH: 3282
<212> TYPE: PRT
<213> ORGANISM: Xylella fastidiosa

<400> SEQUENCE: 7

```
Met Glu Val Ala Gly Ala Arg Ala Gln Leu Ile Ile Ala Asn Pro Ser
 1               5                  10                  15

Gly Ile Thr Cys Asn Gly Cys Gly Val Ile Asn Ala His Gln Leu Thr
            20                  25                  30

Leu Thr Thr Gly Thr Pro Ile Phe Asn Ala Arg Gly Ala Leu Asp His
        35                  40                  45

Tyr Arg Val Gln Gly Gly Ala Ile Gln Ile Asp Gly Leu Gly Leu Asp
 50                  55                  60

Ser His Ser Thr Asp Tyr Thr Ala Leu Ile Ala Arg Thr Val Gln Leu
 65                  70                  75                  80

Asn Ala Gly Leu Trp Ala His Thr Leu Gln Thr Thr Gly Pro Ala
                85                  90                  95

Thr Val Ala Leu Asp Gly His Pro Thr Ala Ser Leu Pro Ala Pro Pro
                100                 105                 110

Gly Asp Arg Pro Thr Val Ala Leu Asp Val Ser Ala Leu Gly Gly Met
            115                 120                 125

Tyr Ala Gly Lys Ile Thr Leu Ile Gly Thr Glu His Gly Leu Gly Val
130                 135                 140

Arg Asn Ala Gly Gln Leu Ser Ala Thr Ser Ala Pro Leu Thr Val Thr
145                 150                 155                 160

Val Asp Gly Leu Leu Glu Asn Thr Gly Arg Leu Gln Ser Ala Thr Asp
                165                 170                 175

Thr Gln Leu Asn Ala Thr Ala Glu Val Asn Asn Ser Gly Leu Ile Ser
            180                 185                 190

Ala Ala Gln Thr Leu Thr Leu His Thr Pro Thr Thr Ile Asp Asn Arg
        195                 200                 205

Ser Gly Thr Leu Asn Ala Ala Arg Leu Asp Ile Thr Gly Ala Arg Leu
    210                 215                 220

Asp Asn Arg Gly Gly His Ile Gln Gln Thr Gly Leu Gln Pro Leu Thr
225                 230                 235                 240

Leu Gln Thr Gln His Leu Asp Asn Gln Asp Gln Gly Arg Leu Gly Val
                245                 250                 255

Leu Asp Thr Pro Ala Pro Ala Ser Pro Ala Thr Pro Val Thr Ala
            260                 265                 270

Pro Ile Ser Asn Ala Pro Pro Thr Val Ala Pro Pro Ala Thr Asp
        275                 280                 285

Pro Thr Thr Ser Pro Val Ala Pro Thr Val Pro His Leu Ala His Gly
    290                 295                 300

Thr Leu Thr Leu Thr Gln Thr Ile Asp Asn Arg Gly Gly His Ile Thr
305                 310                 315                 320

Ala Gly Gly Ala Ile Asp Ala Ile Leu Thr Asp Leu Asp Asn Arg Asp
                325                 330                 335

Gly Thr Ala Ala Leu Asn Arg Leu Thr Leu Gln Gly Gln Arg Leu Asp
            340                 345                 350

Asn Gln His Gly Ile Leu Thr Leu Ala Thr Asp Ala Thr Ile His Thr
        355                 360                 365

His Thr Leu Asn Asn Ala Ala Gly Gln Leu His Ala Asn Gly Thr Leu
    370                 375                 380

Asp Leu Thr Ala Asp Thr Phe Ser Asn Gln Asn Gly Gln Leu Leu His
385                 390                 395                 400
```

```
Thr Gly Ser Gln Asn Ala Thr Leu Thr Ile Thr Asp Leu Leu Asp Asn
                405                 410                 415
Gln His Gly Ile Ile Ala Ser Ala Ala Asn Leu Leu Thr Leu Lys Thr
                420                 425                 430
Asp His Leu Asn Asn Ala Ala Gly Gln Leu His Ala Asn Gly Ala Leu
                435                 440                 445
Asp Leu Thr Ala Gln Arg Phe Ser Asn Gln Asn Gly Gln Leu Leu His
                450                 455                 460
Thr Gly Ser Gln Asn Ala Thr Leu Thr Ile Ala Asn Leu Leu Asp Asn
465                 470                 475                 480
Gln His Gly Leu Val Ala Ser Ala Ala Asn Ala Leu Thr Leu His Thr
                485                 490                 495
Gly His Leu Asn Asn Asp Ala Gly Gln Phe Gln Thr Asn Gly Ala Leu
                500                 505                 510
Asp Leu Thr Ala Gln Arg Phe Ser Asn Gln His Gly Gln Phe Leu His
                515                 520                 525
Asn Ser Pro Gln Ser Ala His Leu Arg Ile Asp Gly Gln Leu Asp Asn
                530                 535                 540
Gln Gln Gly Val Leu Ala Ser Asn Ala Ala Glu Leu Thr Leu Glu Thr
545                 550                 555                 560
Gly Gln Phe Asn Asn Asp Ser Gly Thr Leu Gln Gln Ser Gly Gln Gly
                565                 570                 575
Thr Leu His Ile Asp Ala Ala Thr Leu Thr Gly His Gly Gly Thr Leu
                580                 585                 590
Thr Ser Gln Gly Ala Leu Thr Leu Thr Gly Thr His Thr Asp Leu Ser
                595                 600                 605
His Ala Thr Thr Thr Ala Gln His Ile Thr Ile His Thr Asp Asp Leu
                610                 615                 620
Thr Thr Ala Gly Gly His Leu Thr Ala Tyr Gly Glu His Thr Leu Gln
625                 630                 635                 640
Leu Asn Ala Arg Thr Arg Ile Asp Asn Thr Ala Gly Thr Ile Ala Thr
                645                 650                 655
Asn Gly Ser Leu Asp Leu His Thr Ala Ala Leu Asp Asn Thr Gly Gly
                660                 665                 670
Thr Leu His Ser Thr Ala Thr Gly Pro Asn Arg Leu Asp Ile Thr His
                675                 680                 685
Thr Leu Thr Asn Thr Ala Gly His Leu Leu Asn Gly Pro Thr Thr
                690                 695                 700
Leu Thr Thr Gly Thr Trp Asn Thr Gly Gly Gln Leu Gln Ile Thr
705                 710                 715                 720
Gly Pro Ala Thr Leu His Ala Thr Thr Leu Asp Asn Arg Gly Gly Ile
                725                 730                 735
Leu His Thr Ala Thr Gly Pro Leu Asp Leu Arg Val Thr Gly Thr Ile
                740                 745                 750
Asn Asn Gln Asp Asn Gly Ile Leu Ser Ser Thr Ala Ala Leu Thr Leu
                755                 760                 765
Thr Ala Ala Ser Leu His Asn Gln His Gly Thr Leu Asp Ala Ala Gly
                770                 775                 780
Pro Ala His Leu Thr Leu Thr Gly Leu Leu Asp Asn Thr Ala Gly Leu
785                 790                 795                 800
Leu Gln Thr Ala His Thr Leu Trp Leu Thr Ser Ala Gly Leu Thr Asn
                805                 810                 815
Arg Ser Gly Thr Leu Thr Ala Ala Ala Leu Thr Leu Asp Thr Gln Ala
```

```
                    820                 825                 830
His Thr Leu Asp Asn Thr Ser Gly Arg Leu Gly Thr Thr Gly Asn
            835                 840                 845
Leu Thr Leu His Thr Gly Leu Leu Asp Asn Thr Ala Gly Leu Leu Gln
            850                 855                 860
Thr Ala Ala Thr Leu Thr Ile Asp Thr Gly Ala Ala Pro Leu Thr Asn
865                 870                 875                 880
Arg Asp Gly Gly Thr Leu Leu Ala Ala Asp Thr Leu Asp Leu His Thr
                        885                 890                 895
Thr Thr Leu Asp Asn Arg Gly Gly Thr Ile Asp Ser Gln Thr Ala Thr
                900                 905                 910
His Leu His Thr Thr Thr Ile Asp Asn Thr Ala Gly His Ile Ser
            915                 920                 925
Ser Asn Gly Thr Leu Gln Ile Asp Gly Thr Thr Leu Thr Asn Thr Gly
            930                 935                 940
Gly Arg Leu His Ser Gly Gly Asp Thr Arg Leu His Leu Gln Asp Thr
945                 950                 955                 960
Leu Asn Asn His Asp Gly Arg Ile Thr Ala Ala Gly Thr Leu Asp Ile
                965                 970                 975
Thr Thr Thr Thr Leu Asp Asn His Ser Thr Pro Leu Thr Ala Pro Pro
                980                 985                 990
Ala Thr Gln Thr Arg Ala Pro Thr Gly Ala Pro Asp Asn Gly Leu Tyr
            995                 1000                1005
Ala Thr His Ile Gln Ile Ala Ser Thr Thr Leu Asp Asn Thr Ala Gly
            1010                1015                1020
Thr Leu Ser Ala Ala Gln Asn Leu Thr Leu Thr Leu Ser Asp Thr Leu
1025                1030                1035                1040
Thr Asn Thr Ala Gly His Leu Ser Ala Gly Ala Thr Leu Asp Leu Thr
                1045                1050                1055
Ala Asp His Leu Ser Asn His Thr Gly Thr Leu Leu Ser Gly Ala Ser
                1060                1065                1070
Gln Thr Leu His Leu His Arg Leu Thr Gly Asp Gly Arg Leu His Ala
            1075                1080                1085
Gly Asn Ala Leu Thr Leu Thr Leu Gln Asp Ser Leu Asp Thr Ala Gly
            1090                1095                1100
Thr Leu Ser Ala Thr Gly Leu Leu Thr Leu Thr Thr Ala Gly Asp Leu
1105                1110                1115                1120
Thr Asn Arg Gly Leu Ile Gln Ala Ala Asp Leu Thr Ala Gln Ala Arg
                1125                1130                1135
Asp Ile Thr Thr Thr Ala Thr Gly Gln Leu Leu Thr Thr Gly His Thr
                1140                1145                1150
His Leu Thr Ala Thr Gly Thr Leu Asn Asn Ser Gly His Leu Gln Ala
            1155                1160                1165
Ala Asp Leu Thr Ala Gln Ala His Asp Ile Thr Thr Ala Thr Gly
            1170                1175                1180
Gln Leu Leu Thr Thr Gly His Thr His Leu Thr Ala Thr Gly Thr Leu
1185                1190                1195                1200
Asn Asn Ser Gly His Leu Gln Ala Ala Asp Leu Thr Ala Gln Ala Asn
            1205                1210                1215
Thr Ile Thr Asn Thr Gly Thr Phe Leu Ala Thr Ser His Ala Thr Leu
            1220                1225                1230
Thr Ala Thr Asp Thr Leu Thr Asn Ser Gly Leu Leu Gln Ala Ala Asp
1235                1240                1245
```

```
Leu Thr Ala Gln Ala Asn Thr Ile Thr Asn Thr Ala Thr Gly Arg Leu
        1250                1255                1260

Leu Thr Thr Ala His Thr Gln Leu Thr Ala Asp Thr Leu Thr Asn
1265                1270                1275                1280

Ser Gly Leu Val His Ala Gly Asp Leu Thr Val His Ala Arg Asp Ile
                1285                1290                1295

Thr Asn Thr Ala Thr Gly Gln Leu Ile Ala Ser Asn Leu Ala Gln Leu
            1300                1305                1310

Thr Ala Thr Ala Thr Leu Thr Asn Arg Gly Leu Ile Asp Ala Phe Thr
        1315                1320                1325

Thr His Leu Ser Ala Pro Thr Ile Asp Asn Leu Gly Thr Gly Arg Leu
        1330                1335                1340

Tyr Gly Asp His Ile Ala Leu Gln Ala His Thr Leu Thr Asn Arg Asp
1345                1350                1355                1360

Glu Thr Ser Asp Gly His Thr His Thr Ala Thr Ile Ala Ala Arg Glu
                1365                1370                1375

Arg Leu Asp Ile Gly Ala Asp Thr Leu Arg Asn Thr Ala Asn Ala Met
            1380                1385                1390

Ile Leu Ser Asp Gly Asp Ala Ala Ile Gly Ala Thr Leu Asp Asn Thr
        1395                1400                1405

Leu His Ala Thr Gly Ile Ala Thr Leu Ile Asp Asn Arg Ser Ala Thr
        1410                1415                1420

Ile Asp Ile Thr Gly Thr Leu Asn Ile Thr Thr Thr Leu Asn Asn
1425                1430                1435                1440

Ile Arg Glu Asn Val His Ile Ala His Ala Pro Asp Val Val Thr Glu
            1445                1450                1455

Thr Pro Met Tyr Gln Pro His Trp Arg Lys Asn Lys Pro Asn Gly Gly
        1460                1465                1470

Ser Gly Asp Phe Arg Leu Ser Ser Asn Tyr Asp Ala His Asp Ile Tyr
        1475                1480                1485

Tyr Leu Asn Pro Ala Asp Ile Leu Glu Asp Thr Pro Tyr Ile Thr Pro
        1490                1495                1500

Asp Gly Gln Lys Ile His Arg Ala Ile Val Arg Leu Thr Pro Gln Thr
1505                1510                1515                1520

Ser Ala Tyr Phe Tyr Ala Arg Gly Gly Leu His Ala Ser Gln Ala Glu
            1525                1530                1535

Arg Arg Arg Leu Asp Leu Thr Ala Arg Thr Gly Asp Ser Val Val Leu
            1540                1545                1550

Tyr Tyr Thr Asp Arg Gln Asp Lys Gln Pro Asn Pro Asp His Val Ala
        1555                1560                1565

Ala Ala Ala Thr Asn Asp Ser Ala Phe Ile Gly Leu Asp Ala Pro Gln
        1570                1575                1580

Gln Asn Glu Arg Leu Lys Ile Val Pro Ile Thr Tyr Ala Pro Gly Asp
1585                1590                1595                1600

Asp Arg Leu Thr Tyr Asp Pro Thr Tyr Gly Thr Cys Thr Asp Asp Cys
            1605                1610                1615

Val Arg Leu Val Thr Trp His Asp Tyr Thr Asp Pro Asp His Thr Leu
            1620                1625                1630

Ile Asp Met Arg Arg Gly Pro Asn Asp Val Asp Asp Asn Glu Arg Glu
        1635                1640                1645

Arg His Ala Thr Arg Thr Thr Gln Gln Glu Ile Leu Asn Pro Asp Ala
        1650                1655                1660

Gly Ala Pro Ala Leu Ile Gln Ser Gly Gly Thr Met Arg Ile Asp Val
1665                1670                1675                1680
```

```
Gly Tyr Leu Tyr Asn His Tyr Ala Asp Leu Leu Ala Gly Gly Asp Gln
            1685                1690                1695

Thr Ile Val Gly Leu Pro Pro His Pro Thr Lys Glu Thr Ala Asp Asp
            1700                1705                1710

Glu His Lys Tyr Asn Arg Ala Leu Leu Ile Asp Asn Arg Ala Leu Gln
            1715                1720                1725

Leu Ser Arg Thr Asp Arg Phe Gln Asn Ile Ser Thr Thr Tyr Arg Gly
            1730                1735                1740

Lys Asp Ser Ala Pro Trp Ser Asn Glu Ser Arg Thr Thr Pro Thr Thr
1745                1750                1755                1760

Gln Ile Gly Gly Arg Ile Thr Ser Gly Gly His Gln His Ile Ala Ala
            1765                1770                1775

Gln Thr Phe Asn Asn Val Thr Asp Ser Thr His Ala Pro Glu Pro Ile
            1780                1785                1790

Gln His Val Thr Tyr Asn Pro Ser Thr Gln Thr Leu Thr Ile Ala Asp
            1795                1800                1805

Gly His Ile Thr Val Thr Asp Thr Pro Pro Ser Leu His Thr Val Ser
            1810                1815                1820

Leu Ala Asp Asn Gly Phe Ser His Gly Gln Glu Leu Thr Tyr Ile Pro
1825                1830                1835                1840

Glu Lys Ser Ile Thr Thr Pro Asn Ala Pro Ile Arg Asp Pro Ala Ala
            1845                1850                1855

Pro Pro Arg Arg His Arg His Pro His Arg Pro Pro His Pro Ala Gln
            1860                1865                1870

Gln Gln Pro Leu His His Ser Pro Arg His Arg His Pro His His His
            1875                1880                1885

Arg Pro Pro Leu Tyr Pro Arg Pro Pro Leu His Gln Arg Arg Gln Pro
            1890                1895                1900

Thr Pro Arg Pro Gly Arg Pro Arg His Pro Pro Gln Thr Pro Arg Arg
1905                1910                1915                1920

Arg Leu Leu Arg Thr Thr Pro His Pro Arg Thr Asn His Pro Thr His
            1925                1930                1935

Arg Pro Pro Pro Gly Arg Leu His Arg Arg Pro Pro Ile Pro
            1940                1945                1950

Arg Pro Pro Gly Arg Arg Pro His Arg Arg Gln Thr Ala Pro Thr Ala
            1955                1960                1965

Pro Arg His Cys Pro Gln Cys Arg Pro Asn Gly Pro Thr His Gln Arg
            1970                1975                1980

His Arg Leu Ala Arg Pro Thr Arg Arg Pro Pro Ala Arg Arg His His
1985                1990                1995                2000

His Arg Arg Pro Arg Pro Pro Leu Pro Ala Pro Pro His Arg Arg
            2005                2010                2015

Pro His Pro Arg Arg Arg Pro Pro Gly Gly Arg Gln His His His Gln
            2020                2025                2030

Arg Pro His Pro His Gln His Arg His His Arg Pro Arg Pro His Gln
            2035                2040                2045

His Gln His Pro His His Gly Pro Thr Arg Arg Pro Pro Tyr Arg Arg
            2050                2055                2060

Arg His Gln His Pro His His Arg Arg Leu His Gln Pro Gly Arg Thr
2065                2070                2075                2080

Ile His Arg Arg Arg Leu Pro Gln Ser Pro Cys Pro Arg Gln Leu Pro
            2085                2090                2095

Cys Gln His Pro Thr Arg Arg His His Pro Arg His Pro Pro Pro Gln
```

```
                2100                2105                2110
Arg Asp Gly Thr Gly Pro Thr Gly Arg Leu His Arg His Arg Pro Arg
            2115                2120                2125
Arg Leu Pro Arg Leu Glu His Arg Pro Ser His Asp Pro Thr Ser Arg
            2130                2135                2140
Cys His Gln Gln His Arg Pro Arg Leu His Leu Pro Gln Ser His Arg
2145                2150                2155                2160
Pro Pro Thr Pro Gly His Pro Gln His Pro Gln Arg His His Pro
                2165                2170                2175
Val Gly Pro Pro Gln Gln Pro His Pro His Arg Tyr Arg Thr Arg
            2180                2185                2190
His Gln His His Arg Gln Arg Tyr Gln His Gln Arg Arg Cys Arg
            2195                2200                2205
His Gln Arg Pro Cys Arg His Pro Gly Gln Gln Arg Arg Pro Asp Pro
            2210                2215                2220
Asp Leu Gln Thr Arg Gln Arg Asp Pro Ala Gly Arg Arg Ser Thr Pro
2225                2230                2235                2240
Gln Pro Thr Arg Ala His Gln Pro Pro Gln Arg Pro Ala Pro Phe Gln
            2245                2250                2255
Gln Gln Pro Gln His Leu Gln Gln His Arg Tyr Arg Arg Pro Leu Gln
            2260                2265                2270
Arg Pro Gly Arg Gln Glu His His His Arg Arg Arg His Cys Pro
            2275                2280                2285
Gln Arg Arg His Pro Val His Cys Ser Arg His Arg His Leu Arg His
            2290                2295                2300
Gln Gly Arg Ala Pro Gly Glu Arg Thr Lys His Pro Gln Leu Gln Leu
2305                2310                2315                2320
His Gln Pro Thr Ala Gln Arg Pro Leu Pro Arg Arg Pro Gly Cys
            2325                2330                2335
Glu His Arg Leu Gln Pro Ile Gln Thr Arg Arg His Pro Gly His Leu
                2340                2345                2350
Gln Arg Cys Gln Tyr Gly Gly Cys Thr Gln Trp Gln His His Tyr Pro
            2355                2360                2365
Leu Gln Pro Arg Gln Arg Arg Cys Cys Arg Arg Thr Ala Cys Arg Arg
            2370                2375                2380
Gln Pro Gln Arg Gln Arg Arg Gln Arg Pro Gly Arg Gly Leu Arg His
2385                2390                2395                2400
Pro Gln His Pro Arg Thr Ala Ile Gln Gln Thr Lys Arg Pro Asp His
                2405                2410                2415
Arg Leu Gln Gln Cys Ser Asn Gln His Arg Ser Gly Arg Leu Gly Pro
            2420                2425                2430
Glu Lys Pro Pro Gln Arg Pro His Arg Thr Ala Glu Gln Pro Leu Arg
            2435                2440                2445
Leu Ala Cys Pro Glu His Arg Arg Gln Arg Arg Leu Ser Gly Leu Trp
            2450                2455                2460
Arg Asn Arg His Pro Ala Gln Asp Gln Gln Pro Ala Glu His Leu Ser
2465                2470                2475                2480
Asn Arg Arg Leu Cys Arg His Gln Gln Gln Pro Lys Pro Lys Gln His
            2485                2490                2495
Glu Arg Pro His Arg Pro Arg His Pro Ile Thr Arg Arg Trp His Leu
            2500                2505                2510
His His Arg Leu Trp Cys Leu Arg Thr Gly Lys Arg Gln Ser His Thr
            2515                2520                2525
```

-continued

```
Gln Ser Arg His Arg Gln His Gln Arg His Arg Arg Pro Val Gln Gln
        2530                2535                2540

Pro Ser Glu Pro His Arg Arg Trp Gln Pro Gly Pro Gln Arg Pro
2545                2550                2555                2560

Glu His Pro Arg Thr Asn Leu Gln Pro Ala Pro Pro Gln Arg Gln Pro
                2565                2570                2575

Gly Cys Gln Asp Arg Gly Asp Arg Arg His Gln Arg Gln Arg Arg
                2580                2585                2590

Cys Gly Pro Arg Pro Arg Leu Leu Pro Pro Ala Val Arg His Pro Gly
                2595                2600                2605

His Arg Leu His Arg Gly Gln Ser Arg His His Gln Arg Trp Arg Arg
        2610                2615                2620

Cys His His Glu Gly Gly Pro Pro Gln Arg Pro Leu His Ser His His
2625                2630                2635                2640

Cys Arg Gln Pro Gly His His Gln Pro Ala Arg His Pro Ala Gly Gln
                2645                2650                2655

Arg Pro Ala Thr Pro Glu Gln His Arg Arg His Leu Gly His Gln Arg
                2660                2665                2670

Arg Arg Gln His Arg His Leu Gln Pro Gln Pro Pro Arg Arg His Pro
                2675                2680                2685

Arg Leu Arg Gln Arg Pro Gln Pro Lys Arg Pro Ile Cys Arg Gly Arg
        2690                2695                2700

Trp Leu His His Arg Arg Arg Pro Pro Ile Arg Arg Arg Pro His Gln
2705                2710                2715                2720

His Arg Pro Thr Gly Thr Pro Ser Leu Leu His Gln His His Trp Leu
                2725                2730                2735

Tyr Arg His Pro Gln Pro Gln Gln Arg Gln Arg Gln Arg Leu Trp His
                2740                2745                2750

His His Arg Gln Pro Gly Gln Arg Pro Glu Gln Lys Gln Pro Gln Arg
                2755                2760                2765

His Arg Gln Pro Trp Phe Val Asp Leu Gln Arg Pro Glu Lys Arg Arg
        2770                2775                2780

Arg Pro Met Asp Gly Gln Cys Arg Pro Gln Arg Pro Thr Gln His His
2785                2790                2795                2800

Arg Cys Arg Gly Gln Arg His Lys His Pro Gly Gln Pro Trp Gln Gln
                2805                2810                2815

Arg Arg Pro Gly His Pro Ala Pro Pro His Arg Arg Pro Pro Gly Leu
                2820                2825                2830

Lys Pro His Arg Pro Gly Arg Pro Ala Asn Arg Cys Pro Ala Ala Gln
        2835                2840                2845

Pro Gly Arg Arg Pro Ala Gly His Arg Pro Tyr His Gly Gly Pro Glu
        2850                2855                2860

His Gln Gln His Ala His Pro His Thr Gln Gln Ser Val Leu His Pro
2865                2870                2875                2880

Thr Thr Leu His Gln Arg Pro Cys Cys Gln Arg Cys Pro Gly Glu Arg
                2885                2890                2895

Thr His Arg Ser Thr Ala Pro Gly Pro Ser Gly Leu Val Gly Pro Lys
                2900                2905                2910

Thr Pro Pro Thr Arg Arg Cys Arg Thr Arg Ala His Arg Pro Gln Arg
                2915                2920                2925

Gln Pro Arg Ala Gly Ser Arg Gln Ser Gln Gly Asp Asp Cys Gln Arg
        2930                2935                2940

Arg Gly Pro Leu Gln Pro Ala Thr Pro Ala Gly Leu Arg Ala Leu Gly
2945                2950                2955                2960
```

His Gln Pro Arg His Arg Gln Cys Pro Ser Ala Ala Gly Glu Pro Gly
            2965                2970                2975

Arg Pro Gln Pro Leu Ile Gly Arg Arg Lys Glu Thr Arg His Pro Leu
        2980                2985                2990

Arg Gln Arg His Gln Arg His Pro Pro Arg Arg Gly Thr Gly Leu
    2995                3000                3005

Ala Asp Asp Ala Glu Glu Gln Gln Arg Arg His Cys Lys Arg Arg Asn
        3010                3015                3020

Leu Pro Lys His His Leu Pro Gly Val Tyr Gln Thr His Pro Pro Ala
3025                3030                3035                3040

Gly Gly Thr Gly Asp Arg Arg His Glu Thr Ala Gly Asp His Gln Asn
            3045                3050                3055

Arg Gln Pro Arg Leu Ala Ala Gly Arg Gly Gly Gln Arg Ala Asp
        3060                3065                3070

Val Arg Arg Gly Gln Lys Ile Tyr Lys Ser Asp Leu Phe Arg Gly Pro
        3075                3080                3085

Gln Pro Arg His Asp Glu Ala Gln Cys Thr Ala Gly Ala Arg Arg
        3090                3095                3100

Gly Ser Cys Val His Ser Asp Pro Arg Leu Gln Pro Cys Gly Arg Arg
3105                3110                3115                3120

Gln Pro Pro Cys Gly Arg Cys Pro Gly Asp Glu Lys Thr Ser Gln Asp
        3125                3130                3135

Leu Gly Pro Ala Gln Gly Leu Cys Gly Gln Asp Trp Arg Leu Cys Arg
        3140                3145                3150

Gln Cys His Leu Pro Ser Val Gly Asp Leu Pro Asn Gln Leu Leu Arg
        3155                3160                3165

Ala Gln Gln Arg Arg His Arg Arg Pro Gly Gln Arg Leu Lys Pro Cys
        3170                3175                3180

Gln Cys Pro Arg Val Val Gln Leu Arg Arg Pro Gly Tyr Gln Gly His
3185                3190                3195                3200

Glu Arg Gln Ala Ser Gly Ala Asp His Arg Ala Ala Ala Met Ala
        3205                3210                3215

Glu Asp Thr Gln Pro Arg Glu Pro Gly Gly Asp Pro Thr His Pro Val
        3220                3225                3230

Ala Thr Pro Ala Val Ala Ile Gly Pro Val Ala Thr Ala Val Arg Gln
        3235                3240                3245

His Pro Arg Ala Ala Asp Thr Ala His Pro Asp His Pro Gly Arg Pro
        3250                3255                3260

Gln Arg Pro Ala Thr Ala Thr Pro Thr Val Ala Pro Val Pro His Pro
3265                3270                3275                3280

Leu Leu

<210> SEQ ID NO 8
<211> LENGTH: 394
<212> TYPE: PRT
<213> ORGANISM: Xylella fastidiosa

<400> SEQUENCE: 8

Met Thr Gly Trp Ala Ile Pro Trp Arg Pro Leu Ile Thr Gln Val Met
1               5                   10                  15

Asn Arg Leu Tyr Ile Gln Asp Ser Gly Gln Thr Tyr Arg Asn Thr Thr
            20                  25                  30

Tyr Gln Ala Tyr Thr Lys Pro Thr His Gln Leu Gly Glu Leu Val Thr
        35                  40                  45

```
Ala Gly Ile Glu Lys Leu Leu Glu Ile Thr Lys Ile Ala Ser Pro Ala
 50                  55                  60

Ser Arg Leu Lys Ala Ala Ala Lys Glu Leu Met Tyr Asn Thr Glu
 65                  70                  75                  80

Gln Gly Asn Tyr Ser Asn Leu Val Tyr Leu Glu Gly His Ser Arg Gly
                 85                  90                  95

Thr Met Thr Leu Ser Asn Ala Leu Arg Val Leu Ala Gly Phe Asn Val
                100                 105                 110

Gly Asp Thr Lys Leu Glu Val Leu Ala Tyr Asn Pro Ala Ala Glu Gly
                115                 120                 125

Asn Arg Leu Asn Thr Thr Tyr Gln Ala Tyr Thr Lys Pro Thr His Gln
                130                 135                 140

Leu Gly Glu Leu Val Thr Ala Gly Ile Glu Lys Leu Leu Glu Ile Thr
145                 150                 155                 160

Lys Ile Ala Ser Pro Ala Ser Arg Leu Lys Ala Ala Ala Lys Glu
                165                 170                 175

Leu Met Tyr Asn Thr Glu Gln Gly Asn Tyr Ser Asn Leu Val Tyr Leu
                180                 185                 190

Glu Gly His Ser Arg Gly Thr Met Thr Leu Ser Asn Ala Leu Arg Val
                195                 200                 205

Leu Ala Ala Asp His Val Leu Ser Asp Thr Leu Glu Ile Arg Ala Tyr
210                 215                 220

Asn Pro Ala Ala Glu Gly Asn Arg Leu Ala Glu Ala Ala Leu Val
225                 230                 235                 240

Thr Lys Lys Pro Val Lys Thr Trp Ala Pro Pro Lys Asp Phe Val Ala
                245                 250                 255

Asn Lys Ile Gly Gly Tyr Ala Gly Asn Ala Thr Phe His Asp Leu Arg
                260                 265                 270

Glu Ile Phe Gln Thr Asn Tyr Ser Val His Ser Ser Gly Gly Thr Ala
                275                 280                 285

Ala Leu Gly Ser Asp Ser Asn His Val Asp Lys Glu Lys Leu Phe Ser
                290                 295                 300

Tyr Glu Gly Leu Asp Ile Lys Asp Met Asn Ala Lys Arg Gln Gly Arg
305                 310                 315                 320

Thr Ile Gly Leu Leu Gln Gln Trp Gln Lys Thr Arg Arg Pro Glu Asp
                325                 330                 335

Pro Val Ala Thr Gln Leu Thr Gln Leu Gln Arg Leu Leu Trp Gln Ser
                340                 345                 350

Gly Gln Trp Gln Gln Leu Asp Asn Thr Pro Gly Leu Leu Thr Arg
                355                 360                 365

Pro Thr Pro Thr Thr Pro Asp Ala Pro Ser Ala Arg Gln Gln Gln Leu
370                 375                 380

Gln Gln Leu Arg Gln Ser Leu Thr Pro Tyr
385                 390
```

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
ggagcaagac agtcgcggat       20

<210> SEQ ID NO 10

-continued

```
<211> LENGTH: 23
<212> TYPE: DNA
<213> ORGANISM: Artificial Sequence
<220> FEATURE:
<223> OTHER INFORMATION: Primer

<400> SEQUENCE: 10
gatatcgtga acgattgccg cct                                            23

<210> SEQ ID NO 11
<211> LENGTH: 16
<212> TYPE: DNA
<213> ORGANISM: Artificial Sequence
<220> FEATURE:
<223> OTHER INFORMATION: Primer

<400> SEQUENCE: 11
gttttcccag tcacga                                                    16

<210> SEQ ID NO 12
<211> LENGTH: 17
<212> TYPE: DNA
<213> ORGANISM: Artificial Sequence
<220> FEATURE:
<223> OTHER INFORMATION: Primer

<400> SEQUENCE: 12
caggaaacag ctatgac                                                   17

<210> SEQ ID NO 13
<211> LENGTH: 10
<212> TYPE: DNA
<213> ORGANISM: Artificial Sequence
<220> FEATURE:
<223> OTHER INFORMATION: Restriction site

<400> SEQUENCE: 13
caattgacgt                                                           10

<210> SEQ ID NO 14
<211> LENGTH: 25
<212> TYPE: DNA
<213> ORGANISM: Artificial Sequence
<220> FEATURE:
<223> OTHER INFORMATION: Primer

<400> SEQUENCE: 14
acctacaaca aagctctcat caacc                                          25

<210> SEQ ID NO 15
<211> LENGTH: 26
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 21
<223> OTHER INFORMATION: n = A,T,C or G

<400> SEQUENCE: 15
ggccacgcgt cgactagtac ngatat                                         26

<210> SEQ ID NO 16
<211> LENGTH: 21
<212> TYPE: DNA
<213> ORGANISM: Artificial Sequence
<220> FEATURE:
```

<223> OTHER INFORMATION: Primer

<400> SEQUENCE: 16
ctggcagagc attacgctga c                                      21

<210> SEQ ID NO 17
<211> LENGTH: 25
<212> TYPE: DNA
<213> ORGANISM: Artificial Sequence
<220> FEATURE:
<223> OTHER INFORMATION: Primer

<400> SEQUENCE: 17
gcaatgtaac atcagagatt ttgag                                  25

<210> SEQ ID NO 18
<211> LENGTH: 25
<212> TYPE: DNA
<213> ORGANISM: Artificial Sequence
<220> FEATURE:
<223> OTHER INFORMATION: Primer

<400> SEQUENCE: 18
acctacaaca aagctctcat caacc                                  25

<210> SEQ ID NO 19
<211> LENGTH: 17
<212> TYPE: DNA
<213> ORGANISM: Artificial Sequence
<220> FEATURE:
<223> OTHER INFORMATION: Primer

<400> SEQUENCE: 19
tgcaaccacg ctgaaca                                           17

<210> SEQ ID NO 20
<211> LENGTH: 15
<212> TYPE: DNA
<213> ORGANISM: Artificial Sequence
<220> FEATURE:
<223> OTHER INFORMATION: Primer

<400> SEQUENCE: 20
ggcatcgacc tcatt                                             15

<210> SEQ ID NO 21
<211> LENGTH: 24
<212> TYPE: DNA
<213> ORGANISM: Artificial Sequence
<220> FEATURE:
<223> OTHER INFORMATION: Primer

<400> SEQUENCE: 21
gctgcactcc agattgaaca ctgt                                   24

<210> SEQ ID NO 22
<211> LENGTH: 21
<212> TYPE: DNA
<213> ORGANISM: Artificial Sequence
<220> FEATURE:
<223> OTHER INFORMATION: Primer

<400> SEQUENCE: 22
acctacacct acaccactgg a                                      21

<210> SEQ ID NO 23

```
<211> LENGTH: 17
<212> TYPE: DNA
<213> ORGANISM: Artificial Sequence
<220> FEATURE:
<223> OTHER INFORMATION: Primer

<400> SEQUENCE: 23
gatctacctg ctgttgc                                                    17

<210> SEQ ID NO 24
<211> LENGTH: 22
<212> TYPE: DNA
<213> ORGANISM: Artificial Sequence
<220> FEATURE:
<223> OTHER INFORMATION: Primer

<400> SEQUENCE: 24
gtgaggatta ttacgggtgg tg                                              22

<210> SEQ ID NO 25
<211> LENGTH: 19
<212> TYPE: DNA
<213> ORGANISM: Artificial Sequence
<220> FEATURE:
<223> OTHER INFORMATION: Primer

<400> SEQUENCE: 25
cgcgtgctcg ctcttcaat                                                  19

<210> SEQ ID NO 26
<211> LENGTH: 16
<212> TYPE: DNA
<213> ORGANISM: Artificial Sequence
<220> FEATURE:
<223> OTHER INFORMATION: Primer

<400> SEQUENCE: 26
taccgaatgt ggcttg                                                     16

<210> SEQ ID NO 27
<211> LENGTH: 16
<212> TYPE: DNA
<213> ORGANISM: Artificial Sequence
<220> FEATURE:
<223> OTHER INFORMATION: Primer

<400> SEQUENCE: 27
attcacgctc catacg                                                     16

<210> SEQ ID NO 28
<211> LENGTH: 18
<212> TYPE: DNA
<213> ORGANISM: Artificial Sequence
<220> FEATURE:
<223> OTHER INFORMATION: Primer

<400> SEQUENCE: 28
atgtcgagtc ctgttgtg                                                   18

<210> SEQ ID NO 29
<211> LENGTH: 18
<212> TYPE: DNA
<213> ORGANISM: Artificial Sequence
<220> FEATURE:
<223> OTHER INFORMATION: Primer

<400> SEQUENCE: 29
```

```
aacagagtgc tagtcacc                                               18

<210> SEQ ID NO 30
<211> LENGTH: 20
<212> TYPE: DNA
<213> ORGANISM: Artificial Sequence
<220> FEATURE:
<223> OTHER INFORMATION: Primer

<400> SEQUENCE: 30
acgacttgca tagcagtagc                                             20

<210> SEQ ID NO 31
<211> LENGTH: 15
<212> TYPE: DNA
<213> ORGANISM: Artificial Sequence
<220> FEATURE:
<223> OTHER INFORMATION: Primer

<400> SEQUENCE: 31
ttgtcctgac ggtcg                                                  15

<210> SEQ ID NO 32
<211> LENGTH: 15
<212> TYPE: DNA
<213> ORGANISM: Artificial Sequence
<220> FEATURE:
<223> OTHER INFORMATION: Primer

<400> SEQUENCE: 32
ccaccattga caacc                                                  15

<210> SEQ ID NO 33
<211> LENGTH: 4
<212> TYPE: PRT
<213> ORGANISM: Xylella fastidiosa
<220> FEATURE:
<221> NAME/KEY: misc_feature
<222> LOCATION: 2
<223> OTHER INFORMATION: Xaa = any amino acid
<220> FEATURE:
<221> NAME/KEY: misc_feature
<222> LOCATION: 3
<223> OTHER INFORMATION: Xaa = any amino acid

<400> SEQUENCE: 33

Cys Xaa Xaa Cys
 1
```